(12) United States Patent
Gellerfors et al.

(10) Patent No.: US 9,034,334 B2
(45) Date of Patent: May 19, 2015

(54) PROTOFIBRIL SELECTIVE ANTIBODIES AND THE USE THEREOF

(75) Inventors: Pär Gellerfors, Lidingö (SE); Lars Lannfelt, Stockholm (SE); Dag Sehlin, Uppsala (SE); Frida Ekholm Pettersson, Uppsala (SE); Hillevi Englund, Uppsala (SE)

(73) Assignee: BioArctic Neuroscience AB, Stockholm (SE)

( * ) Notice: Subject to any disclaimer, the term of this patent is extended or adjusted under 35 U.S.C. 154(b) by 899 days.

(21) Appl. No.: 13/219,012

(22) Filed: Aug. 26, 2011

(65) Prior Publication Data

US 2012/0076726 A1 Mar. 29, 2012

Related U.S. Application Data

(62) Division of application No. 12/294,207, filed as application No. PCT/SE2007/000292 on Mar. 23, 2007, now Pat. No. 8,025,878.

(30) Foreign Application Priority Data

Mar. 23, 2006 (SE) ..................................... 0600662
Nov. 30, 2006 (SE) ..................................... 0602591

(51) Int. Cl.
*A61K 39/00* (2006.01)
*A61K 39/395* (2006.01)
*G01N 33/68* (2006.01)
*C07K 16/18* (2006.01)
*C07K 16/46* (2006.01)

(52) U.S. Cl.
CPC ...... *G01N 33/6896* (2013.01); *A61K 2039/505* (2013.01); *C07K 16/18* (2013.01); *C07K 16/465* (2013.01); *C07K 2317/24* (2013.01); *C07K 2317/565* (2013.01); *G01N 2333/4709* (2013.01); *G01N 2800/2814* (2013.01); *G01N 2800/387* (2013.01)

(58) Field of Classification Search
CPC ........... C07K 2317/565; C07K 16/465; C07K 2317/24; C07K 16/18; G01N 2800/387; G01N 2333/4709; G01N 2800/2814; G01N 33/68961; A61K 2039/505
See application file for complete search history.

(56) References Cited

U.S. PATENT DOCUMENTS

| | | |
|---|---|---|
| 5,231,000 A | 7/1993 | Majocha et al. |
| 5,604,102 A | 2/1997 | McConlogue et al. |
| 5,612,486 A | 3/1997 | McConlogue et al. |
| 5,679,531 A | 10/1997 | König et al. |
| 5,753,624 A | 5/1998 | McMichael et al. |
| 5,817,626 A | 10/1998 | Findeis et al. |
| 5,850,003 A | 12/1998 | McLonlogue et al. |
| 5,851,996 A | 12/1998 | Kline |
| 5,854,204 A | 12/1998 | Findeis et al. |
| 5,854,215 A | 12/1998 | Findeis et al. |
| 5,985,242 A | 11/1999 | Findeis et al. |
| 6,054,114 A | 4/2000 | Lansbury, Jr. et al. |
| 6,114,133 A | 9/2000 | Seubert et al. |
| 6,174,916 B1 | 1/2001 | McMichael |
| 6,218,506 B1 | 4/2001 | Krafft et al. |
| 6,245,964 B1 | 6/2001 | McLonlogue et al. |
| 6,303,567 B1 | 10/2001 | Findeis et al. |
| 6,319,498 B1 | 11/2001 | Findeis et al. |
| 7,179,463 B2 | 2/2007 | Lannfelt et al. |
| 7,427,392 B1 | 9/2008 | Seubert et al. |
| 8,025,878 B2 | 9/2011 | Gellerfors et al. |
| 8,106,164 B2 | 1/2012 | Gellerfors et al. |
| 8,409,575 B2 | 4/2013 | Lannfelt et al. |
| 2002/0162129 A1 | 10/2002 | Lannfelt et al. |
| 2003/0068316 A1 | 4/2003 | Klein et al. |
| 2003/0187011 A1 | 10/2003 | Lashuel et al. |
| 2003/0232758 A1 | 12/2003 | St. George-Hyslop et al. |
| 2004/0049134 A1 | 3/2004 | Tosaya et al. |
| 2004/0170641 A1 | 9/2004 | Schenk |
| 2004/0171815 A1 | 9/2004 | Schenk et al. |
| 2004/0171816 A1 | 9/2004 | Schenk et al. |
| 2005/0031629 A1 | 2/2005 | Schenk |
| 2005/0124016 A1 | 6/2005 | LaDu et al. |
| 2005/0142132 A1 | 6/2005 | Schenk et al. |
| 2005/0191314 A1 | 9/2005 | Schenk |
| 2005/0249725 A1 | 11/2005 | Schenk et al. |
| 2006/0079447 A1 | 4/2006 | Wetzel |
| 2006/0166275 A1 | 7/2006 | Krafft et al. |
| 2006/0178302 A1 | 8/2006 | Krafft et al. |
| 2006/0193850 A1 | 8/2006 | Warne et al. |
| 2006/0228349 A1 | 10/2006 | Acton et al. |

(Continued)

FOREIGN PATENT DOCUMENTS

| | | |
|---|---|---|
| EP | 0 783 104 | 7/1997 |
| WO | WO 91/16819 | 11/1991 |

(Continued)

OTHER PUBLICATIONS

Restriction Requirement (U.S. Appl. No. 09/899,815; U.S. Patent No. 7,179,463), mailed Jul. 3, 2002.

(Continued)

*Primary Examiner* — Gregory S Emch
*Assistant Examiner* — Adam M Weidner
(74) *Attorney, Agent, or Firm* — Clark & Elbing LLP

(57) ABSTRACT

The invention relates to an isolated antibody, or fragment thereof, having high affinity for human Aβ protofibrils. The invention further relates to compositions that include the antibody, or a fragment thereof, and a pharmaceutically acceptable buffer. The invention further relates to a method of preventing or treating Alzheimer's disease, which includes the step of administering to a patient having or suspected of having Alzheimer's disease such an antibody, or fragment thereof or a composition that includes the antibody or a fragment thereof.

4 Claims, 16 Drawing Sheets

(56) References Cited

U.S. PATENT DOCUMENTS

| | | |
|---|---|---|
| 2006/0240486 A1 | 10/2006 | Johnson-Wood et al. |
| 2006/0280733 A1 | 12/2006 | Kayed et al. |
| 2007/0048312 A1 | 3/2007 | Klein et al. |
| 2007/0081998 A1 | 4/2007 | Kinney et al. |
| 2007/0098721 A1 | 5/2007 | Hillen et al. |
| 2007/0099185 A1 | 5/2007 | Hagen et al. |
| 2007/0110750 A1 | 5/2007 | Glabe et al. |
| 2007/0148167 A1 | 6/2007 | Strohl |
| 2008/0181902 A1 | 7/2008 | Lannfelt et al. |
| 2012/0076726 A1 | 3/2012 | Gellerfors et al. |
| 2012/0100129 A1 | 4/2012 | Gellerfors et al. |

FOREIGN PATENT DOCUMENTS

| | | |
|---|---|---|
| WO | WO 95/11994 | 5/1995 |
| WO | WO 95/31996 | 11/1995 |
| WO | WO 96/15452 A1 | 5/1996 |
| WO | WO 97/41856 | 11/1997 |
| WO | WO 98/33815 | 8/1998 |
| WO | WO 99/27944 | 6/1999 |
| WO | WO 99/27949 | 6/1999 |
| WO | WO 00/39310 | 7/2000 |
| WO | WO 00/71671 | 11/2000 |
| WO | WO 00/72870 | 12/2000 |
| WO | WO 00/72876 | 12/2000 |
| WO | WO 00/72880 | 12/2000 |
| WO | WO 01/10900 | 2/2001 |
| WO | WO 01/39796 | 6/2001 |
| WO | WO 01/90182 | 11/2001 |
| WO | WO 02/03911 A2 | 1/2002 |
| WO | WO 03/089460 | 10/2003 |
| WO | WO 03/104437 | 12/2003 |
| WO | WO 2004/024090 A2 | 3/2004 |
| WO | WO 2004/031400 | 4/2004 |
| WO | WO 2005/019828 | 3/2005 |
| WO | WO 2005/025516 | 3/2005 |
| WO | WO-2005/025516 A2 | 3/2005 |
| WO | WO 2005/089539 A1 | 9/2005 |
| WO | WO 2005/123775 A1 | 12/2005 |
| WO | WO 2006/014478 | 2/2006 |
| WO | WO 2006/047254 | 5/2006 |
| WO | WO 2006/055178 | 5/2006 |
| WO | WO 2006/066233 A1 | 6/2006 |
| WO | WO 2006/083533 | 8/2006 |
| WO | WO 2006/094724 | 9/2006 |
| WO | WO 2006/137325 | 12/2006 |
| WO | WO 2007/005358 | 1/2007 |
| WO | WO 2007/005359 | 1/2007 |
| WO | WO 2007/050359 | 5/2007 |
| WO | WO 2007/062088 | 5/2007 |
| WO | WO 2007/108756 A1 | 9/2007 |
| WO | WO-2009/065054 A2 | 5/2009 |
| WO | WO-2011/001366 A1 | 1/2011 |

OTHER PUBLICATIONS

Reply to Restriction Requirement (U.S. Appl. No. 09/899,815; U.S. Patent No. 7,179,463), filed Sep. 3, 2002.
Office Action (U.S. Appl. No. 09/899,815; U.S. Patent No. 7,179,463), mailed Nov. 19, 2002.
Reply to Office Action (U.S. Appl. No. 09/899,815; U.S. Patent No. 7,179,463), filed Apr. 21, 2003.
Office Action (U.S. Appl. No. 09/899,815; U.S. Patent No. 7,179,463), mailed Jun. 25, 2003.
Interview Summary (U.S. Appl. No. 09/899,815; U.S. Patent No. 7,179,463), dated Oct. 21, 2003.
Notice of Appeal (U.S. Appl. No. 09/899,815; U.S. Patent No. 7,179,463), filed Nov. 25, 2003.
Reply to Office Action (U.S. Appl. No. 09/899,815; U.S. Patent No. 7,179,463), filed Dec. 18, 2003.
Resubmission of Reply to Office Action (U.S. Appl. No. 09/899,815; U.S. Patent No. 7,179,463), filed Feb. 3, 2004.
Advisory Action (U.S. Appl. No. 09/899,815; U.S. Patent No. 7,179,463), mailed Feb. 20, 2004.
Request for Continued Examination (U.S. Appl. No. 09/899,815; U.S. Patent No. 7,179,463), filed Mar. 25, 2004.
Restriction Requirement (U.S. Appl. No. 09/899,815; U.S. Patent No. 7,179,463), mailed Jun. 10, 2004.
Reply to Restriction Requirement (U.S. Appl. No. 09/899,815; U.S. Patent No. 7,179,463), filed Sep. 10, 2004.
Supplemental Reply to Restriction Requirement (U.S. Appl. No. 09/899,815; U.S. Patent No. 7,179,463), filed Sep. 21, 2004.
Office Action (U.S. Appl. No. 09/899,815; U.S. Patent No. 7,179,463), mailed Nov. 24, 2004.
Reply to Office Action (U.S. Appl. No. 09/899,815; U.S. Patent No. 7,179,463), filed Mar. 24, 2005.
Notice of Non-Compliant Amendment (U.S. Appl. No. 09/899,815; U.S. Patent No. 7,179,463), mailed May 12, 2005.
Reply to Notice of Non-Compliant Amendment (U.S. Appl. No. 09/899,815; U.S. Patent No. 7,179,463), filed May 27, 2005.
Office Action (U.S. Appl. No. 09/899,815; U.S. Patent No. 7,179,463), mailed Jul. 7, 2005.
Reply to Office Action (U.S. Appl. No. 09/899,815; U.S. Patent No. 7,179,463), filed Oct. 7, 2005.
Office Action (U.S. Appl. No. 09/899,815; U.S. Patent No. 7,179,463), mailed Nov. 9, 2005.
Reply to Office Action (U.S. Appl. No. 09/899,815; U.S. Patent No. 7,179,463), filed Mar. 9, 2006.
Declaration Under Rule 132 (U.S. Appl. No. 09/899,815; U.S. Patent No. 7,179,463), filed Mar. 9, 2006.
Office Action (U.S. Appl. No. 09/899,815; U.S. Patent No. 7,179,463) mailed May 8, 2006.
Reply to Office Action (U.S. Appl. No. 09/899,815; U.S. Patent No. 7,179,463), filed Aug. 8, 2006.
Notice of Allowance (U.S. Appl. No. 09/899,815; U.S. Patent No. 7,179,463), mailed Oct. 16, 2006.
Chromy et al., "Self-Assembly of $A\beta_{1-42}$ Into Globular Neurotoxins," *Biochemistry* 42:12749-12760, 2003.
Lannfelt et al., "Genetics, Pathophysiology and Aβ Protofibril Formation in Alzheimer's Disease," *Neurobiol. Aging* 25(Suppl. 2): Poster Session P2: Epidemiology and Risk Factors of Alzheimer's Disease P2-268; S308, 2004.
Terminology relating to clones BA2, BA3, 7E4, and 10F7 dated Sep. 18, 2009.
Response to Communication in European Patent Application No. 07747965.7-1222, filed Sep. 11, 2009.
Response to Communication in European Patent Application No. 07747965.7-1222, filed Jan. 29, 2010.
Axelman et al., "A Large Swedish Family with Alzheimer's Disease with a Codon 670/671 Amyloid Precursor Protein Mutation," *Arch. Neurol.* 51:1193-1197, 1994.
Forsell et al., "Amyloid Precursor Protein Mutation at Codon 713 (Ala→Val) Does Not Cause Schizophrenia: Non-Pathogenic Variant Found at Codon (Silent)," *Neurosci. Lett.* 184:90-93, 1995.
Jensen et al., "Quantification of Alzheimer Amyloid β Peptides Ending at Residues 40 and 42 by Novel ELISA Systems," *Mol. Med.* 6:291-302, 2000.
Johansson et al., "Physiochemical Characterization of the Alzheimer's Disease-Related Peptides Aβ1-42 Arctic and Aβ1-42 wt" *FEBS J.* 273:2618-2630, 2006.
Johnston et al., "Increased β-Amyloid Release and Levels of Amyloid Precursor Protein (APP) in Fibroblast Cell Lines From Family Members With the Swedish Alzheimer's Disease APP670/671 Mutation," *FEBS Lett.* 354:274-278, 1994.
Lannfelt et al., "Amyloid Precursor Protein Mutation Causes Alzheimer's Disease in a Swedish Family," *Neurosci. Lett.* 168:254-256, 1994.
Lannfelt et al., "Amyloid β-Peptide in Cerebrospinal Fluid in Individuals with the Swedish Alzheimer Amyloid Precursor Protein Mutation," *Neurosci. Lett.* 199:203-206, 1995.
Lannfelt et al., "Genetics of Alzheimer's Disease—Routes to the Pathophysiology," *J. Neural. Transm.* [Suppl.] 59:155-161, 2000.
Lannfelt et al., "Monoclonal Antibodies Selective for Aβ Protofibrils Reduce Plaque Sensitive Detection of Alzheimer Aβ Protofibrils by Burden in Transgenic Mice Models of Alzheimer's Disease Conformation Specific ELISA," ICAD meeting, Uppsala University, Sweden, Jul. 16, 2006.

(56) References Cited

OTHER PUBLICATIONS

Lannfelt et al., "Monoclonal Antibodies Selective for Aβ Protofibrils: Detection of Protofibrils and Reduction of Plaque Burden in Tg-mice Models of Alzheimer's Disease," SfN meeting, Uppsala University, Sweden, Oct. 17, 2006.
Mullan et al., "A Pathogenic Mutation for Probable Alzheimer's Disease in the APP Gene at the N-terminus of β-Amyloid," *Nature Genet.* 1:345-347, 1992.
Nilsberth et al., "A Novel APP Mutation (E693G)—The Arctic Mutation, Causing, Alzheimer's Disease with Vascular Symptoms," *Society for Neuroscience Annual Meeting*, Miami Beach, Abstract, 120.4; Nov. 1999.
Nilsberth et al., "The 'Arctic' APP Mutation (E693G) Causes Alzheimer's Disease by Enhanced Aβ Protofibril Formation," *Neurobiology of Aging*, May-Jun. 2000, 21, Abstract 265, Supplement 1, 1-304.
Nilsberth et al., "The Artic APP Mutation (E693G) Causes Alzheimer's Disease Through a Novel Mechanism: Increased Amyloid β Protofibril Formation and Decreased Amyloid β Levels in Plasma and Conditioned Media," *Neurobiol. Aging* 21:S58, 2000.
Nilsberth et al., "The 'Arctic' APP Mutation (E693G) Causes Alzheimer's Disease by Enhanced Aβ Protofibril Formation," *Nature Neurosci.* 4(9):887-893, 2001.
Päiviö et al., "Unique Physicochemical Profile of β-Amyloid Peptide Variant Aβ1-40E22G Protofibrils: Conceivable Neuropathogen in Arctic Mutant Carriers," *J. Med. Biol.* 339:145-159, 2004.
Sahlin et al., "The Arctic Alzheimer Mutation Favors Intracellular Amyloid-β Production by Making Amyloid Precursor Protein Less Available to α-secretase," *J. Neurochem.* 101:854-862, 2007.
Scheuner et al., "Secreted Amyloid β-Protein Similar to That in the Senile Plaques of Alzheimer's Disease is Increased In Vivo by the Presenilin 1 and 2 and APP Mutations Linked to Familial Alzheimer's Disease," *Nature Med.* 2(8):864-870, 1996.
Stenh et al., "Amyloid-β Oligomers are Inefficiently Measured by Enzyme-Linked Immunosorbent Assay," *Ann. Neurol.* 58: 147-150, 2005.
Stenh et al., "The Arctic Mutation Interferes with Processing of the Amyloid Precursor Protein," *NeuroReport* 13: 1857-1860, 2002.
Minutes from Oral Proceedings for European Patent Application No. 01945896.7-2402, dated Dec. 17, 2008.
European Examination Report (EP 01 945 896.7), dated Apr. 24, 2007.
European Examination Report (EP 01 945 896.7), dated May 22, 2006.
European Examination Report (EP 01 945 896.7), dated Sep. 30, 2005.
Extended European Search Report from European Patent Application No. 07747965.7, dated May 13, 2009.
International Preliminary Report (PCT/US2003/30930), completed Feb. 6, 2006.
International Preliminary Report on Patentability (PCT/US2003/19640), completed Aug. 7, 2006.
International Preliminary Report on Patentability (PCT/SE01/01553), completed Oct. 23, 2002.
International Preliminary Report on Patentability (PCT/SE05/000993), issued Dec. 28, 2006.
International Preliminary Report on Patentability (PCT/SE07/000292), issued Sep. 23, 2008.
International Search Report (PCT/SE01/01553), mailed Feb. 4, 2002.
International Search Report (PCT/SE05/000993), mailed Oct. 4, 2005.
International Search Report (PCT/SE07/000292), mailed Jul. 20, 2007.
Notice of intent to grant a European patent and Annex (Reasons for Decision) (EP 01 945 896.7), dated Mar. 18, 2009.
Reply to Examination Report (European Patent Application No. 01945896.7-2402), mailed Apr. 7, 2006.
Reply to Examination Report (European Patent Application No. 01945896.7-2402), mailed Sep. 22, 2006.
Reply to Examination Report (European Patent Application No. 01945896.7-2402), mailed Nov. 5, 2007.
Request Pursuant to Oral Proceedings (European Patent Application No. 01945896.7-2402), mailed Oct. 10, 2008.
Summons to Attend Oral Proceedings (European Patent Application No. 01945896.7-2402), dated Jul. 25, 2008.
Written Opinion of the International Searching Authority (PCT/SE05/000993), mailed Oct. 4, 2005.
Written Opinion of the International Searching Authority (PCT/SE07/000292), mailed Jul. 20, 2007.
Giasson et al., "A Panel of Epitope-Specific Antibodies Detects Protein Domains Distributed Throughout Human Alpha-Synuclein in Lewy Bodies of Parkinson's Disease," *J. Neurosci. Res.* 59:528-533, 2000.
Klein et al., "Oligemia-Induced Expression of c-fos and Oxidative Stress-Related Protein in the Murine Brain," 30th Annual Meeting of the Society of Neuroscience, New Orleans, LA, Nov. 4-9, 2000, *Soc. Neurosci. Abstracts* 26(1-2), Abstract 383.15, 2000.
Klyubin et al., "Inhibitory Effect of Amyloid-β Peptide with the Arctic Mutation on Long-term Potentiation in Area CA1 of Rat Hippocampus In Vivo," *J. Physiol.* 551P, C32, 2003.
Tagliavini et al., "A New βAPP Mutation Related to Hereditary Cerebral Haemorrhage," *Alz. Report* 2(Suppl. 1):S28, Abstract 23, 1999.
Communication from European Patent Application No. 05753672.4-2402, mailed Jul. 6, 2009.
Golabek et al., "The Interaction between Apolipoprotein E and Alzheimer's Amyloid β-Peptide Is Dependent on β-Peptide Conformation," *J. Biol. Chem.* 271(18):10602-10606, 1996.
Communication as issued by European Patent Office regarding extended European Search Report for European Patent Application No. 07747965.7, dated May 13, 2009.
Search Report and Written Opinion as issued by Intellectual Property Office of Singapore regarding Singapore Patent Application No. 200803655-0, dated Oct. 8, 2009.
Communication as issued by European Patent Office for European Patent Application No. 07747965.7, dated Nov. 17, 2009.
Appellant's Statement of Grounds of Appeal together with a Main Request, First Auxiliary Request and Second Auxiliary Request for consideration by the Appeal Board, and a signed Declaration by Professor Dominic Walsh of the Conway Institute, Dublin, IE as filed in European Patent Application No. 01945896.7, Jan. 15, 2010.
Communication as issued by European Patent Office for European Patent Application No. 07747965.7, dated Mar. 26, 2010.
Communication as issued by European Patent Office regarding extended European Search Report for European Patent Application No. 08019830.2, dated May 31, 2010.
Declaration of Pär Gellerfors, dated Nov. 28, 2010.
Office Action for U.S. Appl. No. 11/570,995, issued Feb. 22, 2011.
Lord et al., "The Arctic Alzheimer Mutation Facilitates Early Intraneuronal Abeta Aggregation and Senile Plaque Formation in Transgenic Mice," *Neurobiol. Aging* 27:67-77 (2006).
Andreasen and Blennow, "Beta-amyloid (Abeta) Protein in Cerebrospinal Fluid as a Biomarker for Alzheimer's Disease," *Peptides* 23:1205-1214, 2002.
Bacskai et al., "Imaging of Amyloid-β Deposits in Brains of Living Mice Permits Direct Observation of Clearance of Plaques with Immunotherapy," *Nature Med.* 7(3):369-372, 2001.
Bard et al., "Peripherally Administered Antibodies Against Amyloid β-Peptide Enter the Central Nervous System and Reduce Pathology in a Mouse Model of Alzheimer Disease," *Nature Med.* 6(8):916-919, 2000.
Barghorn et al., "Globular Amyloid β-Peptide Oligomer: A Homogenous and Stable Neuropathological Protein in Alzheimer's Disease," *J. Neurochem.* 95:834-47, 2005.
Bayer et al., "Evaluation of the Safety and Immunogenicity of Synthetic Aβ42 (AN1792) in Patients with AD," *Neurology* 64:94-101, 2005.
Bitan et al., "Amyloid β-Protein (Aβ) Assembly: Aβ40 and Aβ42 Oligomerize Through Distinct Pathways," *Proc. Natl. Acad. Sci. U.S.A.* 100:330-5, 2003.

(56) References Cited

OTHER PUBLICATIONS

Blanchard et al., "Efficient Reversal of Alzheimer's Disease Fibril Formation and Elimination of Neurotoxicity by a Small Molecule," *Proc. Natl. Acad. Sci. U.S.A.* 101(40):14326-32, 2004.
Cai et al., "Release of Excess Amyloid β-Protein from a Mutant Amyloid β-Protein Precursor," *Science* 259:514-516, 1993.
Caughey and Lansbury, "Protofibrils, Pores, Fibils, and Neurodegeneration: Separating the Responsible Protein Aggregates from the Innocent Bystanders," *Ann. Rev. Neurosci.* 26:267-98, 2003.
Chen et al., "A Learning Deficit Related to Age and β-Amyloid Plaques in a Mouse Model of Alzheimer's Disease," *Nature* 408:975-978, 2000.
Chromy et al., "Stability of Small Oligomers of $A\beta_{1-42}$(ADDLs)," *Society for Neuroscience* 25:2129; 852.5, 1999.
Citron et al., "Mutation of the β-Amyloid Precursor Protein in Familial Alzheimer's Disease Increases β-Protein Production," *Nature* 360:672-674, 1992.
Citron et al., "Mutant Presenilins of Alzheimer's Disease Increase Production of 42-Residue Amyloid β-Protein in Both Transfected Cells and Transgenic Mice," *Nature Med.* 3(1):67-72, 1997.
Conway et al., "Acceleration of Oligomerization, Not Fibrillization, is a Shared Property of Both α-Synuclein Mutations Linked to Early-Onset Parkinson's Disease: Implications for Pathogenesis and Therapy," *Proc. Natl. Acad. Sci. U.S.A.* 97(2):571-576, 2000.
Dahlgren et al., "Oligomeric and Fibrillar Species of Amyloid-β Peptides Differentially Affect Neuronal Viability," *J. Biol. Chem.* 277:32046-53, 2002.
Dalfo et al., "Evidence of Oxidative Stress in the Neocortex in Incidental Lewy Body Disease," *J. Neuropathol. Exp. Neurol.* 64(9):816-830, 2005.
De Jonghe et al., "Flemish and Dutch Mutations in Amyloid β Precursor Protein Have Different Effects on Amyloid β Secretion," *Neurobiol. Dis.* 5:281-286, 1998.
DeMarco et al., "From Conversion to Aggregation: Protofibril Formation of the Prion Protein," *Proc. Natl. Acad. Sci. U.S.A.* 101:2293-2298, 2004.
Dodart et al., "Immunization Reverses Memory Deficits Without Reducing Brain Aβ Burden in Alzheimer's Disease Model," *Nature Neurosci.* 5:452-457, 2002.
El-Agnaf et al., "Oligomerization and Toxicity of β-Amyloid-42 Implicated in Alzheimer's Disease," *Biochem. Biophys. Res. Comm.* 273:1003-1007, 2000.
Enya et al., "Appearance of Sodium Dodecyl Sulfate-Stable Amyloid β-Protein (Aβ) Dimer in the Cortex During Aging," *Am. J. Pathol.* 154:271-279, 1999.
Finder and Glockshuber, "Amyloid-β Aggregation," *Neurodegener. Dis.* 4(1):13-27, 2007.
Frackowiak et al., "Non-Fibrillar β-Amyloid Protein is Associated with Smooth Muscle Cells of Vessel Walls in Alzheimer Disease," *J. Neuropathol. Exp. Neurol.* 53:637-645, 1994.
Frenkel et al, "Modulation of Alzheimer's Beta-amyloid Neurotoxicity by Site-directed Single-chain Antibody," *Neuroimmunomodulation* 6:444, 1999.
Frenkel et al., "Immunization Against Alzheimer's β-Amyloid Plaques Via EFRH Phage Administration," *Proc. Natl. Acad. Sci. U.S.A.* 97(21):11455-11459, 2000.
Frenkel et al, "Modulation of Alzheimer's Beta-amyloid Neurotoxicity by Site-directed Single-chain Antibody," *J. Neuroimmunol.* 106:23-31, 2000.
Giulian et al., "The HHQK Domain of β-Amyloid Provides a Structural Basis for the Immunopathology of Alzheimer's Disease," *J. Biol. Chem.* 273(45):29719-29726, 1998.
Glenner et al., "Alzheimer's Disease: Initial Report of the Purification and Characterization of a Novel Cerebrovascular Amyloid Protein," *Biochem. Biophys. Res. Comm.* 120(3):885-890, 1984.
Grabowski et al., "Novel Amyloid Precursor Protein Mutation in an Iowa Family with Dementia and Severe Cerebral Amyloid Angiopathy," *Ann. Neurol.* 49:697-705, 2001.
Guerette et al., "Oligomeric Aβ in PBS-Soluble Extracts of Human Alzheimer Brain," *Society for Neuroscience* 25:2129; 852.1, 1999.

Hardy, "Framing β-Amyloid," *Nature Genet.* 1:233-234, 1992.
Hardy, "Amyloid, the Presenilins and Alzheimer's Disease," *Trends Neurosci.* 20(4):154-159, 1997.
Harper et al., "Observation of Metastable Aβ Amyloid Protofibrils by Atomic Force Microscopy," *Chem. Biol.* 4:119-125, 1997.
Harper et al., "Assembly of Aβ Amyloid Protofibrils: An In Vitro Model for a Possible Early Event in Alzheimer's Disease," *Biochemistry* 38:8972-8980, 1999.
Hartley et al., "Protofibrillar Intermediates of Amyloid β-Protein Induce Acute Electrophysiological Changes and Progressive Neurotoxicity in Cortical Neurons," *J. Neurosci.* 19(20):8876-8884, 1999.
Hendriks et al., "Presenile Dementia and Cerebral Hemorrhage Linked to a Mutation at Codon 692 of the β-Amyloid Precursor Protein Gene," *Nature Genet.* 1:218-221, 1992.
Hock and Nitsch, "Clinical Observations with AN-1792 Using TAPIR Analyses," *Neurodegener Dis.* 2:273-276, 2005.
Hoshi et al., "Spherical Aggregates of β-Amyloid (Amylospheroid) Show High Neurotoxicity and Activate Tau Protein Kinase I/glycogen Synthase Kinase-3β," *Proc. Natl. Acad. Sci. U.S.A.* 100(11):6370-6375, 2003.
Isaacs et al., "Acceleration of Amyloid β-Peptide Aggregation by Physiological Concentrations of Calcium," *J. Biol. Chem.* 281(38):27916-23, 2006.
Janus et al., "A β Peptide Immunization Reduces Behavioral Impairment and Plaques in a Model of Alzheimer's Disease," *Nature* 408:979-982, 2000.
Kamino et al., "Linkage and Mutational Analysis of Familial Alzheimer Disease Kindreds for the APP Gene Region," *Am. J. Hum. Genet.* 51:998-1014, 1992.
Kang et al., "The Precursor of Alzheimer's Disease Amyloid A4 Protein Resembles a Cell-surface Receptor," *Nature* 325:733-736, 1987.
Kayed et al., "Immunization With a Molecular Mimic of a Toxic Aggregates Generates a Conformation-Dependent Antibody Specific for High Molecular Weight A Aggregates (Micelles and Protofibrils)," 32nd Annual Meeting of the Society for Neuroscience, Orlando, Florida (*Society for Neuroscience Abstract Viewer and Itinerary Planner*, Abstract No. 685.3, 2002).
Kayed et al., "Common Structure of Soluble Amyloid Oligomers Implies Common Mechanism of Pathogenesis," *Science* 300:486-489, 2003.
Kirkitadze et al., "Paradigm Shifts in Alzheimer's Disease and Other Neurodegenerative Disorders: The Emerging Role of Oligomeric Assemblies," *J. Neurosci. Res.* 1, 69:567-77, 2002.
Klafki et al., "Therapeutic Approaches to Alzheimer's Disease," *Brain* 129:2840-2855, 2006.
Klein et al., "Oligomer/Conformation-Dependent Aβ Antibodies," *Soc. Neurosci. Abstr.* Presentation No. 475.11, Tuesday Nov. 7, 2000.
Klein et al., "Targeting Small Aβ Oligomers: The Solution to an Alzheimer's Disease Conundrum?" *Trends Neurosci.* 24:219-224, 2001.
Klein, "Aβ Toxicity in Alzheimer's Disease," *Contemporary Clinical Neuroscience: Molecular Mechanisms of Neurodegenerative Diseases* 1.1 Introduction, 2001.
Klyubin et al., "Soluble Arctic Amyloid β Protein Inhibits Hippocampal Long-Term Potentiation In Vivo," *Eur. J. Neurosci.* 19:2839-2846, 2004.
Kuo et al., "Water-soluble Aβ (N-40, N-42) Oligomers in Normal and Alzheimer Disease Brains," *J. Biol. Chem.* 271:4077-4081, 1996.
Lambert et al., "Diffusible, Nonfibrillar Ligands Derived From $A\beta_{1-42}$ Are Potent Central Nervous System Neurotoxins," *Proc. Natl. Acad. Sci. U.S.A.* 95:6448-6453, 1998.
Lambert et al., "Neuron Dysfunction and Death Caused by Small Aβ Oligomers: Role of Signal Transduction," *Society for Neuroscience* 25:2129, 1999.
Lambert et al., "Vaccination With Soluble Aβ Oligomers Generates Toxicity-Neutralizing Antibodies," *J. Neurochem.* 79:595-605, 2001.
Lambert et al., "Monoclonal Antibodies that Target Pathological Assemblies of Aβ," *J. Neurochem.* 100:23-35, 2007.
Lashuel et al., "Mixtures of Wild-Type and a Pathogenic (E22G) Form of Aβ40 In Vitro Accumulate Protofibrils, Including Amyloid Pores," *J. Mol. Biol.* 332:795-808, 2003.

(56) References Cited

OTHER PUBLICATIONS

Lee et al., "Targeting Amyloid-β Peptide (Aβ) Oligomers by Passive Immunization with a Conformation-selective Monoclonal Antibody Improves Learning and Memory in Aβ Precursor Protein (APP) Transgenic Mice," *J. Biol. Chem.* 281:4292-4299, 2006.

Levy et al., "Mutation of the Alzheimer's Disease Amyloid Gene in Hereditary Cerebral Hemorrhage, Dutch Type," *Science* 248:1124-1126, 1990.

Liu et al., "Residues 17-20 and 30-35 of β-Amyloid Play Critical Roles in Aggregation," *J. Neurosci. Res.* 75(2):162-71, 2004.

Longo and Finch, "Nonfibrillar Aβ 1-42 (ADDL) Causes Aconitase Inactivation and Iron-dependent Neurotoxicity," *Society for Neuroscience* 25: 2129, 1999.

Masters et al., "Amyloid Plaque Core Protein in Alzheimer's Disease and Down Syndrome," *Proc. Natl. Acad. Sci. U.S.A.* 82:4245-4249, 1985.

McKhann et al., "Clinical Diagnosis of Alzheimer's Disease: Report of the NINCHS-ADRDA Work Group Under the Auspices of Department of Health and Human Services Task Force on Alzheimer's Disease," *Neurology* 34:939-944, 1994.

Miravelle et al., "Substitutions at Codon 22 of Alzheimer's Aβ Peptide Induce Diverse Conformational Changes and Apoptotic Effects in Human Cerebral Endothelial Cells," *J. Biol. Chem.* 275:27110-27116, 2000.

Morgan et al., "Aβ Peptide Vaccination Prevents Memory Loss in an Animal Model of Alzheimer's Disease," *Nature* 408:982-985, 2000.

Moss et al., "The Peptide KLVFF-$K_6$ Promotes β-Amyloid(1-40) Protofibril Growth by Association but Does Not Alter Protofibril Effects on Cellular Reduction of 3-(4,5-Dimethylthiazol-2-yl)-2,5-Diphenyltetrazolium Bromide (MTT)," *Mol. Pharmacol.* 64(5):1160-8, 2003.

Motter et al., "Reduction of β-Amyloid Peptide$_{42}$ in the Cerebrospinal Fluid of Patients with Alzheimer's Disease," *Ann. Neurol.* 38:643-648, 1995.

Nichols et al., "Amyloid-β Aggregates Formed at Polar-Nonpolar Interfaces Differ From Amyloid-β Protofibrils Produced in Aqueous Buffers," *Microsc. Res. Tech.* 67(3-4):164-74, 2005.

Nichols et al., "Growth of β-Amyloid(1-40) Protofibrils by Monomer Elongation and Lateral Association. Characterization of Distinct Products by Light Scattering and Atomic Force Microscopy," *Biochemistry* 41(19):6115-6127, 2002.

Nicoll et al., "Neuropathology of Human Alzheimer Disease After Immunization With Amyloid-β Peptide: A Case Report," *Nature Med.* 9(4):448-452, 2003.

Oda et al., "Clusterin (apoJ) Alters the Aggregation of Amyloid β-Peptide (Aβ 1-42) and Forms Slowly Sedimenting Aβ Complexes that Cause Oxidative Stress," *Exp. Neurol.* 136:22-31, 1995.

Oda et al., "Purification and Characterization of Brain Clusterin," *Biochem. Biophys. Res. Comm.* 204:1131-6, 1994.

O'Nuallain et al., "Conformational Abs Recognizes a Generic Amyloid Fibril Epitope," *Proc. Natl. Acad. Sci. U.S.A.* 99:1485-1490, 2002.

Palmert et al., "The β-Amyloid Protein Precursor of Alzheimer Disease Has Soluble Derivatives Found in Human Brain and Cerebrospinal Fluid," *Proc. Natl. Acad. Sci. U.S.A.* 86:6338-6342, 1989.

Pirttilä et al., "Soluble Amyloid β-Protein in the Cerebrospinal Fluid From Patients with Alzheimer's Disease, Vascular Dementia and Controls," *J. Neurol. Sci.* 127:90-95, 1994.

Ponte et al., "A New A4 Amyloid mRNA Contains a Domain Homologous to Serine Proteinase Inhibitors," *Nature* 331:525-527, 1988.

Qin et al., "Effect of 4-Hydroxy-2-Nonenal Modification on Alpha-Synuclein Aggregation," *J. Biol. Chem.* 282(8):5862-5870, 2007.

Roher et al., "Morphology and Toxicity of Aβ-(1-42) Dimer Derived from Neuritic and Vascular Amyloid Deposits of Alzheimer's Disease," *J. Biol. Chem.* 271:20631-20635, 1996.

Russo et al., "Presenilin-1 Mutations in Alzheimer's Disease," *Nature* 405:531-532, 2000.

Rzepecki et al., "Prevention of Alzheimer's Disease-Associated Aβ Aggregation by Rationally Designed Nonpeptitdic β-Sheet Ligands," *J. Biol. Chem.* 279:47497-47505, 2004.

Schenk et al., "Immunization with Amyloid-β Attenuates Alzheimer-Disease-Like Pathology in the PDAPP," *Nature* 400:173-177, 1999.

Selkoe, "Cell Biology of the Amyloid β-Protein Precursor and the Mechanism of Alzheimer's Disease," *Ann. Rev. Cell Biol.* 10:373-403, 1994.

Selkoe, "Normal and Abnormal Biology of the β-Amyloid Precursor Protein," *Ann. Rev. Neurosci.* 17:489-517, 1994.

Serpell, "Alzheimer's Amyloid Fibrils: Structure and Assembly," *Biochim. Biophys. Acta* 1502:16-30, 2000.

Seubert et al., "Isolation and Quantification of Soluble Alzheimer's β-Peptide From Biological Fluids," *Nature* 359:325-327, 1992.

Sherrington et al., "Cloning of a Gene Bearing Missense Mutations in Early-Onset Familial Alzheimer's Disease," *Nature* 375:754-760, 1995.

Shtilerman et al., "Molecular Crowding Accelerates Fibrillization of α-Synuclein: Could an Increase in the Cytoplasmic Protein Concentration Induce Parkinson's Disease?" *Biochemistry* 41:3855-3860, 2002.

Sigurdsson et al., "Immunization With a Nontoxic/Nonfibrillar Amyloid-β Homologous Peptide Reduces Alzheimer's Disease-Associated Pathology in Transgenic Mice," *Am. J. Pathol.* 159(2):439-447, 2001.

Solomon et al., "Disaggregation of Alzheimer β-amyloid by Site-directed mAb," *Proc. Natl. Acad. Sci. U.S.A.* 94:4109-4112, 1997.

Solomon et al., "Monoclonal Antibodies Inhibit In Vitro Fibrillar Aggregation of the Alzheimer Beta-amyloid Peptide," *Proc. Natl. Acad. Sci. U.S.A.* 93:452-455, 1996.

Solomon et al., "Monoclonal Antibodies Restore and Maintain the Soluble Conformation of β-amyloid Peptide," *Neurobiol. Aging*, vol. 17, No. 4, Suppl. 152, 1996.

Soto et al., "The Conformation of Alzheimer's β Peptide Determines the Rate of Amyloid Formation and Its Resistance to Proteolysis," *Biochem. J.* 1:314:701-7, 1996.

Srinivasan et al., "ABri Peptide Associated with Familial British Dementia Forms Annular and Ring-Like Protofibrillar Structures," *Amyloid* 11(1):10-3, 2004.

St. George-Hyslop et al., "The Genetic Defect Causing Familial Alzheimer's Disease Maps on Chromosome 21," *Science* 235:885-890, 1987.

St. George-Hyslop et al., "Genetic Linkage Studies Suggest that Alzheimer's Disease is Not a Single Homogeneous Disorder," *Nature* 347:194-197, 1990.

Stine et al., "The Nanometer-Scale Structure of Amyloid-β Visualized by Atomic Force Microscopy," *J. Prot. Chem.* 15(2):193-203, 1996.

Stine et al., "Supramolecular Structures of Aβ Aggregates and Cellular Responses," Biophysical Journal Program and Abstracts:40th Annual Meeting Feb. 17-21, 1996, *Biophys J.* 70: Abstract 239.

Suzuki et al., "An Increased Percentage of Long Amyloid β Protein Secreted by Familial Amyloid β Protein Precursor (βAPP$_{717}$) Mutants," *Science* 264:1336-1340, 1994.

Vickers, "A Vaccine Against Alzheimer's Disease: Developments to Date," *Drugs Aging* 19(7):487-494, 2002.

Walsh et al., "Amyloid β-Protein Fibrillogenesis. Detection of a Protofibrillar Intermediate," *J. Biol. Chem.* 272:22364-22372, 1997.

Walsh et al., "Amyloid β-Protein Fibrillogenesis. Structure and Biological Activity of Protofibrillar Intermediates," *J. Biol. Chem.* 274(35):25945-25952, 1999.

Walsh et al., "Naturally Secreted Oligomers of Amyloid β Protein Potently Inhibit Hippocampal Long-Term Potentiation In Vivo," *Nature* 416:535-539, 2002.

Walsh et al., "Amyloid-β Oligomers: Their Production, Toxicity and Therapeutic Inhibition," *Biochem. Soc. Trans.* 30:552-7, 2002.

Walsh et al., "Oligomers on the Brain: The Emerging Role of Soluble Protein Aggregates in Neurodegeneration," *Protein Pept. Lett.*, 11: 213-28, 2004.

Ward et al., "Fractionation and Characterization of Oligomeric, Protofibrillar Forms of β-Amyloid Peptide," Biochem. *J.* 348:137-144, 2000.

(56) References Cited

OTHER PUBLICATIONS

Weidemann et al., "Identification, Biogenesis, and Localization of Precursors of Alzheimer's Disease A4 Amyloid Protein," *Cell* 57:115-126, 1989.
Weiner et al., "Nasal Administration of Amyloid-β Peptide Decreases Cerebral Amyloid Burden in a Mouse Model of Alzheimer's Disease," *Annals Neurol.* 48(4):567-579, 2000.
Westlind-Danielsson and Arnerup, "Spontaneous In Vitro Formation of Supramolecular β-Amyloid Structures, "βamy Balls", by β-Amyloid 1-40 peptide," *Biochemistry* 40:14736-43, 2001.
Williams et al., "Structural Properties of Aβ Protofibrils Stabilized by a Small Molecule," *Proc. Natl. Acad. Sci. U.S.A.* 102(20):7115-20, 2005.
Wirak et al., "Deposits of Amyloid β Protein in the Central Nervous System of Transgenic Mice," *Science* 253:323-325, 1991.
Ye et al., "Protofibrils of Amyloid β-Protein Inhibit Specific $K^+$ Currents in Neocortical Cultures," *Neurobiol. Dis.* 13:177-190, 2003.
Yoritaka et al., "Immunohistochemical Detection of 4-Hydroxynonenal Protein Adducts in Parkinson Disease," *Proc. Natl. Acad. Sci. U.S.A.* 93:2696-2701, 1996.
Yoshikai et al., "Genomic Organization of the Human Amyloid Beta-protein Precursor Gene," *Gene* 87:257-263, 1990.
Notice of opposition to a European patent No. EP2004688 filed by Acumen Pharmaceuticals, Inc., dated Sep. 22, 2011 (22 pages).
Xu et al., "Residue at position 331 in the IgG1 and IgG4 CH2 domains contributes to their differential ability to bind and activate complement," J Biol Chem 269:3469-3474 (1994).
Proprietor's comments on the Notice of opposition to a European patent No. EP2004688 filed by Acumen Pharmaceuticals, Inc., dated Feb. 24, 2012 (10 pages).
*Antibodies: A Laboratory Manual.* Harlow & Lane (1988), pp. 626-631.
*Immunobiology.* Janeway (4th Edition, 1999), pp. 82-83.
*Immunology.* Kuby (4th Edition, 2000), p. 85.
Summons to attend oral proceedings pursuant to Rule 115(1) EPC for European Patent No. 2004688, dated Dec. 5, 2012 (29 pages).
Written Submission in response to Summons to attend oral proceedings pursuant to Rule 115(1) EPC for European Patent No. 2004688, dated Feb. 22, 2013 (43 pages).
Norlin et al., "Aggregation and fibril morphology of the Arctic mutation of Alzheimers' AB peptide by CD, TEM, STEM and insitu AFM," J Struct Biol. 180:174-189 (2012).
Studnicka et al., "Human-engineered monoclonal antibodies retain full specific binding activity by preserving non-CDR complementarity-modulating residues," Protein Engineering 7:805-814 (1994).
Sehlin et al., "Large aggregates are the major soluble AB species in AD brain fractionated with density gradient ultracentrifugation," PLoS One 7:e32014 (2012) (8 pages).
Englund et al., "Sensitive ELSA detection of amyloid-B protofibrils in biological samples," J Neurochem. 103:334-345 (2007).
Foote et al., "Antibody framework residues affecting the conformation of the hypervariable loops," J. Mol. Biol. 224:487-499 (1992).
Declaration of William Goure dated Feb. 22, 2013 (12 pages).
Curriculum Vitae of William F. Goure, Ph.D. (3 pages), 2013.
Curriculum Vitae of Pär Gellerfors (2 pages), 2013.
Affinity comparison of antibody according to EP2004688 and the antibodies of D2, (1 page), 2013.
Minutes of the oral proceedings before the Opposition Division for European patent No. EP-B-2 004 688 dated Apr. 23, 2013 (17 pages).
Interlocutory decision in opposition proceedings (Art. 101(3)(a) and 106(2) EPC) in European patent No. 2 004 688, dated Jul. 1, 2013 (39 pages).
Submission by BioArctic Neuroscience AB for European patent Application No. 01945896.7 including amended pages, amended claims, and Declaration of Prof. Lars Lannfelt, dated Apr. 7, 2006 (11 pages).
Reply to Communication under Article 96(2) for European Patent Application No. 01945896.7 (Publication No. 1309341), dated Sep. 22, 2006.
Declaration of Lars Lannfelt, (2 pages).

Statement of Grounds for European Patent Application No. 01945896.7, dated Jan. 14, 2010 (7 pages).
Request for European Patent Application No. 01945896.7 (including six auxiliary requests), filed Nov. 6, 2013 (9 pages).
Decision from the Boards of Appeal for European Patent No. 1309341, dated Nov. 21, 2013 (14 pages).
Communication under Rule 71(3) EPC for European Patent Application No. 01945896.7, dated Feb. 20, 2014, including text intended for grant (30 pages).
Response to Communication under Rule 71(3) EPC for European Patent Application No. 01945896.7 dated Jul. 2, 2014 (15 pages).
Response to Communication for European Patent Application No. 05753672.4, dated Nov. 5, 2009 (7 pages).
Communication pursuant to Article 94(3) EPC for European Patent Application No. 05753672.4, dated Jul. 8, 2010 (6 pages).
Response to Communication for European Patent Application No. 05753672.4, dated Jan. 17, 2011 (13 pages).
Third Party Observations for European Patent Application No. 05753672.4, dated Jan. 16, 2012 (6 pages).
Communication for European Patent Application No. 05753672.4, dated Mar. 22, 2012 (5 pages).
Submission in European Patent Application No. 05753672.4 in the name of BioArctic Neuroscience AB, dated May 30, 2012 (3 pages).
Declaration of Anders Lindgren included in submission in European Patent Application No. 05753672.4 in the name of BioArctic Neuroscience AB, dated May 30, 2012 (2 pages).
Declaration of Lars Lannfelt included in submission in European Patent Application No. 05753672.4 in the name of BioArctic Neuroscience AB, dated May 24, 2012 (2 pages).
Communication pursuant to Article 94(3) EPC issued in European Patent Application No. 05753672.4, dated Aug. 21, 2013 (5 pages).
Response to Communication pursuant to Article 94(3) EPC including the First Auxiliary Request and Main Request filed in European Patent Application No. 05753672.4, dated Jan. 27, 2014 (12 pages).
Summons to attend oral proceedings pursuant to Rule 115(1) EPC for European Patent Application No. 05753672.4, dated Mar. 6, 2014 (8 pages).
D1—Kayed et al., "Common structure of soluble amyloid oligomers implies common mechanism of pathogenesis," Science 300(5618):486-489 (2003).
D3—Lashuel et al., "Mixtures of wild-type and a pathogenic (E22G) form of Abeta40 in vitro accumulate protofibrils, including amyloid pores," J Mol Biol. 332(4):795-808 (2003).
D4—Ye et al., "Protofibrils of amyloid beta-protein inhibit specific K+ currents in neocortical cultures," Neurobiol Dis. 13(3):177-190 (2003).
D5—Ward et al., "Fractionation and characterization of oligomeric, protofibrillar and fibrillar forms of beta-amyloid peptide," Biochem. J. 348 Pt 1:137-144 (2000).
Third Party Observations under Article 115 EPC filed in European Application No. 05753672.4, dated Mar. 14, 2014 (4 pages).
Correspondence filed in European Patent Application No. 05753672.4, (referring to Oral Proceedings dated Mar. 6, 2014 including Main Request and First Auxiliary Request), dated Jun. 3, 2014 (24 pages).
Restriction Requirement for U.S. Appl. No. 13/218,592, dated Jan. 27, 2012 (7 pages).
Response to Restriction Requirement for U.S. Appl. No. 13/218,592, dated Jun. 27, 2012 (1 page).
Non-Final Office Action for U.S. Appl. No. 13/218,592, dated Jul. 16, 2012 (18 pages).
Response to Non-Final Office Action for U.S. Appl. No. 13/218,592, dated Oct. 15, 2012 (11 pages).
Supplemental Reply for U.S. Appl. No. 13/218,592, dated Dec. 20, 2012 (4 pages).
Notice of Allowance for U.S. Appl. No. 13/218,592, dated Jan. 22, 2013 (11 pages).
Restriction Requirement for U.S. Appl. No. 11/570,995, mailed Jun. 22, 2009 (7 pages).
Response to Restriction Requirement for U.S. Appl. No. 11/570,995, filed Oct. 16, 2009 (1 page).
Office Communication (Notice of Non-Compliant Amendment) for U.S. Appl. No. 11/570,995, mailed Nov. 27, 2009 (2 pages).

(56) References Cited

OTHER PUBLICATIONS

Response to Office Communication (Notice of Non-Compliant Amendment) for U.S. Appl. No. 11/570,995, filed Feb. 25, 2010 (10 pages).
Non-Final Office Action for U.S. Appl. No. 11/570,995, mailed May 4, 2010 (8 pages).
Response to Non-Final Office Action for U.S. Appl. No. 11/570,995, filed Sep. 30, 2010 (7 pages).
Final Office Action for U.S. Appl. No. 11/570,995, mailed Oct. 19, 2010 (8 pages).
Response to Final Office Action for U.S. Appl. No. 11/570,995, filed Jan. 19, 2011 (16 pages).
Non-Final Office Action for U.S. Appl. No. 11/570,995, mailed Feb. 22, 2011 (14 pages).
Response to Non-Final Office Action for U.S. Appl. No. 11/570,995, filed Jul. 12, 2011 (7 pages).
Notice of Allowance for U.S. Appl. No. 11/570,995, mailed Sep. 23, 2011 (12 pages).
Non-Final Office Action for U.S. Appl. No. 13/336,520, mailed Aug. 7, 2012 (12 pages).
Response to Non-Final Office Action for U.S. Appl. No. 13/336,520, filed Nov. 7, 2012 (5 pages).
Supplemental Amendment for U.S. Appl. No. 13/336,520, filed Dec. 5, 2012 (4 pages).
Notice of Allowance for U.S. Appl. No. 13/336,520, mailed Jan. 14, 2013 (11 pages).
Restriction Requirement for U.S. Appl. No. 13/780,643, mailed Jul. 11, 2013 (7 pages).
Response to Restriction Requirement for U.S. Appl. No. 13/780,643, filed Aug. 12, 2013 (1 page).
Non-Final Office Action for for U.S. Appl. No. 13/780,643, mailed Oct. 15, 2013 (11 pages).
Response to Non-Final Office Action for U.S. Appl. No. 13/780,643, filed Feb. 18, 2014 (4 pages).
Final Office Action for U.S. Appl. No. 13/780,643, mailed Apr. 7, 2014 (7 pages).
Response to Final Office Action for U.S. Appl. No. 13/780,643, filed Jul. 7, 2014 (3 pages).
Notice of Allowance for U.S. Appl. No. 13/780,643, mailed Aug. 4, 2014 (14 pages).
Request for Continued Examination for U.S. Appl. No. 13/780,643, filed Nov. 4, 2014 (1 page).
Notice of Allowance for U.S. Appl. No. 13/780,643, mailed Nov. 21, 2014 (14 pages).
Patent Examination Report No. 1 for Australian Patent Application No. 2010267640, dated Dec. 19, 2013 (4 pages).
Communication pursuant to Article 94(3) EPC for European Patent Application No. 10739701.0, dated Jul. 29, 2014 (6 pages).
Restriction Requirement for U.S. Appl. No. 13/379,523, dated Jan. 22, 2013 (7 pages).
Response to Restriction Requirement for U.S. Appl. No. 13/379,523, dated Feb. 22, 2013 (8 pages).
Non-Final Office Action for U.S. Appl. No. 13/379,523, dated Jul. 3, 2014 (31 pages).
Response to Non-Final Office Action for U.S. Appl. No. 13/379,523, dated Oct. 3, 2014 (25 pages).
English language translation of the Notice of Preliminary Rejection for Japanese Patent Application No. 2012-516964, dated Jul. 22, 2014 (6 pages).
Higuchi, English language translation of "Evaluation of Alzheimer's disease using neuroimaging agents and biological markers," Experimental Medicine, 26:(4 pages) (2008).
Frank, Chapter 4 Specificity and Cross-Reactivity. *Immunology and Evolution of Infectious Disease.* Princeton University Press, (Excerpt) 35-36 (2002).
U.S. Appl. No. 60/621,776, filed Oct. 25, 2004.
U.S. Appl. No. 60/652,538, filed Feb. 14, 2005.
U.S. Appl. No. 60/217,098, filed Jul. 10, 2000.
U.S. Appl. No. 09/745,057, filed Dec. 20, 2000.
U.S. Appl. No. 10/166,856, filed Jun. 11, 2002.
U.S. Appl. No. 09/369,236, filed Aug. 4, 2009.
U.S. Appl. No. 11/570,995, filed Dec. 20, 2006.
U.S. Appl. No. 12/294,207, filed Nov. 23, 2008.
WO 2005/123775A1, pp. 7-8, published Dec. 29, 2005.

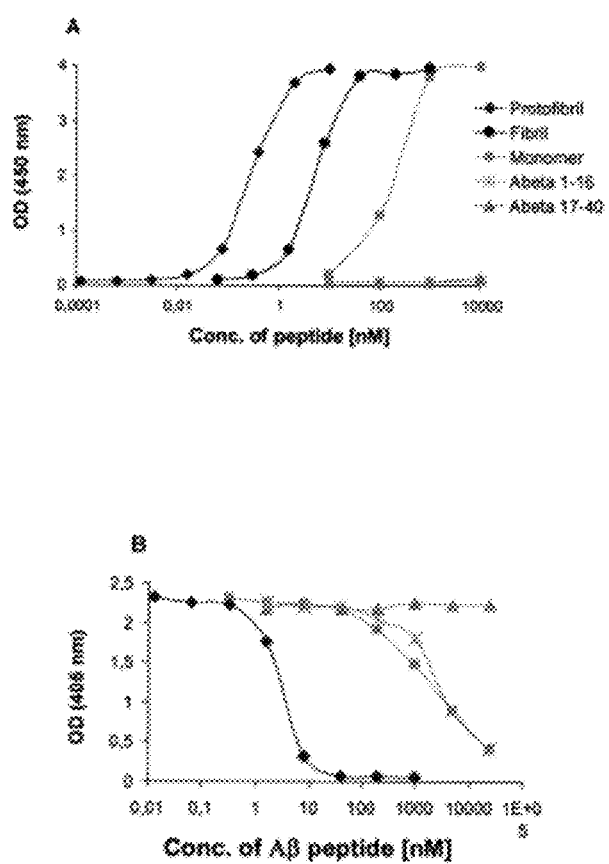
Figure 2: Characterization of a high affinity protofibril selective monoclonal antibody.

Figure 3. Therapeutic efficacy of a high affinity protofibril selective antibody in transgenic mouse model (APPswe)
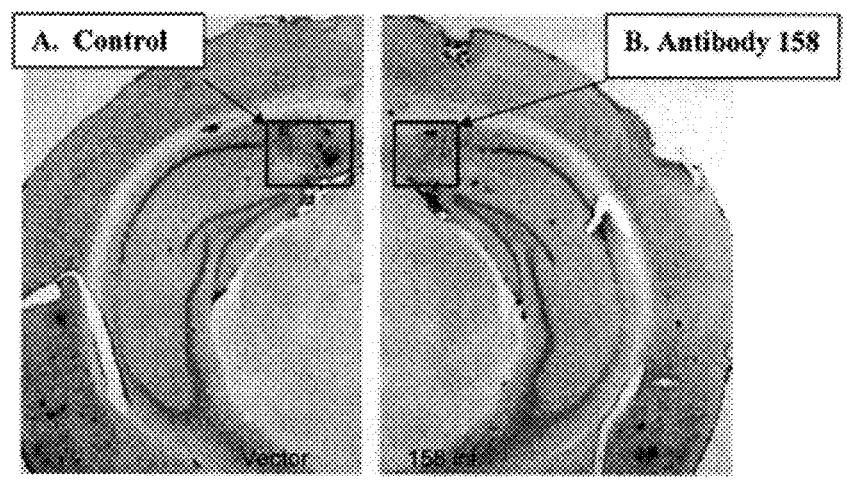
Figure 4
Human Aβ protofibrils are measured at pM levels by proximity ligation technique.
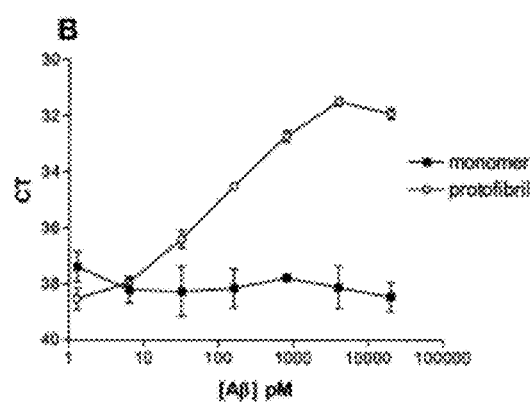

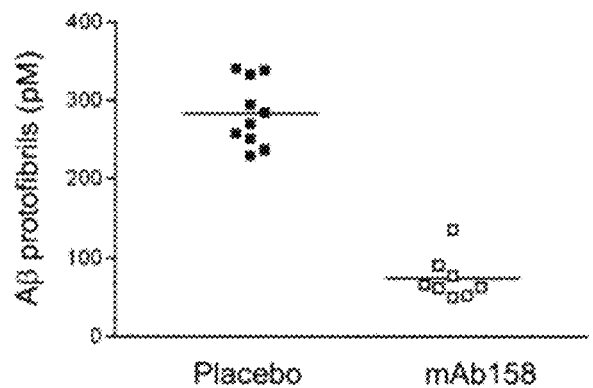
Fig. 8. Aβ protofibril levels in APP_swearc transgenic mouse brain TBS extracts after 4 months treatment with either mAb158 or placebo.
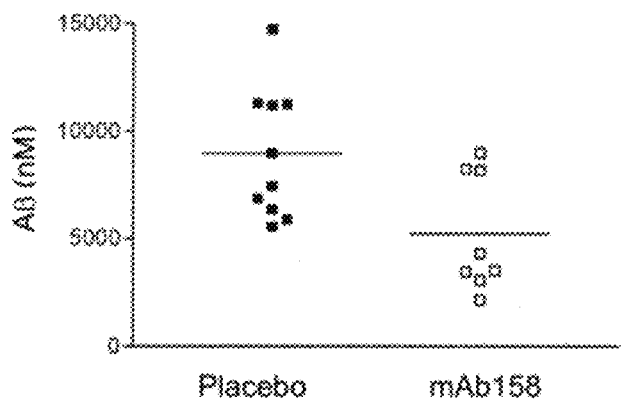
Fig. 9. Total Aβ levels in APP_swearc transgenic mouse brain formic acid extracts after 4 months

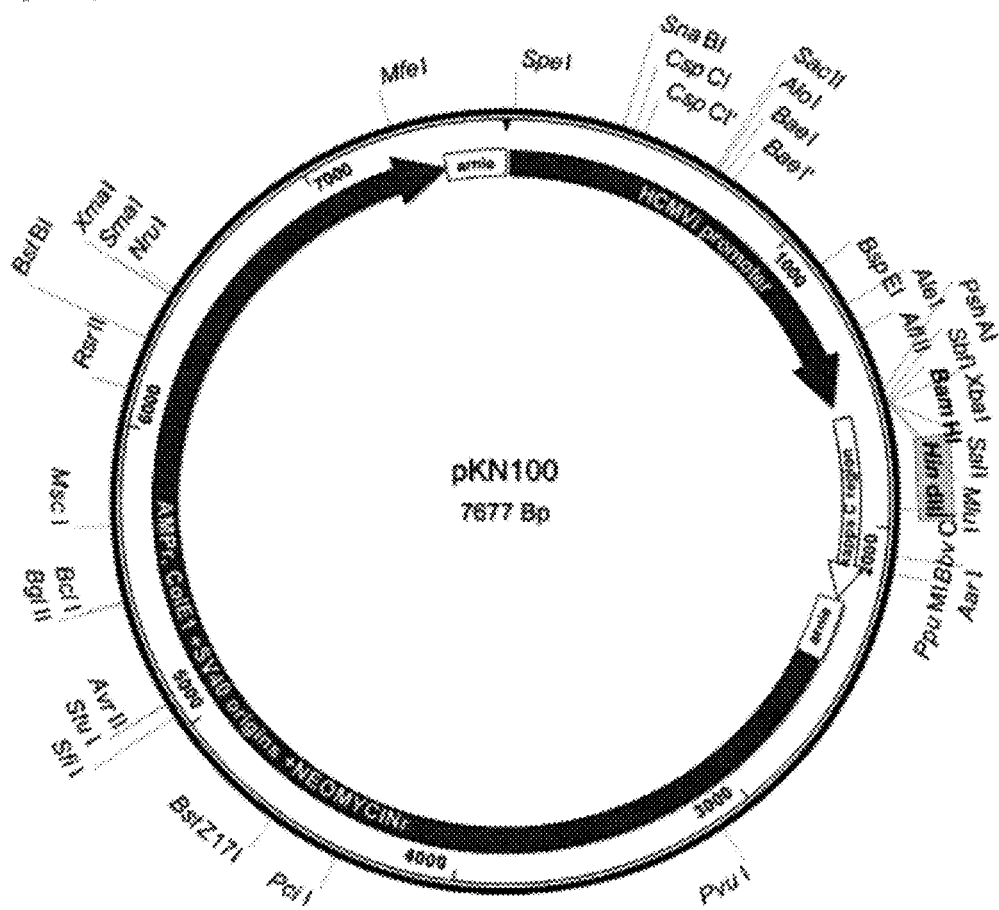
Fig. 10. pKN100 vector

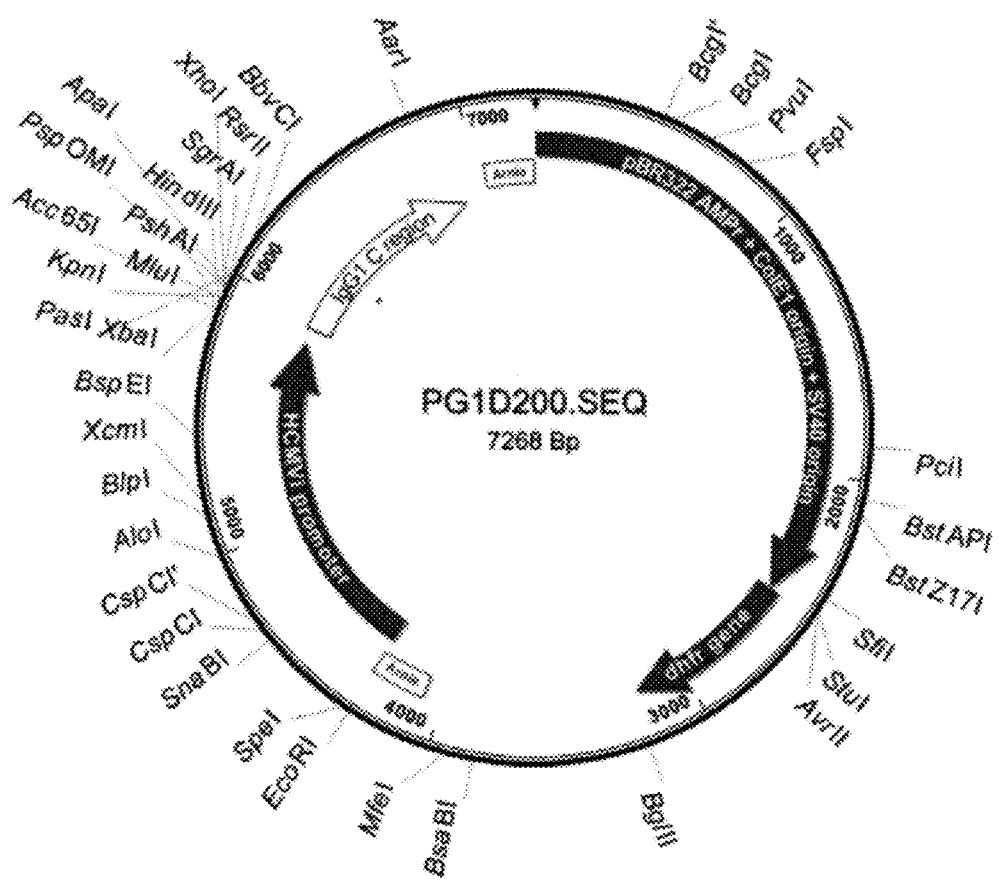
Fig. 11. pG1D200 vector

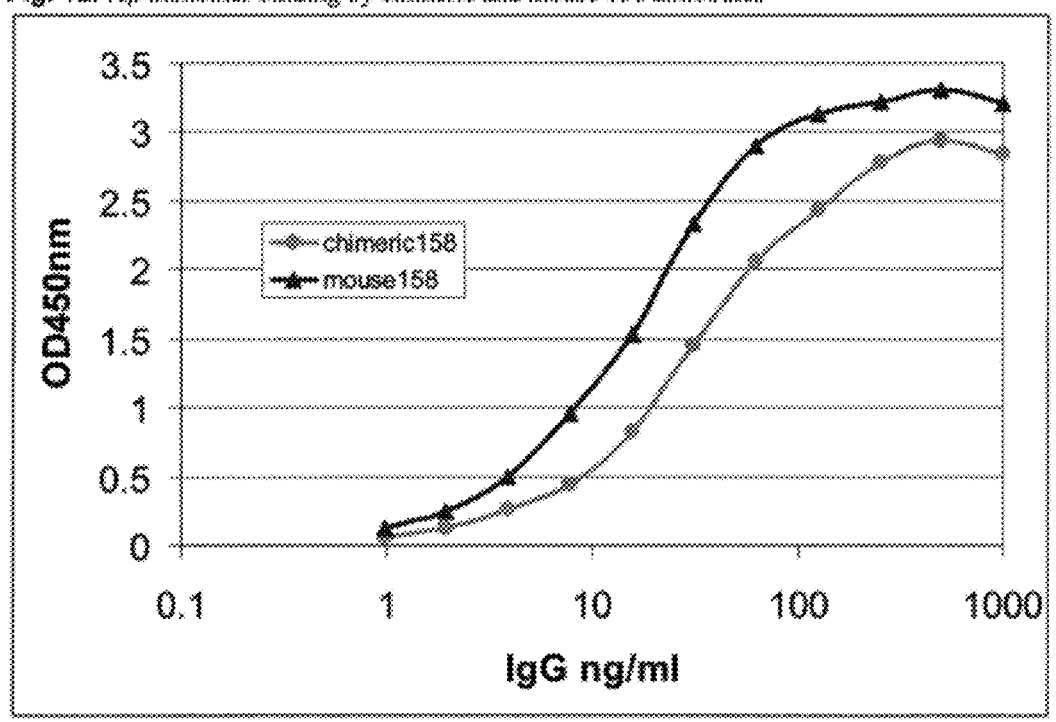
Fig. 12. Aβ monomer binding by chimeric and mouse 158 antibodies
Legend: Direct ELISA coated with Aβ 1-40 (217 ng/well) and using serial dilutions of mAb. Amount of FCS at highest concentration (1 μg/ml) is 2.7%. Detection with anti-mouse k or anti-human k light chain conjugates.

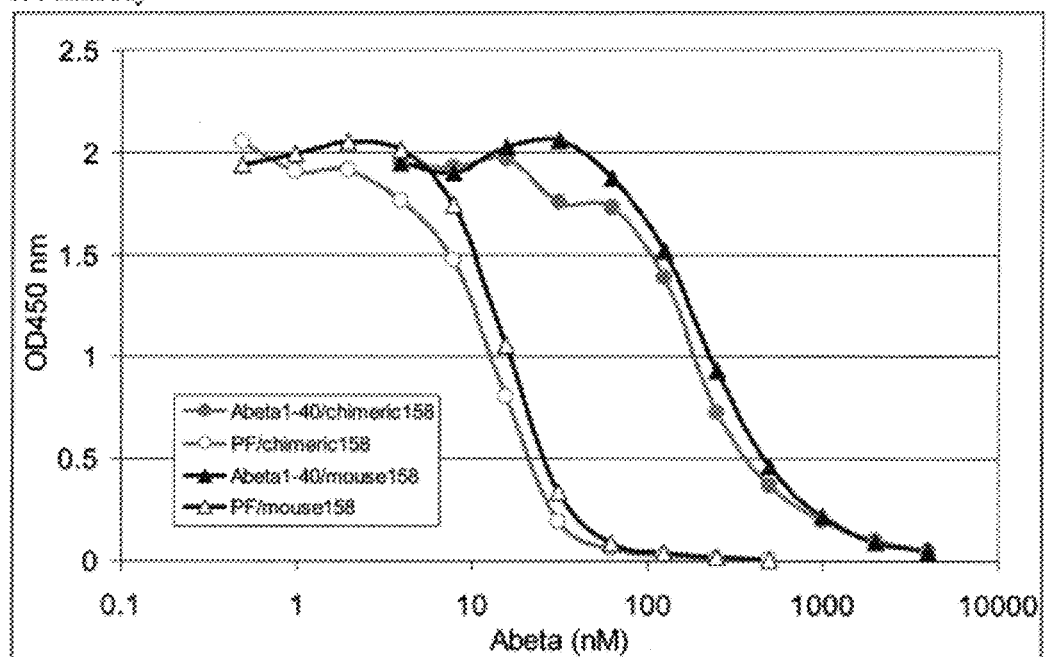

Fig. 13. Competition of monomeric or protofibrillar Aβ for binding to chimeric 158 or mouse 158 antibody Legend: Monomeric Aβ 1-40 (●▲) or protofibrils (PF) (○△) were incubated in solution with chimeric 158 (○●) or mouse 158 (△▲). The final concentration of FCS was 0.3%. After an incubation for 1 h, the mixture was added to a plate coated with Aβ monomers. The binding of antibody to the plate was detected by anti-mouse κ or anti-human κ light chain conjugates.

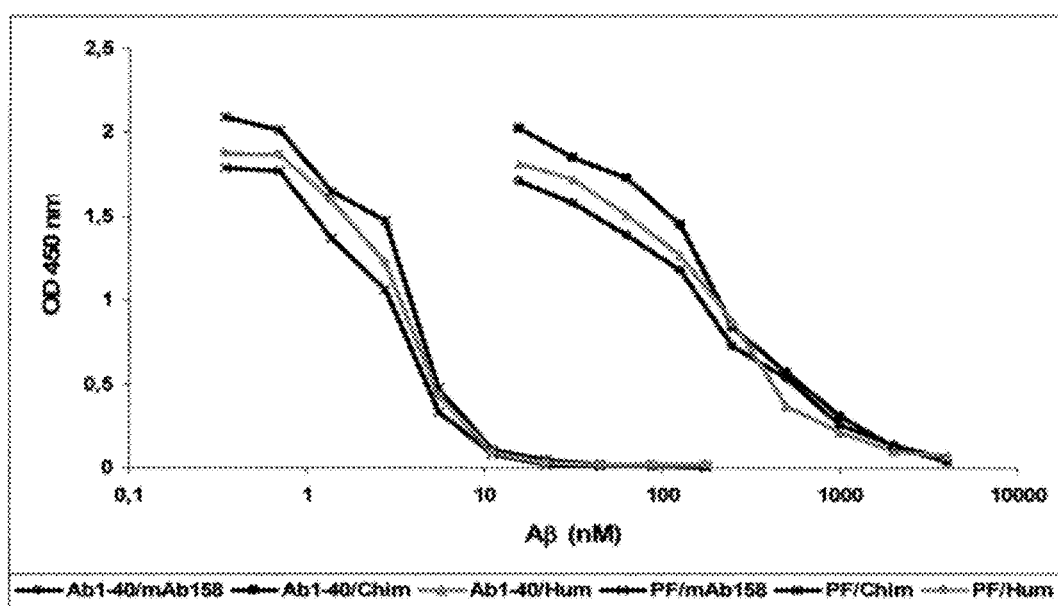

Fig. 14. Competition of monomeric or protofibrillar Aβ for binding to chimeric 158, mouse 158 antibody and humanized 158 antibody (BAN2401).

Legend: Monomeric Aβ 1-40, or protofibrils (PF) were incubated in solution with chimeric 158 antibody (chim), mouse 158 antibody (mAb158) or humanized 158 antibody BAN2401 (Hum). The final concentration of FCS was 0.3%. After an incubation for 1 h, the mixture was added to a plate coated with Aβ monomers. The binding of antibody to the plate was detected by anti-mouse κ or anti-human κ light chain conjugates.

US 9,034,334 B2

SEQUENCE LISTING

```
<160> NUMBER OF SEQ ID NOS: 284

<210> SEQ ID NO 1
<211> LENGTH: 5
<212> TYPE: PRT
<213> ORGANISM: Artificial
<220> FEATURE:
<223> OTHER INFORMATION: Antibody consensus sequence

<400> SEQUENCE: 1

Ser Phe Gly Met His
1               5

<210> SEQ ID NO 2
<211> LENGTH: 17
<212> TYPE: PRT
<213> ORGANISM: Artificial
<220> FEATURE:
<223> OTHER INFORMATION: Antibody consensus sequence

<400> SEQUENCE: 2

Tyr Ile Ser Ser Gly Ser Ser Thr Ile Tyr Tyr Gly Asp Thr Val Lys
1               5                   10                  15

Gly

<210> SEQ ID NO 3
<211> LENGTH: 15
<212> TYPE: PRT
<213> ORGANISM: Artificial
<220> FEATURE:
<223> OTHER INFORMATION: Antibody consensus sequence

<400> SEQUENCE: 3

Glu Gly Gly Tyr Tyr Tyr Gly Arg Ser Tyr Tyr Thr Met Asp Tyr
1               5                   10                  15

<210> SEQ ID NO 4
<211> LENGTH: 16
<212> TYPE: PRT
<213> ORGANISM: Artificial
<220> FEATURE:
<223> OTHER INFORMATION: Antibody consensus sequence

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 7
```

```
<212> TYPE: PRT
<213> ORGANISM: Artificial
<220> FEATURE:
<223> OTHER INFORMATION: Antibody consensus sequence

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial
<220> FEATURE:
<223> OTHER INFORMATION: Antibody consensus region

<400> SEQUENCE: 6

Phe Gln Gly Ser His Val Pro Pro Thr
1               5

<210> SEQ ID NO 7
<211> LENGTH: 16
<212> TYPE: PRT
<213> ORGANISM: Artificial
<220> FEATURE:
<223> OTHER INFORMATION: Antibody consensus sequence

<400> SEQUENCE: 7

Ala Ala Ser Gly Phe Thr Phe Ser Ser Phe Gly Met His Trp Val Arg
1               5                   10                  15

<210> SEQ ID NO 8
<211> LENGTH: 23
<212> TYPE: PRT
<213> ORGANISM: Artificial
<220> FEATURE:
<223> OTHER INFORMATION: Antibody consensus sequence

<400> SEQUENCE: 8

Trp Val Ala Tyr Ile Ser Ser Gly Ser Ser Thr Ile Tyr Tyr Gly Asp
1               5                   10                  15

Thr Val Lys Gly Arg Phe Thr
            20

<210> SEQ ID NO 9
<211> LENGTH: 21
<212> TYPE: PRT
<213> ORGANISM: Artificial
<220> FEATURE:
<223> OTHER INFORMATION: Antibody consensus sequence

<400> SEQUENCE: 9

Cys Ala Arg Glu Gly Gly Tyr Tyr Tyr Gly Arg Ser Tyr Tyr Thr Met
1               5                   10                  15

Asp Tyr Trp Gly Gln
            20

<210> SEQ ID NO 10
<211> LENGTH: 22
<212> TYPE: PRT
<213> ORGANISM: Artificial
<220> FEATURE:
<223> OTHER INFORMATION: Antibody consensus sequence

<400> SEQUENCE: 10

Ile Ser Cys Arg Ser Ser Gln Ser Ile Val His Ser Asn Gly Asn Thr
```

```
                1               5               10              15
Tyr Leu Glu Trp Tyr Leu
                20
```

<210> SEQ ID NO 11
<211> LENGTH: 13
<212> TYPE: PRT
<213> ORGANISM: Artificial
<220> FEATURE:
<223> OTHER INFORMATION: Antibody consensus sequence

<400> SEQUENCE: 11

```
Leu Ile Tyr Lys Val Ser Asn Arg Phe Ser Gly Val Pro
1               5                   10
```

<210> SEQ ID NO 12
<211> LENGTH: 15
<212> TYPE: PRT
<213> ORGANISM: Artificial
<220> FEATURE:
<223> OTHER INFORMATION: Antibody consensus sequence

<400> SEQUENCE: 12

```
Tyr Tyr Cys Phe Gln Gly Ser His Val Pro Pro Thr Phe Gly Gly
1               5                   10                  15
```

<210> SEQ ID NO 13
<211> LENGTH: 117
<212> TYPE: PRT
<213> ORGANISM: Artificial
<220> FEATURE:
<223> OTHER INFORMATION: Antibody variable region

<400> SEQUENCE: 13

```
Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Tyr Tyr Ala Asp Thr Val
        50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Tyr Gly Asn Tyr Ala Met Asp Tyr Trp Gly Gln Gly Thr Ser
            100                 105                 110

Val Thr Val Ser Ser
        115
```

<210> SEQ ID NO 14
<211> LENGTH: 119
<212> TYPE: PRT
<213> ORGANISM: Artificial
<220> FEATURE:
<223> OTHER INFORMATION: Antibody variable region

<400> SEQUENCE: 14

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
```

```
                    20                  25                  30
Ala Met Ser Trp Val Arg Gln Thr Pro Glu Lys Arg Leu Glu Trp Val
                35                  40                  45

Ala Thr Ile Ser Ser Gly Gly Ser Tyr Thr Tyr Tyr Pro Asp Ser Val
            50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Asn Tyr Gly Ser Arg Arg Tyr Phe Asp Val Trp Gly Ala Gly
            100                 105                 110

Thr Ser Val Thr Val Ser Ser
            115

<210> SEQ ID NO 15
<211> LENGTH: 121
<212> TYPE: PRT
<213> ORGANISM: Artificial
<220> FEATURE:
<223> OTHER INFORMATION: Antibody variable region

<400> SEQUENCE: 15

Gln Val His Leu Gln Gln Ser Gly Pro Glu Leu Val Lys Pro Gly Ala
1               5                   10                  15

Ser Val Lys Met Ser Cys Lys Ala Ser Gly Tyr Thr Phe Ile Ser Tyr
                20                  25                  30

Val Met His Trp Val Lys Gln Lys Pro Gly Gln Gly Leu Glu Trp Ile
                35                  40                  45

Gly Tyr Ile Asn Pro Tyr Asn Asp Gly Thr Lys Tyr Asn Glu Lys Phe
            50                  55                  60

Lys Gly Lys Ala Thr Leu Thr Ser Asp Lys Ser Ser Ser Thr Ala Tyr
65                  70                  75                  80

Trp Glu Leu Ser Ser Leu Thr Ser Glu Asp Ser Ala Val Tyr Tyr Cys
                85                  90                  95

Ala Arg Arg Val Ser Pro Leu Thr Ser Tyr Ala Met Asp Tyr Trp Gly
            100                 105                 110

Gln Gly Thr Ser Val Thr Val Ser Ser
            115                 120

<210> SEQ ID NO 16
<211> LENGTH: 119
<212> TYPE: PRT
<213> ORGANISM: Artificial
<220> FEATURE:
<223> OTHER INFORMATION: Antibody variable region

<400> SEQUENCE: 16

Gln Val Gln Leu Lys Glu Ser Gly Pro Gly Leu Val Ala Pro Pro Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Pro Pro Gly Lys Gly Leu Glu Trp Leu
                35                  40                  45

Gly Val Ile Trp Ala Gly Gly Ser Thr Asn Tyr Asn Ser Ala Leu Met
            50                  55                  60

Ser Arg Leu Ser Ile Ser Lys Asp Asn Ser Lys Ser Gln Val Phe Leu
65                  70                  75                  80
```

```
Lys Met Asn Ser Leu Gln Thr Asp Asp Thr Ala Met Tyr Tyr Cys Ala
            85                  90                  95

Arg Gly Arg Tyr Asp Gly Lys Thr Arg Phe Ala Tyr Trp Gly Gln Gly
            100                 105                 110

Thr Leu Val Thr Val Ser Ser
            115

<210> SEQ ID NO 17
<211> LENGTH: 115
<212> TYPE: PRT
<213> ORGANISM: Artificial
<220> FEATURE:
<223> OTHER INFORMATION: Antibody variable region

<400> SEQUENCE: 17

Glu Val Lys Leu Met Glu Ser Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Asp Ser Phe Asp Tyr Trp Gly Gln Gly Thr Thr Leu Thr
            100                 105                 110

Val Ser Ser
        115

<210> SEQ ID NO 18
<211> LENGTH: 124
<212> TYPE: PRT
<213> ORGANISM: Artificial
<220> FEATURE:
<223> OTHER INFORMATION: Antibody variable region

<400> SEQUENCE: 18

Glu Val Gln Arg Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Ser Val Thr Val Ser Ser
        115                 120

<210> SEQ ID NO 19
```

-continued

```
<211> LENGTH: 112
<212> TYPE: PRT
<213> ORGANISM: Artificial
<220> FEATURE:
<223> OTHER INFORMATION: Antibody variable region

<400> SEQUENCE: 19

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Lys Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 20
<211> LENGTH: 107
<212> TYPE: PRT
<213> ORGANISM: Artificial
<220> FEATURE:
<223> OTHER INFORMATION: Antibody variable region

<400> SEQUENCE: 20

Asp Ile Val Met Thr Gln Ala Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Phe
                85                  90                  95

Thr Phe Gly Ser Gly Thr Lys Leu Glu Ile Lys
            100                 105

<210> SEQ ID NO 21
<211> LENGTH: 112
<212> TYPE: PRT
<213> ORGANISM: Artificial
<220> FEATURE:
<223> OTHER INFORMATION: Antibody variable region

<400> SEQUENCE: 21

Asp Ile Val Met Thr Gln Ala Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45
```

```
Ser Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Lys Gln
                85                  90                  95
Ser Tyr Asn Leu Trp Thr Phe Gly Gly Gly Thr Lys Leu Glu Ile Lys
            100                 105                 110
```

<210> SEQ ID NO 22
<211> LENGTH: 108
<212> TYPE: PRT
<213> ORGANISM: Artificial
<220> FEATURE:
<223> OTHER INFORMATION: Antibody variable region

<400> SEQUENCE: 22

```
Glu Asn Val Leu Thr Gln Ser Pro Ala Ile Met Ser Ala Ser Pro Gly
1               5                   10                  15
Glu Lys Val Thr Asn Thr Cys Arg Ala Ser Ser Ser Val Ser Ser Ser
                20                  25                  30
Tyr Leu His Trp Tyr Gln Gln Lys Ser Gly Ala Ser Pro Lys Leu Trp
            35                  40                  45
Ile Tyr Ser Thr Ser Asn Leu Ala Ser Gly Val Pro Ala Arg Phe Ser
    50                  55                  60
Gly Ser Gly Ser Gly Thr Ser Tyr Ser Leu Thr Ile Ser Ser Val Glu
65                  70                  75                  80
Ala Glu Asp Ala Ala Thr Tyr Tyr Cys Gln Gln Tyr Ser Gly Tyr Pro
                85                  90                  95
Leu Thr Phe Gly Ala Gly Thr Lys Leu Glu Leu Lys
            100                 105
```

<210> SEQ ID NO 23
<211> LENGTH: 112
<212> TYPE: PRT
<213> ORGANISM: Artificial
<220> FEATURE:
<223> OTHER INFORMATION: Antibody variable region

<400> SEQUENCE: 23

```
Asp Ile Val Met Thr Gln Ala Pro Leu Ser Leu Pro Val Ser Leu Gly
1               5                   10                  15
Asp Gln Ala Ser Ile Ser Cys Arg Ser Ser Gln Ser Leu Val His Ser
                20                  25                  30
Asn Gly Asn Thr Tyr Leu His Trp Tyr Leu Gln Lys Pro Gly Gln Ser
            35                  40                  45
Leu Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Leu Thr Phe Gly Ala Gly Thr Lys Leu Glu Leu Lys
            100                 105                 110
```

<210> SEQ ID NO 24
<211> LENGTH: 112
<212> TYPE: PRT
<213> ORGANISM: Artificial

```
<220> FEATURE:
<223> OTHER INFORMATION: Antibody variable region

<400> SEQUENCE: 24

Asp Ile Val Met Thr Gln Ala Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 25
<211> LENGTH: 16
<212> TYPE: PRT
<213> ORGANISM: Artificial
<220> FEATURE:
<223> OTHER INFORMATION: Antibody 158 VH CDR1

<400> SEQUENCE: 25

Ala Ala Ser Gly Phe Thr Phe Ser Ser Phe Gly Met His Trp Val Arg
1               5                   10                  15

<210> SEQ ID NO 26
<211> LENGTH: 16
<212> TYPE: PRT
<213> ORGANISM: Artificial
<220> FEATURE:
<223> OTHER INFORMATION: Antibody 158 VH CDR1 (Substitutions)

<400> SEQUENCE: 26

Ala Ala Ser Gly Phe Thr Phe Ser Ser Tyr Ala Met Ser Trp Val Arg
1               5                   10                  15

<210> SEQ ID NO 27
<211> LENGTH: 23
<212> TYPE: PRT
<213> ORGANISM: Artificial
<220> FEATURE:
<223> OTHER INFORMATION: Antibody 158 VH CDR2

<400> SEQUENCE: 27

Trp Val Ala Tyr Ile Ser Ser Gly Ser Ser Thr Ile Tyr Tyr Gly Asp
1               5                   10                  15

Thr Val Lys Gly Arg Phe Thr
            20

<210> SEQ ID NO 28
<211> LENGTH: 23
<212> TYPE: PRT
<213> ORGANISM: Artificial
<220> FEATURE:
<223> OTHER INFORMATION: Antibody 158 VH CDR2 (Substitutions)

<400> SEQUENCE: 28

Trp Val Ala Tyr Ile Ser Ser Gly Ser Ser Thr Ile Tyr Tyr Ala Asp
```

```
1               5                   10                  15
Thr Val Lys Gly Arg Phe Thr
            20

<210> SEQ ID NO 29
<211> LENGTH: 23
<212> TYPE: PRT
<213> ORGANISM: Artificial
<220> FEATURE:
<223> OTHER INFORMATION: Antibody 158 VH CDR2 (Substitutions)

<400> SEQUENCE: 29

Trp Val Ala Thr Ile Ser Ser Gly Gly Ser Tyr Thr Tyr Tyr Pro Asp
1               5                   10                  15
Ser Val Lys Gly Arg Phe Thr
            20

<210> SEQ ID NO 30
<211> LENGTH: 21
<212> TYPE: PRT
<213> ORGANISM: Artificial
<220> FEATURE:
<223> OTHER INFORMATION: Antibody 158 VH CDR3

<400> SEQUENCE: 30

Cys Ala Arg Glu Gly Gly Tyr Tyr Tyr Gly Arg Ser Tyr Tyr Thr Met
1               5                   10                  15
Asp Tyr Trp Gly Gln
            20

<210> SEQ ID NO 31
<211> LENGTH: 14
<212> TYPE: PRT
<213> ORGANISM: Artificial
<220> FEATURE:
<223> OTHER INFORMATION: Antibody 158 VH CDR3 (Substitutions)

<400> SEQUENCE: 31

Cys Ala Arg Tyr Gly Asn Tyr Ala Met Asp Tyr Trp Gly Gln
1               5                   10

<210> SEQ ID NO 32
<211> LENGTH: 16
<212> TYPE: PRT
<213> ORGANISM: Artificial
<220> FEATURE:
<223> OTHER INFORMATION: Antibody 158 VH CDR3 (Substitutions)

<400> SEQUENCE: 32

Cys Ala Arg Asn Tyr Gly Ser Arg Arg Tyr Phe Asp Val Trp Gly Ala
1               5                   10                  15

<210> SEQ ID NO 33
<211> LENGTH: 22
<212> TYPE: PRT
<213> ORGANISM: Artificial
<220> FEATURE:
<223> OTHER INFORMATION: Antibody 158 VL CDR1

<400> SEQUENCE: 33

Ile Ser Cys Arg Ser Ser Gln Ser Ile Val His Ser Asn Gly Asn Thr
1               5                   10                  15
Tyr Leu Glu Trp Tyr Leu
            20
```

```
<210> SEQ ID NO 34
<211> LENGTH: 17
<212> TYPE: PRT
<213> ORGANISM: Artificial
<220> FEATURE:
<223> OTHER INFORMATION: Antibody 158 VL CDR1 (Substitutions)

<400> SEQUENCE: 34

Ile Thr Cys Lys Ala Ser Gln Ser Val Ser Asn Asp Val Ala Trp Tyr
1               5                   10                  15

Gln

<210> SEQ ID NO 35
<211> LENGTH: 13
<212> TYPE: PRT
<213> ORGANISM: Artificial
<220> FEATURE:
<223> OTHER INFORMATION: Antibody 158 VL CDR2

<400> SEQUENCE: 35

Leu Ile Tyr Lys Val Ser Asn Arg Phe Ser Gly Val Pro
1               5                   10

<210> SEQ ID NO 36
<211> LENGTH: 13
<212> TYPE: PRT
<213> ORGANISM: Artificial
<220> FEATURE:
<223> OTHER INFORMATION: Antibody 158 VL CDR2 (Substitutions)

<400> SEQUENCE: 36

Leu Ile Tyr Tyr Ala Ser Asn Arg Tyr Thr Gly Val Pro
1               5                   10

<210> SEQ ID NO 37
<211> LENGTH: 15
<212> TYPE: PRT
<213> ORGANISM: Artificial
<220> FEATURE:
<223> OTHER INFORMATION: Antibody 158 VL CDR3

<400> SEQUENCE: 37

Tyr Tyr Cys Phe Gln Gly Ser His Val Pro Pro Thr Phe Gly Gly
1               5                   10                  15

<210> SEQ ID NO 38
<211> LENGTH: 15
<212> TYPE: PRT
<213> ORGANISM: Artificial
<220> FEATURE:
<223> OTHER INFORMATION: Antibody 158 VL CDR3 (Substitutions)

<400> SEQUENCE: 38

Tyr Phe Cys Gln Gln Asp Tyr Ser Ser Pro Phe Thr Phe Gly Ser
1               5                   10                  15

<210> SEQ ID NO 39
<211> LENGTH: 70
<212> TYPE: PRT
<213> ORGANISM: Mus musculus

<400> SEQUENCE: 39

Asp Ile Val Met Thr Gln Ala Pro Leu Ser Leu Pro Val Ser Leu Gly
1               5                   10                  15

Asp Gln Ala Ser Ile Ser Cys Trp Tyr Leu Gln Lys Pro Gly Gln Ser
```

```
                    20                  25                  30

Pro Lys Leu Leu Ile Tyr Gly Val Pro Asp Arg Phe Ser Gly Ser Gly
            35                  40                  45

Ser Gly Thr Asp Phe Thr Leu Lys Ile Ser Arg Val Glu Ala Glu Asp
        50                  55                  60

Leu Gly Ile Tyr Tyr Cys
65                  70

<210> SEQ ID NO 40
<211> LENGTH: 70
<212> TYPE: PRT
<213> ORGANISM: Mus musculus

<400> SEQUENCE: 40

Asp Ile Val Met Thr Gln Ala Pro Leu Ser Leu Pro Val Ser Leu Gly
1               5                  10                  15

Asp Gln Ala Ser Ile Ser Cys Trp Tyr Leu Gln Lys Pro Gly Gln Ser
                20                  25                  30

Pro Lys Leu Leu Ile Tyr Gly Val Pro Asp Arg Phe Ser Gly Ser Gly
            35                  40                  45

Ser Gly Thr Asp Phe Thr Leu Lys Ile Ser Arg Val Glu Ala Glu Asp
        50                  55                  60

Leu Gly Ile Tyr Tyr Cys
65                  70

<210> SEQ ID NO 41
<211> LENGTH: 70
<212> TYPE: PRT
<213> ORGANISM: Mus musculus

<400> SEQUENCE: 41

Asp Val Val Met Thr Gln Thr Pro Leu Ser Leu Pro Val Ser Leu Gly
1               5                  10                  15

Asp Gln Ala Ser Ile Ser Cys Trp Tyr Leu Gln Lys Pro Gly Gln Ser
                20                  25                  30

Pro Lys Leu Leu Ile Tyr Gly Val Pro Asp Arg Phe Ser Gly Ser Gly
            35                  40                  45

Ser Gly Thr Asp Phe Thr Leu Lys Ile Ser Arg Val Glu Ala Glu Asp
        50                  55                  60

Leu Gly Val Tyr Tyr Cys
65                  70

<210> SEQ ID NO 42
<211> LENGTH: 70
<212> TYPE: PRT
<213> ORGANISM: Mus musculus

<400> SEQUENCE: 42

Asp Ile Val Met Thr Gln Ala Pro Lys Phe Leu Leu Val Ser Ala Gly
1               5                  10                  15

Asp Arg Val Thr Ile Thr Cys Trp Tyr Gln Gln Lys Pro Gly Gln Ser
                20                  25                  30

Pro Lys Leu Leu Ile Tyr Gly Val Pro Asp Arg Phe Thr Gly Ser Gly
            35                  40                  45

Tyr Gly Thr Asp Phe Thr Phe Thr Ile Ser Thr Val Gln Ala Glu Asp
        50                  55                  60

Leu Ala Val Tyr Phe Cys
65                  70
```

```
<210> SEQ ID NO 43
<211> LENGTH: 70
<212> TYPE: PRT
<213> ORGANISM: Homo sapiens

<400> SEQUENCE: 43

Asp Ile Val Met Thr Gln Thr Pro Leu Ser Leu Pro Val Thr Pro Gly
1               5                   10                  15

Glu Pro Ala Ser Ile Ser Cys Trp Tyr Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys
65                  70

<210> SEQ ID NO 44
<211> LENGTH: 70
<212> TYPE: PRT
<213> ORGANISM: Homo sapiens

<400> SEQUENCE: 44

Asp Ile Val Met Thr Gln Ser Pro Leu Ser Leu Pro Val Thr Pro Gly
1               5                   10                  15

Glu Pro Ala Ser Ile Ser Cys Trp Tyr Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys
65                  70

<210> SEQ ID NO 45
<211> LENGTH: 70
<212> TYPE: PRT
<213> ORGANISM: Homo sapiens

<400> SEQUENCE: 45

Asp Ile Val Met Thr Gln Thr Pro Leu Ser Leu Ser Val Thr Pro Gly
1               5                   10                  15

Gln Pro Ala Ser Ile Ser Cys Trp Tyr Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys
65                  70

<210> SEQ ID NO 46
<211> LENGTH: 70
<212> TYPE: PRT
<213> ORGANISM: Homo sapiens

<400> SEQUENCE: 46

Asp Ile Val Met Thr Gln Thr Pro Leu Ser Leu Ser Val Thr Pro Gly
```

```
               1               5                  10                 15
               Gln Pro Ala Ser Ile Ser Cys Trp Tyr Leu Gln Lys Pro Gly Gln Pro
                               20                 25                 30

Pro Gln Leu Leu Ile Tyr Gly Val Pro Asp Arg Phe Ser Gly Ser Gly
                           35                 40                 45

Ser Gly Thr Asp Phe Thr Leu Lys Ile Ser Arg Val Glu Ala Glu Asp
                       50                 55                 60

Val Gly Val Tyr Tyr Cys
               65                  70

<210> SEQ ID NO 47
<211> LENGTH: 70
<212> TYPE: PRT
<213> ORGANISM: Homo sapiens

<400> SEQUENCE: 47

Asp Val Val Met Thr Gln Ser Pro Leu Ser Leu Ser Val Thr Leu Gly
               1               5                  10                 15

Gln Pro Ala Ser Ile Ser Cys Trp Phe Gln Gln Arg Pro Gly Gln Ser
                               20                 25                 30

Pro Arg Arg Leu Ile Tyr Gly Val Pro Asp Arg Phe Ser Gly Ser Gly
                           35                 40                 45

Ser Gly Thr Asp Phe Thr Leu Lys Ile Ser Arg Val Glu Ala Glu Asp
                       50                 55                 60

Val Gly Val Tyr Tyr Cys
               65                  70

<210> SEQ ID NO 48
<211> LENGTH: 71
<212> TYPE: PRT
<213> ORGANISM: Mus musculus

<400> SEQUENCE: 48

Glu Val Lys Leu Met Glu Ser Gly Gly Gly Leu Val Gln Pro Gly Gly
               1               5                  10                 15

Ser Arg Lys Leu Ser Cys Ala Ala Ser Trp Val Arg Gln Ala Pro Glu
                               20                 25                 30

Lys Gly Leu Glu Trp Val Ala Arg Phe Thr Ile Ser Arg Asp Asn Pro
                           35                 40                 45

Lys Asn Thr Leu Phe Leu Gln Met Thr Ser Leu Arg Ser Glu Asp Thr
                       50                 55                 60

Ala Met Tyr Tyr Cys Ala Arg
               65                  70

<210> SEQ ID NO 49
<211> LENGTH: 71
<212> TYPE: PRT
<213> ORGANISM: Mus musculus

<400> SEQUENCE: 49

Glu Val Lys Leu Met Glu Ser Gly Gly Gly Leu Val Gln Pro Gly Gly
               1               5                  10                 15

Ser Arg Lys Leu Ser Cys Ala Ala Ser Trp Val Arg Gln Ala Pro Glu
                               20                 25                 30

Lys Gly Leu Glu Trp Val Ala Arg Phe Thr Ile Ser Arg Asp Asn Pro
                           35                 40                 45

Lys Asn Thr Leu Phe Leu Gln Met Thr Ser Leu Arg Ser Glu Asp Thr
                       50                 55                 60
```

Ala Met Tyr Tyr Cys Ala Arg
65                  70

<210> SEQ ID NO 50
<211> LENGTH: 71
<212> TYPE: PRT
<213> ORGANISM: Mus musculus

<400> SEQUENCE: 50

Glu Val Lys Leu Val Glu Ser Gly Gly Gly Leu Val Gln Pro Gly Gly
1               5                   10                  15

Ser Arg Lys Leu Ser Cys Ala Ala Ser Trp Val Arg Gln Ala Pro Glu
            20                  25                  30

Lys Gly Leu Glu Trp Val Ala Arg Phe Thr Ile Ser Arg Asp Asn Pro
        35                  40                  45

Lys Asn Thr Leu Phe Leu Gln Met Thr Ser Leu Arg Ser Glu Asp Thr
    50                  55                  60

Ala Met Tyr Tyr Cys Ala Arg
65                  70

<210> SEQ ID NO 51
<211> LENGTH: 71
<212> TYPE: PRT
<213> ORGANISM: Mus musculus

<400> SEQUENCE: 51

Glu Val Lys Leu Val Glu Ser Gly Gly Gly Leu Val Lys Pro Gly Gly
1               5                   10                  15

Ser Leu Lys Leu Ser Cys Ala Ala Ser Trp Val Arg Gln Thr Pro Glu
            20                  25                  30

Lys Arg Leu Glu Trp Val Ala Arg Phe Thr Ile Ser Arg Asp Asn Ala
        35                  40                  45

Lys Asn Thr Leu Tyr Leu Gln Met Ser Ser Leu Arg Ser Glu Asp Thr
    50                  55                  60

Ala Met Tyr Tyr Cys Ala Arg
65                  70

<210> SEQ ID NO 52
<211> LENGTH: 71
<212> TYPE: PRT
<213> ORGANISM: Homo sapiens

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Ala Arg Phe Thr Ile Ser Arg Asp Asn Ala
        35                  40                  45

Lys Asn Ser Leu Tyr Leu Gln Met Asn Ser Leu Arg Ala Glu Asp Thr
    50                  55                  60

Ala Val Tyr Tyr Cys Ala Arg
65                  70

<210> SEQ ID NO 53
<211> LENGTH: 71
<212> TYPE: PRT
<213> ORGANISM: Homo sapiens

<400> SEQUENCE: 53

Glu Val Gln Leu Val Glu Ser Gly Gly Gly Leu Ile Gln Pro Gly Gly
1               5                   10                  15

Ser Leu Arg Leu Ser Cys Ala Ala Ser Trp Val Arg Gln Ala Pro Glu
            20                  25                  30

Lys Gly Leu Glu Trp Val Ser Arg Phe Thr Ile Ser Arg Asp Asn Ser
        35                  40                  45

Lys Asn Thr Leu Tyr Leu Gln Met Asn Ser Leu Arg Ala Glu Asp Thr
    50                  55                  60

Ala Val Tyr Tyr Cys Ala Arg
65                  70

<210> SEQ ID NO 54
<211> LENGTH: 71
<212> TYPE: PRT
<213> ORGANISM: Homo sapiens

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Ser Arg Phe Thr Ile Ser Arg Asp Asn Ser
        35                  40                  45

Lys Asn Thr Leu Tyr Leu Gln Met Asn Ser Leu Arg Ala Glu Asp Thr
    50                  55                  60

Ala Val Tyr Tyr Cys Ala Lys
65                  70

<210> SEQ ID NO 55
<211> LENGTH: 71
<212> TYPE: PRT
<213> ORGANISM: Homo sapiens

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Ser Arg Phe Thr Ile Ser Arg Asp Asn Ala
        35                  40                  45

Lys Asn Thr Leu Tyr Leu Gln Met Asn Ser Leu Arg Asp Glu Asp Thr
    50                  55                  60

Ala Val Tyr Tyr Cys Ala Arg
65                  70

<210> SEQ ID NO 56
<211> LENGTH: 71
<212> TYPE: PRT
<213> ORGANISM: Homo sapiens

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Val Trp Val Ser Arg Phe Thr Ile Ser Arg Asp Asn Ala
        35                  40                  45

```
Lys Asn Thr Leu Tyr Leu Gln Met Asn Ser Leu Arg Ala Glu Asp Thr
 50                  55                  60

Ala Val Tyr Tyr Cys Ala Arg
 65                  70
```

<210> SEQ ID NO 57
<211> LENGTH: 30
<212> TYPE: DNA
<213> ORGANISM: Artificial
<220> FEATURE:
<223> OTHER INFORMATION: PCR Primer

<400> SEQUENCE: 57
atgaagttgv vtgttaggct gttggtgctg                           30

<210> SEQ ID NO 58
<211> LENGTH: 30
<212> TYPE: DNA
<213> ORGANISM: Artificial
<220> FEATURE:
<223> OTHER INFORMATION: PCR Primer

<400> SEQUENCE: 58
atggagwcag acacactcct gytatgggtg                           30

<210> SEQ ID NO 59
<211> LENGTH: 30
<212> TYPE: DNA
<213> ORGANISM: Artificial
<220> FEATURE:
<223> OTHER INFORMATION: PCR Primer

<400> SEQUENCE: 59
atgagtgtgc tcactcaggt cctggsgttg                           30

<210> SEQ ID NO 60
<211> LENGTH: 33
<212> TYPE: DNA
<213> ORGANISM: Artificial
<220> FEATURE:
<223> OTHER INFORMATION: PCR Primer

<400> SEQUENCE: 60
atgaggrccc ctgctcagwt tyttggmwtc ttg                       33

<210> SEQ ID NO 61
<211> LENGTH: 29
<212> TYPE: DNA
<213> ORGANISM: Artificial
<220> FEATURE:
<223> OTHER INFORMATION: PCR Primer

<400> SEQUENCE: 61
atggatttwa ggtgcagatt wtcagcttc                            29

<210> SEQ ID NO 62
<211> LENGTH: 27
<212> TYPE: DNA
<213> ORGANISM: Artificial
<220> FEATURE:
<223> OTHER INFORMATION: PCR Primer

<400> SEQUENCE: 62
atgaggtkck ktgktsagst sctgrgg                              27

<210> SEQ ID NO 63
<211> LENGTH: 31
<212> TYPE: DNA
<213> ORGANISM: Artificial
<220> FEATURE:
<223> OTHER INFORMATION: PCR Primer

<400> SEQUENCE: 63
atgggcwtca agatggagtc acakwyycwg g                                31

<210> SEQ ID NO 64
<211> LENGTH: 31
<212> TYPE: DNA
<213> ORGANISM: Artificial
<220> FEATURE:
<223> OTHER INFORMATION: PCR Primer

<400> SEQUENCE: 64 atgtgggay ctktttycmm ttttcaatt g                                  31

<210> SEQ ID NO 65
<211> LENGTH: 25
<212> TYPE: DNA
<213> ORGANISM: Artificial
<220> FEATURE:
<223> OTHER INFORMATION: PCR Primer

<400> SEQUENCE: 65
atggtrtccw casctcagtt ccttg                                       25

<210> SEQ ID NO 66
<211> LENGTH: 27
<212> TYPE: DNA
<213> ORGANISM: Artificial
<220> FEATURE:
<223> OTHER INFORMATION: PCR Primer

<400> SEQUENCE: 66
atgtatatat gtttgttgtc tatttct                                     27

<210> SEQ ID NO 67
<211> LENGTH: 28
<212> TYPE: DNA
<213> ORGANISM: Artificial
<220> FEATURE:
<223> OTHER INFORMATION: PCR Primer

<400> SEQUENCE: 67
atggaagccc cagctcagct tctcttcc                                    28

<210> SEQ ID NO 68
<211> LENGTH: 20
<212> TYPE: DNA
<213> ORGANISM: Artificial
<220> FEATURE:
<223> OTHER INFORMATION: PCR Primer

<400> SEQUENCE: 68
actggatggt gggaagatgg                                             20

<210> SEQ ID NO 69
<211> LENGTH: 27
<212> TYPE: DNA
<213> ORGANISM: Artificial
<220> FEATURE:
<223> OTHER INFORMATION: PCR Primer

```
<400> SEQUENCE: 69
atgaaatgca gctggggcat sttcttc                                    27

<210> SEQ ID NO 70
<211> LENGTH: 26
<212> TYPE: DNA
<213> ORGANISM: Artificial
<220> FEATURE:
<223> OTHER INFORMATION: PCR Primer

<400> SEQUENCE: 70
atgggatgga gctrtatcat sytctt                                     26

<210> SEQ ID NO 71
<211> LENGTH: 27
<212> TYPE: DNA
<213> ORGANISM: Artificial
<220> FEATURE:
<223> OTHER INFORMATION: PCR Primer

<400> SEQUENCE: 71
atgaagwtgt ggttaaactg ggttttt                                    27

<210> SEQ ID NO 72
<211> LENGTH: 25
<212> TYPE: DNA
<213> ORGANISM: Artificial
<220> FEATURE:
<223> OTHER INFORMATION: PCR Primer

<400> SEQUENCE: 72
atgractttg ggytcagctt grttt                                      25

<210> SEQ ID NO 73
<211> LENGTH: 30
<212> TYPE: DNA
<213> ORGANISM: Artificial
<220> FEATURE:
<223> OTHER INFORMATION: PCR Primer

<400> SEQUENCE: 73
atggactcca ggctcaattt agttttcctt                                 30

<210> SEQ ID NO 74
<211> LENGTH: 27
<212> TYPE: DNA
<213> ORGANISM: Artificial
<220> FEATURE:
<223> OTHER INFORMATION: PCR Primer

<400> SEQUENCE: 74
atggctgtcy trgsgctrct cttctgc                                    27

<210> SEQ ID NO 75
<211> LENGTH: 26
<212> TYPE: DNA
<213> ORGANISM: Artificial
<220> FEATURE:
<223> OTHER INFORMATION: PCR Primer

<400> SEQUENCE: 75
atggratgga gckggrtctt tmtctt                                     26

<210> SEQ ID NO 76
```

-continued

```
<211> LENGTH: 23
<212> TYPE: DNA
<213> ORGANISM: Artificial
<220> FEATURE:
<223> OTHER INFORMATION: PCR Primer

<400> SEQUENCE: 76
atgagagtgc tgattctttt gtg                                              23

<210> SEQ ID NO 77
<211> LENGTH: 30
<212> TYPE: DNA
<213> ORGANISM: Artificial
<220> FEATURE:
<223> OTHER INFORMATION: PCR Primer

<400> SEQUENCE: 77
atggmttggg tgtggamctt gctattcctg                                       30

<210> SEQ ID NO 78
<211> LENGTH: 27
<212> TYPE: DNA
<213> ORGANISM: Artificial
<220> FEATURE:
<223> OTHER INFORMATION: PCR Primer

<400> SEQUENCE: 78
atgggcagac ttacattctc attcctg                                          27

<210> SEQ ID NO 79
<211> LENGTH: 28
<212> TYPE: DNA
<213> ORGANISM: Artificial
<220> FEATURE:
<223> OTHER INFORMATION: PCR Primer

<400> SEQUENCE: 79
atggattttg ggctgatttt ttttattg                                         28

<210> SEQ ID NO 80
<211> LENGTH: 27
<212> TYPE: DNA
<213> ORGANISM: Artificial
<220> FEATURE:
<223> OTHER INFORMATION: PCR Primer

<400> SEQUENCE: 80
atgatggtgt taagtcttct gtacctg                                          27

<210> SEQ ID NO 81
<211> LENGTH: 21
<212> TYPE: DNA
<213> ORGANISM: Artificial
<220> FEATURE:
<223> OTHER INFORMATION: PCR Primer

<400> SEQUENCE: 81
cagtggatag acagatgggg g                                                21

<210> SEQ ID NO 82
<211> LENGTH: 21
<212> TYPE: DNA
<213> ORGANISM: Artificial
<220> FEATURE:
<223> OTHER INFORMATION: PCR Primer

<400> SEQUENCE: 82
```

-continued cagtggatag acagatgggg g                                              21

<210> SEQ ID NO 83
<211> LENGTH: 21
<212> TYPE: DNA
<213> ORGANISM: Artificial
<220> FEATURE:
<223> OTHER INFORMATION: PCR Primer

<400> SEQUENCE: 83
cagtggatag actgatgggg g                                              21

<210> SEQ ID NO 84
<211> LENGTH: 21
<212> TYPE: DNA
<213> ORGANISM: Artificial
<220> FEATURE:
<223> OTHER INFORMATION: PCR Primer

<400> SEQUENCE: 84
caagggatag acagatgggg c                                              21

<210> SEQ ID NO 85
<211> LENGTH: 13
<212> TYPE: DNA
<213> ORGANISM: Artificial
<220> FEATURE:
<223> OTHER INFORMATION: Conensus Sequence

<400> SEQUENCE: 85
gccgccrcca ugg                                                       13

<210> SEQ ID NO 86
<211> LENGTH: 8
<212> TYPE: DNA
<213> ORGANISM: Artificial
<220> FEATURE:
<223> OTHER INFORMATION: Consensus Sequence

<400> SEQUENCE: 86 acgtragt                                                              8

<210> SEQ ID NO 87
<211> LENGTH: 9
<212> TYPE: DNA
<213> ORGANISM: Artificial
<220> FEATURE:
<223> OTHER INFORMATION: Consensus Sequence

<400> SEQUENCE: 87 maggtragt                                                             9

<210> SEQ ID NO 88
<211> LENGTH: 16
<212> TYPE: DNA
<213> ORGANISM: Artificial
<220> FEATURE:
<223> OTHER INFORMATION: Consensus Sequence
<220> FEATURE:
<221> NAME/KEY: misc_feature
<222> LOCATION: (12)..(12)
<223> OTHER INFORMATION: n is a, c, g, t or u

<400> SEQUENCE: 88
yyyyyyyyyy yncagg                                                    16

<210> SEQ ID NO 89
<211> LENGTH: 30
<212> TYPE: DNA
<213> ORGANISM: Artificial
<220> FEATURE:
<223> OTHER INFORMATION: PCR Primer

<400> SEQUENCE: 89
aagcttgccg ccaccatgga ctccaggctc                              30

<210> SEQ ID NO 90
<211> LENGTH: 37
<212> TYPE: DNA
<213> ORGANISM: Artificial
<220> FEATURE:
<223> OTHER INFORMATION: PCR Primer

<400> SEQUENCE: 90
gggcccttgg tggaggctga ggagacggtg actgagg                      37

<210> SEQ ID NO 91
<211> LENGTH: 33
<212> TYPE: DNA
<213> ORGANISM: Artificial
<220> FEATURE:
<223> OTHER INFORMATION: PCR Primer

<400> SEQUENCE: 91
aagcttgccg ccaccatgaa gttgcctgtt agg                          33

<210> SEQ ID NO 92
<211> LENGTH: 30
<212> TYPE: DNA
<213> ORGANISM: Artificial
<220> FEATURE:
<223> OTHER INFORMATION: PCR Primer

<400> SEQUENCE: 92
ggatccactc acgtttgatt tccagcttgg                              30

<210> SEQ ID NO 93
<211> LENGTH: 17
<212> TYPE: DNA
<213> ORGANISM: Artificial
<220> FEATURE:
<223> OTHER INFORMATION: PCR Primer

<400> SEQUENCE: 93
gttttcccag tcacgac                                            17

<210> SEQ ID NO 94
<211> LENGTH: 24
<212> TYPE: DNA
<213> ORGANISM: Artificial
<220> FEATURE:
<223> OTHER INFORMATION: PCR Primer

<400> SEQUENCE: 94
agcggataac aatttcacac agga                                    24

<210> SEQ ID NO 95
<211> LENGTH: 17
<212> TYPE: DNA
<213> ORGANISM: Artificial
<220> FEATURE:
<223> OTHER INFORMATION: PCR Primer

<400> SEQUENCE: 95
ctcatcagat ggcggga                                                    17

<210> SEQ ID NO 96
<211> LENGTH: 21
<212> TYPE: DNA
<213> ORGANISM: Artificial
<220> FEATURE:
<223> OTHER INFORMATION: PCR Primer

<400> SEQUENCE: 96
cgctgctgag ggagtagagt c                                               21

<210> SEQ ID NO 97
<211> LENGTH: 400
<212> TYPE: DNA
<213> ORGANISM: Artificial
<220> FEATURE:
<223> OTHER INFORMATION: PCR Template

<400> SEQUENCE: 97
atgaagttgc ctgttaggct gttggtgctg atgttctgga ttcctgcttc cagcagtgat     60
gttttgatga cccaaactcc actctccctg cctgtcagtc ttggagatca agcctccatc    120
tcttgcagat ctagtcagag cattgtacat agtaatggaa acacctattt agaatggtac    180
ctgcagaaac aggccagtc tccaaagctc ctgatctaca agtttccaa ccgatttct      240 ggggtcccag acaggttcag tgcagtgga tcagggacag atttcacact caagatcagc    300
agagtggagg ctgaggatct gggaatttat tactgctttc aaggttcaca tgttcctccg    360
acgttcggtg aggcaccaa gctggaaatc aaacgggctg                           400

<210> SEQ ID NO 98
<211> LENGTH: 30
<212> TYPE: DNA
<213> ORGANISM: Artificial
<220> FEATURE:
<223> OTHER INFORMATION: PCR Primer

<400> SEQUENCE: 98
atgaagttgv vtgttaggct gttggtgctg                                     30

<210> SEQ ID NO 99
<211> LENGTH: 336
<212> TYPE: DNA
<213> ORGANISM: Artificial
<220> FEATURE:
<223> OTHER INFORMATION: PCR Product

<400> SEQUENCE: 99
gatattgtga tgacccaggc tccactctcc ctgcctgtca gtcttggaga tcaagcctcc     60
atctcttgca gatctagtca gagcattgta catagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggaatt tattactgct ttcaaggttc acatgttcct    300
ccgacgttcg gtggaggcac caagctggaa atcaaa                              336

<210> SEQ ID NO 100
<211> LENGTH: 19
<212> TYPE: PRT

```
<213> ORGANISM: Artificial
<220> FEATURE:
<223> OTHER INFORMATION: Chimeric Protein leader sequence

<400> SEQUENCE: 100

Met Lys Leu Pro Val Arg Leu Leu Val Leu Met Phe Trp Ile Pro Ala
1               5                   10                  15

Ser Ser Ser

<210> SEQ ID NO 101
<211> LENGTH: 19
<212> TYPE: PRT
<213> ORGANISM: Artificial
<220> FEATURE:
<223> OTHER INFORMATION: Chimeric protein leader sequence

<400> SEQUENCE: 101

Met Lys Leu Pro Val Arg Leu Leu Val Leu Met Phe Trp Ile Pro Ala
1               5                   10                  15

Ser Ser Ser

<210> SEQ ID NO 102
<211> LENGTH: 57
<212> TYPE: DNA
<213> ORGANISM: Artificial
<220> FEATURE:
<223> OTHER INFORMATION: Chimeric protein DNA sequence

<400> SEQUENCE: 102
atgaagttgc ctgttaggct gttggtgctg atgttctgga ttcctgcttc cagcagt         57

<210> SEQ ID NO 103
<211> LENGTH: 40
<212> TYPE: PRT
<213> ORGANISM: Artificial
<220> FEATURE:
<223> OTHER INFORMATION: Chimeric Protein leader sequence

<400> SEQUENCE: 103

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile
        35                  40

<210> SEQ ID NO 104
<211> LENGTH: 421
<212> TYPE: DNA
<213> ORGANISM: Artificial
<220> FEATURE:
<223> OTHER INFORMATION: Chimeric 158 VK construct DNA sequence

<400> SEQUENCE: 104
aagcttgccg ccaccatgaa gttgcctgtt aggctgttgg tgctgatgtt ctggattcct      60
gcttccagca gtgatgtttt tgatgacccaa actccactct ccctgcctgt cagtcttgga    120
gatgaagcct ccatctcttg cagatctagt cagagcattg tacatagtaa tggaaacacc    180
tatttagaat ggtacctgca gaaaccaggc cagtctccaa agctcctgat ctacaaagtt    240
tccaaccgat tttctggggt cccagacagg ttcagtggca gtggatcagg acagatttc     300 acactcaaga tcagcagagt ggaggctgag gatctgggaa tttattactg ctttcaaggt    360
```

```
tcacatgttc ctccgacgtt cggtggaggc accaagctgg aaatcaaacg tgagtggatc    420
c                                                                    421
```

<210> SEQ ID NO 105
<211> LENGTH: 140
<212> TYPE: PRT
<213> ORGANISM: Artificial
<220> FEATURE:
<223> OTHER INFORMATION: Chimeric 158 VK protein sequence

<400> SEQUENCE: 105

```
Lys Leu Ala Ala Thr Met Lys Leu Pro Val Arg Leu Leu Val Leu Met
1               5                   10                  15

Phe Trp Ile Pro Ala Ser Ser Ser Asp Val Leu Met Thr Gln Thr Pro
            20                  25                  30

Leu Ser Leu Pro Val Ser Leu Gly Asp Gln Ala Ser Ile Ser Cys Arg
        35                  40                  45

Ser Ser Gln Ser Ile Val His Ser Asn Gly Asn Thr Tyr Leu Glu Trp
    50                  55                  60

Tyr Leu Gln Lys Pro Gly Gln Ser Pro Lys Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Ile Tyr Tyr Cys Phe Gln Gly Ser His Val Pro Pro Thr Phe Gly
        115                 120                 125

Gly Gly Thr Lys Leu Glu Ile Lys Arg Glu Trp Ile
    130                 135                 140
```

<210> SEQ ID NO 106
<211> LENGTH: 447
<212> TYPE: DNA
<213> ORGANISM: Artificial
<220> FEATURE:
<223> OTHER INFORMATION: PCR Template

<400> SEQUENCE: 106

```
atggactcca ggctcaattt agttttcctt gtccttattt taaaaggtgt ccagtgtgat    60
gtgcagctgg tggagtctgg gggaggctta gtgcagcctg agggtcccg gaaactctcc    120 tgtgcagcct ctggattcac tttcagtagc tttggaatgc actgggttcg tcaggctcca    180
gagaaggggc tggagtgggt cgcatacatt agtagtggca gtagtaccat ctactatgga    240
gacacagtga agggccgatt caccatctcc agagacaatc caagaacac cctgttcctg    300 caaatgacca gtctaaggtc tgaggacacg gccatgtatt actgtgcaag agaggggga    360 tattactacg gtaggagtta ctatactatg gactactggg gtcaaggaac ctcagtcacc    420
gtctcctcag ccaaaacaac agcccca                                        447
```

<210> SEQ ID NO 107
<211> LENGTH: 390
<212> TYPE: DNA
<213> ORGANISM: Artificial
<220> FEATURE:
<223> OTHER INFORMATION: PCR Product

<400> SEQUENCE: 107

```
gaggtgaagc tgatggaatc tgggggaggc ttagtgcagc ctggagggtc ccggaaactc    60
```

```
tcctgtgcag cctctggatt cactttcagt agctttggaa tgcactgggt tcgtcaggct    120
ccagagaagg ggctggagtg ggtcgcatac attagtagtg gcagtagtac catctactat    180
ggagacacag tgaagggccg attcaccatc tccagagaca atcccaagaa caccctgttc    240
ctgcaaatga ccagtctaag gtctgaggac acggccatgt attactgtgc aagagagggg    300
ggatattact acggtaggag ttactatact atggactact ggggtcaagg aacctcagtc    360
accgtctcct cagccaaaac aacagcccca                                     390
```

```
<210> SEQ ID NO 108
<211> LENGTH: 30
<212> TYPE: DNA
<213> ORGANISM: Artificial
<220> FEATURE:
<223> OTHER INFORMATION: PCR Primer

<400> SEQUENCE: 108
atggactcca ggctcaattt agttttcctt                                     30
```

```
<210> SEQ ID NO 109
<211> LENGTH: 19
<212> TYPE: PRT
<213> ORGANISM: Artificial
<220> FEATURE:
<223> OTHER INFORMATION: 158 VH Leader sequence

<400> SEQUENCE: 109
```

Met Asp Ser Arg Leu Asn Leu Val Phe Leu Val Leu Ile Leu Lys Gly
1               5                   10                  15

Val Gln Cys

```
<210> SEQ ID NO 110
<211> LENGTH: 19
<212> TYPE: PRT
<213> ORGANISM: Artificial
<220> FEATURE:
<223> OTHER INFORMATION: NL-1 protein

<400> SEQUENCE: 110
```

Met Asp Ser Arg Leu Asn Leu Val Phe Leu Val Leu Ile Leu Lys Gly
1               5                   10                  15

Val Gln Cys

```
<210> SEQ ID NO 111
<211> LENGTH: 57
<212> TYPE: DNA
<213> ORGANISM: Artificial
<220> FEATURE:
<223> OTHER INFORMATION: NL-1 DNA

<400> SEQUENCE: 111
atggactcca ggctcaattt agttttcctt gtccttattt taaaaggtgt ccagtgt       57
```

```
<210> SEQ ID NO 112
<211> LENGTH: 30
<212> TYPE: PRT
<213> ORGANISM: Artificial
<220> FEATURE:
<223> OTHER INFORMATION: NL-1 Leader Sequence

<400> SEQUENCE: 112
```

Met Asp Ser Arg Leu Asn Leu Val Phe Leu Val Leu Ile Leu Lys Gly
1               5                   10                  15

```
Val Gln Cys Asp Val Gln Leu Val Glu Ser Gly Gly Gly Leu
         20                  25                  30
```

<210> SEQ ID NO 113
<211> LENGTH: 461
<212> TYPE: DNA
<213> ORGANISM: Artificial
<220> FEATURE:
<223> OTHER INFORMATION: Chimeric 158 VH DNA Sequence

<400> SEQUENCE: 113

```
aagcttgccg ccaccatgga ctccaggctc aatttagttt tccttgtcct tattttaaaa     60
ggtgtccagt gtgatgtgca gctggtggag tctggggag gcttagtgca gcctggaggg    120
tcccggaaac tctcctgtgc agcctctgga ttcactttca gtagctttgg aatgcactgg    180
gttcgtcagg ctccagagaa ggggctggag tgggtcgcat acattagtag tggcagtagt    240
accatctact atggagacac agtgaagggc cgattcacca tctccagaga caatcccaag    300
aacaccctgt tcctgcaaat gaccagtcta aggtctgagg acacggccat gtattactgt    360
gcaagagagg gggatatta ctacggtagg agttactata ctatggacta ctgggtcaa     420
ggaacctcag tcaccgtctc ctcagcctcc accaagggcc c                        461
```

<210> SEQ ID NO 114
<211> LENGTH: 154
<212> TYPE: PRT
<213> ORGANISM: Artificial
<220> FEATURE:
<223> OTHER INFORMATION: Chimeric 158 VH Protein sequence

<400> SEQUENCE: 114

```
Lys Leu Ala Ala Thr Met Asp Ser Arg Leu Asn Leu Val Phe Leu Val
1               5                   10                  15

Leu Ile Leu Lys Gly Val Gln Cys Asp Val Gln Leu Val Glu Ser Gly
            20                  25                  30

Gly Gly Leu Val Gln Pro Gly Gly Ser Arg Lys Leu Ser Cys Ala Ala
        35                  40                  45

Ser Gly Phe Thr Phe Ser Ser Phe Gly Met His Trp Val Arg Gln Ala
    50                  55                  60

Pro Glu Lys Gly Leu Glu Trp Val Ala Tyr Ile Ser Ser Gly Ser Ser
65                  70                  75                  80

Thr Ile Tyr Tyr Gly Asp Thr Val Lys Gly Arg Phe Thr Ile Ser Arg
                85                  90                  95

Asp Asn Pro Lys Asn Thr Leu Phe Leu Gln Met Thr Ser Leu Arg Ser
            100                 105                 110

Glu Asp Thr Ala Met Tyr Tyr Cys Ala Arg Glu Gly Gly Tyr Tyr Tyr
        115                 120                 125

Gly Arg Ser Tyr Tyr Thr Met Asp Tyr Trp Gly Gln Gly Thr Ser Val
    130                 135                 140

Thr Val Ser Ser Ala Ser Thr Lys Gly Pro
145                 150
```

<210> SEQ ID NO 115
<211> LENGTH: 124
<212> TYPE: PRT
<213> ORGANISM: Artificial
<220> FEATURE:
<223> OTHER INFORMATION: 158 VH amino acid sequence

<400> SEQUENCE: 115

Asp Val Gln Leu Val Glu Ser Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Ser Val Thr Val Ser Ser
        115                 120

<210> SEQ ID NO 116
<211> LENGTH: 112
<212> TYPE: PRT
<213> ORGANISM: Artificial
<220> FEATURE:
<223> OTHER INFORMATION: 158 VK amino acid sequence

<400> SEQUENCE: 116

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 117
<211> LENGTH: 22
<212> TYPE: PRT
<213> ORGANISM: Artificial
<220> FEATURE:
<223> OTHER INFORMATION: 158 VH framework

<400> SEQUENCE: 117

Val Ala Gly Phe Thr Phe Ser Val Gln Leu Trp Val Ala Phe Ile Arg
1               5                   10                  15

Asn Leu Tyr Ala Arg Trp
            20

<210> SEQ ID NO 118
<211> LENGTH: 22
<212> TYPE: PRT
<213> ORGANISM: Homo sapiens

<400> SEQUENCE: 118

-continued

Val Ala Gly Phe Thr Phe Ser Val Gln Leu Trp Val Ala Phe Ile Arg
1               5                   10                  15

Asn Leu Tyr Ala Arg Trp
            20

<210> SEQ ID NO 119
<211> LENGTH: 124
<212> TYPE: PRT
<213> ORGANISM: Artificial
<220> FEATURE:
<223> OTHER INFORMATION: 158 VH

<400> SEQUENCE: 119

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Ser Val Thr Val Ser Ser
        115                 120

<210> SEQ ID NO 120
<211> LENGTH: 124
<212> TYPE: PRT
<213> ORGANISM: Homo sapiens

<400> SEQUENCE: 120

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Asp Ser Ser Gly Tyr Tyr Ser Ala Gly Tyr Phe Gln
            100                 105                 110

His Trp Gly Gln Gly Thr Leu Val Thr Val Ser Ser
        115                 120

<210> SEQ ID NO 121
<211> LENGTH: 125
<212> TYPE: PRT
<213> ORGANISM: Homo sapiens

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Gly Glu Lys Phe Tyr Val Asp Ser Val
50                  55                  60

Lys Gly Arg Phe Thr Ile Ser Arg Asp Asn Pro Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Glu Arg Gly His Asp Phe Trp Ser Ile Tyr Tyr Thr His Phe
            100                 105                 110

Asp Tyr Trp Gly Gln Gly Ala Leu Val Thr Val Ser Ser
        115                 120                 125
```

```
<210> SEQ ID NO 122
<211> LENGTH: 118
<212> TYPE: PRT
<213> ORGANISM: Homo sapiens

<400> SEQUENCE: 122

Pro Leu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Trp Met Ser Trp Val Arg Gln Ala Pro Gly Lys Gly Leu Glu Trp
        35                  40                  45

Val Ala Val Ile Trp Tyr Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Gly Gly Ser Ile Phe Asp Tyr Trp Gly Gln Gly Thr
            100                 105                 110

Leu Val Thr Val Ser Ser
        115
```

```
<210> SEQ ID NO 123
<211> LENGTH: 120
<212> TYPE: PRT
<213> ORGANISM: Homo sapiens

<400> SEQUENCE: 123

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Ala Arg Asp Tyr Tyr Tyr Pro Met Asp Val Trp Gly Gln
            100                 105                 110

Gly Thr Thr Val Thr Val Ser Ser
            115                 120

<210> SEQ ID NO 124
<211> LENGTH: 128
<212> TYPE: PRT
<213> ORGANISM: Homo sapiens

<400> SEQUENCE: 124

Gln Val Gln Leu Val Glu Ser Gly Gly Val Val Gln Pro Gly Arg
1               5                   10                  15

Ser Leu Lys Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ser Trp Ser Arg Ile Ala Ala Ala Gly Thr Pro Pro
            100                 105                 110

Ser Leu Phe Asp Pro Trp Gly Gln Gly Thr Leu Val Thr Val Ser Ser
        115                 120                 125

<210> SEQ ID NO 125
<211> LENGTH: 123
<212> TYPE: PRT
<213> ORGANISM: Homo sapiens

<400> SEQUENCE: 125

Gln Val Gln Leu Val Glu Ser Gly Gly Gly Val Val Gln Pro Gly Arg
1               5                   10                  15

Ser Leu Lys Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Asn Tyr Tyr Asp Ser Ser Gly Tyr Ser Phe Asp Tyr
            100                 105                 110

Trp Gly Gln Gly Thr Leu Val Thr Val Ser Ser
        115                 120

<210> SEQ ID NO 126
<211> LENGTH: 117
<212> TYPE: PRT
<213> ORGANISM: Homo sapiens
```

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Arg Arg Gly Ser Gly Asp Ser Trp Gly Gln Gly Thr Leu
            100                 105                 110

Val Thr Val Ser Ser
            115

<210> SEQ ID NO 127
<211> LENGTH: 121
<212> TYPE: PRT
<213> ORGANISM: Homo sapiens

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gln Gln Leu Gly Pro His Asn Trp Phe Asp Pro Trp Gly
            100                 105                 110

Gln Gly Thr Leu Val Thr Val Ser Ser
            115                 120

<210> SEQ ID NO 128
<211> LENGTH: 126
<212> TYPE: PRT
<213> ORGANISM: Homo sapiens

<400> SEQUENCE: 128

Gln Val Gln Leu Val Glu Ser Gly Gly Gly Val Val Gln Pro Gly Arg
1               5                   10                  15

Ser Leu Lys Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Glu Thr Gly Thr Thr Phe Asp Tyr Tyr Tyr Tyr Gly
            100                 105                 110

Met Asp Val Trp Gly Gln Gly Thr Thr Val Thr Val Ser Ser
            115                 120                 125
```

<210> SEQ ID NO 129
<211> LENGTH: 125
<212> TYPE: PRT
<213> ORGANISM: Homo sapiens

<400> SEQUENCE: 129

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Lys Gln Asp Gly Ser Glu Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Met Thr Thr Val Val Lys Pro Ser Leu Ala Thr Asn
            100                 105                 110

Asp Tyr Trp Gly Gln Gly Thr Leu Val Thr Val Ser Ser
            115                 120                 125
```

<210> SEQ ID NO 130
<211> LENGTH: 120
<212> TYPE: PRT
<213> ORGANISM: Homo sapiens

<400> SEQUENCE: 130

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Lys Gln Asp Gly Ser Glu Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Cys Val Gly Ala Leu Gly Ala Phe Asp Ile Trp Gly Gln
            100                 105                 110

Gly Thr Met Val Thr Val Ser Ser
            115                 120
```

<210> SEQ ID NO 131
<211> LENGTH: 116

```
<212> TYPE: PRT
<213> ORGANISM: Homo sapiens

<400> SEQUENCE: 131

Cys Glu Val Gln Leu Val Glu Ser Gly Gly Gly Leu Val Gln Pro Gly
1               5                   10                  15

Gly Ser Leu Arg Leu Ser Cys Ser Ala Ser Gly Phe Thr Phe Ser Thr
                20                  25                  30

Tyr Trp Met Thr Trp Val Arg Gln Ala Pro Gly Lys Gly Leu Glu Trp
                35                  40                  45

Val Ala Asn Ile Lys Pro His Gly Ser Glu Ala Tyr Tyr Val Asp Ser
            50                  55                  60

Val Lys Gly Arg Phe Thr Ile Ser Arg Asp Asn Ala Lys Asn Ser Leu
65                  70                  75                  80

Phe Leu Gln Met Ser Ser Leu Arg Ala Glu Asp Thr Ala Val Tyr Tyr
                85                  90                  95

Cys Ala Arg Ala Asn Ser Leu Asp Val Trp Gly Gln Gly Thr Thr Val
            100                 105                 110

Thr Val Ser Ser
            115

<210> SEQ ID NO 132
<211> LENGTH: 121
<212> TYPE: PRT
<213> ORGANISM: Homo sapiens

<400> SEQUENCE: 132

Cys Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
                20                  25                  30

Tyr Trp Met Ser Trp Val Arg Gln Ala Pro Gly Lys Gly Leu Glu Trp
                35                  40                  45

Val Ala Asn Ile Lys Gln Asp Gly Ser Glu Lys Tyr Tyr Val Asp Ser
            50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Asp Gly Asp Ile Gly Asp Trp Trp Phe Asp Pro Trp Gly
            100                 105                 110

Gln Gly Thr Leu Val Thr Val Ser Ser
            115                 120

<210> SEQ ID NO 133
<211> LENGTH: 132
<212> TYPE: PRT
<213> ORGANISM: Homo sapiens

<400> SEQUENCE: 133

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Ala
```

```
                50                  55                  60
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg Asp Lys Gly Tyr Tyr Asp Tyr Val Trp Gly Ser Tyr Arg Ser
                100                 105                 110

Asn Pro Lys Asn Asp Ala Phe Asp Ile Trp Gly Gln Gly Thr Met Val
            115                 120                 125

Thr Val Ser Ser
        130

<210> SEQ ID NO 134
<211> LENGTH: 132
<212> TYPE: PRT
<213> ORGANISM: Homo sapiens

<400> SEQUENCE: 134

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Ala
         50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg Asp Lys Gly Tyr Tyr Asp Tyr Val Trp Gly Ser Tyr Arg Ser
                100                 105                 110

Asn Pro Lys Asn Asp Ala Phe Asp Ile Trp Gly Gln Gly Thr Met Val
            115                 120                 125

Thr Val Ser Ser
        130

<210> SEQ ID NO 135
<211> LENGTH: 116
<212> TYPE: PRT
<213> ORGANISM: Homo sapiens

<400> SEQUENCE: 135

Gln Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Phe Phe Phe Asp Asn Trp Gly Gln Gly Thr Leu Val
```

Thr Val Ser Ser
115

<210> SEQ ID NO 136
<211> LENGTH: 124
<212> TYPE: PRT
<213> ORGANISM: Artificial
<220> FEATURE:
<223> OTHER INFORMATION: 158 VH

<400> SEQUENCE: 136

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Glu Gly Gly Tyr Tyr Gly Arg Ser Tyr Tyr Thr Met Asp
            100                 105                 110

Tyr Trp Gly Gln Gly Thr Ser Val Thr Val Ser Ser
        115                 120

<210> SEQ ID NO 137
<211> LENGTH: 124
<212> TYPE: PRT
<213> ORGANISM: Homo sapiens

<400> SEQUENCE: 137

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Asp Ser Ser Gly Tyr Tyr Ser Ala Glu Tyr Phe Gln
            100                 105                 110

His Trp Gly Gln Gly Thr Leu Val Thr Val Ser Ser
        115                 120

<210> SEQ ID NO 138
<211> LENGTH: 117
<212> TYPE: PRT
<213> ORGANISM: Homo sapiens

<400> SEQUENCE: 138

Leu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Ser Ile Phe Asp Tyr Trp Gly Gln Gly Thr Leu
            100                 105                 110

Val Thr Val Ser Ser
            115

<210> SEQ ID NO 139
<211> LENGTH: 120
<212> TYPE: PRT
<213> ORGANISM: Homo sapiens

<400> SEQUENCE: 139

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Asp Tyr Tyr Tyr Pro Met Asp Val Trp Gly Gln
            100                 105                 110

Gly Thr Thr Val Thr Val Ser Ser
            115                 120

<210> SEQ ID NO 140
<211> LENGTH: 128
<212> TYPE: PRT
<213> ORGANISM: Homo sapiens

<400> SEQUENCE: 140

Gln Val Gln Leu Val Glu Ser Gly Gly Val Val Gln Pro Gly Arg
1               5                   10                  15

Ser Leu Lys Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Asp Gln Ser Trp Ser Arg Ile Ala Ala Gly Thr Pro Pro
            100                 105                 110

Ser Leu Phe Asp Pro Trp Gly Gln Gly Thr Leu Val Thr Val Ser Ser
        115                 120                 125

<210> SEQ ID NO 141
<211> LENGTH: 123
<212> TYPE: PRT
<213> ORGANISM: Homo sapiens

<400> SEQUENCE: 141

Gln Val Gln Leu Val Glu Ser Gly Gly Gly Val Val Gln Pro Gly Arg
1               5                   10                  15

Ser Leu Lys Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Asn Tyr Tyr Asp Ser Ser Gly Tyr Ser Phe Asp Tyr
            100                 105                 110

Trp Gly Gln Gly Thr Leu Val Thr Val Ser Ser
        115                 120

<210> SEQ ID NO 142
<211> LENGTH: 117
<212> TYPE: PRT
<213> ORGANISM: Homo sapiens

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Arg Arg Gly Ser Gly Asp Ser Trp Gly Gln Gly Thr Leu
            100                 105                 110

Val Thr Val Ser Ser
        115

<210> SEQ ID NO 143
<211> LENGTH: 121
<212> TYPE: PRT
<213> ORGANISM: Homo sapiens -continued

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gln Gln Leu Gly Pro His Asn Trp Phe Asp Pro Trp Gly
            100                 105                 110

Gln Gly Thr Leu Val Thr Val Ser Ser
        115                 120

<210> SEQ ID NO 144
<211> LENGTH: 126
<212> TYPE: PRT
<213> ORGANISM: Homo sapiens

<400> SEQUENCE: 144

Gln Val Gln Leu Val Glu Ser Gly Gly Gly Val Val Gln Pro Gly Arg
1               5                   10                  15

Ser Leu Lys Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Glu Thr Gly Thr Thr Phe Asp Tyr Tyr Tyr Tyr Gly
            100                 105                 110

Met Asp Val Trp Gly Gln Gly Thr Thr Val Thr Val Ser Ser
        115                 120                 125

<210> SEQ ID NO 145
<211> LENGTH: 125
<212> TYPE: PRT
<213> ORGANISM: Homo sapiens

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr

```
              65                  70                  75                  80
Leu Gln Met Asn Ser Leu Arg Ala Glu Asp Thr Ala Val Tyr Tyr Cys
                85                  90                  95

Ala Arg Asp Pro Met Thr Thr Val Val Lys Pro Ser Leu Ala Thr Asn
               100                 105                 110

Asp Tyr Trp Gly Gln Gly Thr Leu Val Thr Val Ser Ser
               115                 120                 125

<210> SEQ ID NO 146
<211> LENGTH: 125
<212> TYPE: PRT
<213> ORGANISM: Homo sapiens

<400> SEQUENCE: 146

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
               20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Met Thr Thr Val Val Lys Pro Ser Leu Ala Thr Asn
               100                 105                 110

Asp Tyr Trp Gly Gln Gly Thr Leu Val Thr Val Ser Ser
               115                 120                 125

<210> SEQ ID NO 147
<211> LENGTH: 115
<212> TYPE: PRT
<213> ORGANISM: Homo sapiens

<400> SEQUENCE: 147

Glu Val Gln Leu Val Glu Ser Gly Gly Gly Leu Val Gln Pro Gly Gly
1               5                  10                  15

Ser Leu Arg Leu Ser Cys Ser Ala Ser Gly Phe Thr Phe Ser Thr Tyr
               20                  25                  30

Trp Met Thr Trp Val Arg Gln Ala Pro Gly Lys Gly Leu Glu Trp Val
            35                  40                  45

Ala Asn Ile Lys Pro His Gly Ser Glu Ala Tyr Tyr Val Asp Ser Val
        50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Ala Asn Ser Leu Asp Val Trp Gly Gln Gly Thr Thr Val Thr
               100                 105                 110

Val Ser Ser
       115

<210> SEQ ID NO 148
<211> LENGTH: 98
<212> TYPE: PRT
```

```
<213> ORGANISM: Artificial
<220> FEATURE:
<223> OTHER INFORMATION: 158 VH

<400> SEQUENCE: 148

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg

<210> SEQ ID NO 149
<211> LENGTH: 98
<212> TYPE: PRT
<213> ORGANISM: Homo sapiens

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Trp Met Thr Trp Val Arg Gln Ala Pro Gly Lys Gly Leu Glu Trp Val
        35                  40                  45

Ala Asn Ile Lys Pro His Gly Ser Glu Ala Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg

<210> SEQ ID NO 150
<211> LENGTH: 98
<212> TYPE: PRT
<213> ORGANISM: Homo sapiens

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

-continued

Ala Arg

<210> SEQ ID NO 151
<211> LENGTH: 57
<212> TYPE: DNA
<213> ORGANISM: Homo sapiens

<400> SEQUENCE: 151
atggaattgg ggctgagctg ggttttcctt gttgctattt tagaaggtgt ccagtgt          57

<210> SEQ ID NO 152
<211> LENGTH: 19
<212> TYPE: PRT
<213> ORGANISM: Homo sapiens

<400> SEQUENCE: 152

Met Glu Leu Gly Leu Ser Trp Val Phe Leu Val Ala Ile Leu Glu Gly
1               5                   10                  15

Val Gln Cys

<210> SEQ ID NO 153
<211> LENGTH: 44
<212> TYPE: PRT
<213> ORGANISM: Homo sapiens

<400> SEQUENCE: 153

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ser Ala Ser
        35                  40

<210> SEQ ID NO 154
<211> LENGTH: 124
<212> TYPE: PRT
<213> ORGANISM: Artificial
<220> FEATURE:
<223> OTHER INFORMATION: 158 VH

<400> SEQUENCE: 154

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Ser Val Thr Val Ser Ser
        115                 120

<210> SEQ ID NO 155

```
<211> LENGTH: 5
<212> TYPE: PRT
<213> ORGANISM: Artificial
<220> FEATURE:
<223> OTHER INFORMATION: 158 VH CDR1

<400> SEQUENCE: 155

Ser Phe Gly Met His
1               5

<210> SEQ ID NO 156
<211> LENGTH: 17
<212> TYPE: PRT
<213> ORGANISM: Artificial
<220> FEATURE:
<223> OTHER INFORMATION: 158 VH CDR2

<400> SEQUENCE: 156

Tyr Ile Ser Ser Gly Ser Ser Thr Ile Tyr Tyr Gly Asp Thr Val Lys
1               5                   10                  15

Gly

<210> SEQ ID NO 157
<211> LENGTH: 15
<212> TYPE: PRT
<213> ORGANISM: Artificial
<220> FEATURE:
<223> OTHER INFORMATION: 158 VH CDR3

<400> SEQUENCE: 157

Glu Gly Gly Tyr Tyr Tyr Gly Arg Ser Tyr Tyr Thr Met Asp Tyr
1               5                   10                  15

<210> SEQ ID NO 158
<211> LENGTH: 123
<212> TYPE: PRT
<213> ORGANISM: Artificial
<220> FEATURE:
<223> OTHER INFORMATION: 158RHA

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser
        115                 120

<210> SEQ ID NO 159
<211> LENGTH: 30
<212> TYPE: PRT
<213> ORGANISM: Artificial
<220> FEATURE:
```

<223> OTHER INFORMATION: AF062243 FW1

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser
            20                  25                  30

<210> SEQ ID NO 160
<211> LENGTH: 14
<212> TYPE: PRT
<213> ORGANISM: Artificial
<220> FEATURE:
<223> OTHER INFORMATION: AF062243 FW2

<400> SEQUENCE: 160

Trp Val Arg Gln Ala Pro Gly Lys Gly Leu Glu Trp Val Ala
1               5                   10

<210> SEQ ID NO 161
<211> LENGTH: 32
<212> TYPE: PRT
<213> ORGANISM: Artificial
<220> FEATURE:
<223> OTHER INFORMATION: AF062243 FW3

<400> SEQUENCE: 161

Arg Phe Thr Ile Ser Arg Asp Asn Ala Lys Asn Ser Leu Phe Leu Gln
1               5                   10                  15

Met Ser Ser Leu Arg Ala Glu Asp Thr Ala Val Tyr Tyr Cys Ala Arg
            20                  25                  30

<210> SEQ ID NO 162
<211> LENGTH: 10
<212> TYPE: PRT
<213> ORGANISM: Artificial
<220> FEATURE:
<223> OTHER INFORMATION: AF062243 FW4

<400> SEQUENCE: 162

Trp Gly Gln Gly Thr Thr Val Thr Val Ser
1               5                   10

<210> SEQ ID NO 163
<211> LENGTH: 116
<212> TYPE: PRT
<213> ORGANISM: Artificial
<220> FEATURE:
<223> OTHER INFORMATION: AF062243

<400> SEQUENCE: 163

Cys Glu Val Gln Leu Val Glu Ser Gly Gly Gly Leu Val Gln Pro Gly
1               5                   10                  15

Gly Ser Leu Arg Leu Ser Cys Ser Ala Ser Gly Phe Thr Phe Ser Thr
            20                  25                  30

Tyr Trp Met Thr Trp Val Arg Gln Ala Pro Gly Lys Gly Leu Glu Trp
        35                  40                  45

Val Ala Asn Ile Lys Pro His Gly Ser Glu Ala Tyr Tyr Val Asp Ser
    50                  55                  60

Val Lys Gly Arg Phe Thr Ile Ser Arg Asp Asn Ala Lys Asn Ser Leu
65                  70                  75                  80

Phe Leu Gln Met Ser Ser Leu Arg Ala Glu Asp Thr Ala Val Tyr Tyr
                85                  90                  95

```
Cys Ala Arg Ala Asn Ser Leu Asp Val Trp Gly Gln Gly Thr Thr Val
              100                 105                 110

Thr Val Ser Ser
        115

<210> SEQ ID NO 164
<211> LENGTH: 57
<212> TYPE: DNA
<213> ORGANISM: Artificial
<220> FEATURE:
<223> OTHER INFORMATION: VH3-07 leader

<400> SEQUENCE: 164
atggaattgg ggctgagctg ggttttcctt gttgctattt tagaaggtgt ccagtgt        57

<210> SEQ ID NO 165
<211> LENGTH: 19
<212> TYPE: PRT
<213> ORGANISM: Artificial
<220> FEATURE:
<223> OTHER INFORMATION: VH3-07 leader

<400> SEQUENCE: 165

Met Glu Leu Gly Leu Ser Trp Val Phe Leu Val Ala Ile Leu Glu Gly
1               5                   10                  15

Val Gln Cys

<210> SEQ ID NO 166
<211> LENGTH: 90
<212> TYPE: DNA
<213> ORGANISM: Artificial
<220> FEATURE:
<223> OTHER INFORMATION: AF062243 FW1

<400> SEQUENCE: 166
gaggtgcagc tggtggagtc tgggggaggc ttggtccagc ctgggggtc cctgagactc        60 tcctgttcag cctctggatt cacctttagt                                       90

<210> SEQ ID NO 167
<211> LENGTH: 15
<212> TYPE: DNA
<213> ORGANISM: Artificial
<220> FEATURE:
<223> OTHER INFORMATION: 158 CDR1

<400> SEQUENCE: 167
agctttggaa tgcac                                                       15

<210> SEQ ID NO 168
<211> LENGTH: 42
<212> TYPE: DNA
<213> ORGANISM: Artificial
<220> FEATURE:
<223> OTHER INFORMATION: AF062243 FW2

<400> SEQUENCE: 168
tgggtccgcc aggctccagg gaaggggctg gagtgggtgg cc                         42

<210> SEQ ID NO 169
<211> LENGTH: 51
<212> TYPE: DNA
<213> ORGANISM: Artificial
<220> FEATURE:
<223> OTHER INFORMATION: 158 CDR2
```

<400> SEQUENCE: 169
tacattagta gtggcagtag taccatctac tatggagaca cagtgaaggg c                51

<210> SEQ ID NO 170
<211> LENGTH: 96
<212> TYPE: DNA
<213> ORGANISM: Artificial
<220> FEATURE:
<223> OTHER INFORMATION: AF062243 FW3

<400> SEQUENCE: 170
cgattcacca tctccagaga caacgccaag aactcactgt ttctgcaaat gagcagcctg        60
agagccgagg acacggccgt gtattattgt gcgaga                                  96

<210> SEQ ID NO 171
<211> LENGTH: 45
<212> TYPE: DNA
<213> ORGANISM: Artificial
<220> FEATURE:
<223> OTHER INFORMATION: 158 CDR3

<400> SEQUENCE: 171 gagggggat attactacgg taggagttac tatactatgg actac                         45

<210> SEQ ID NO 172
<211> LENGTH: 30
<212> TYPE: DNA
<213> ORGANISM: Artificial
<220> FEATURE:
<223> OTHER INFORMATION: AF062243 FW4

<400> SEQUENCE: 172
tggggccaag ggaccacggt caccgtctcc                                         30

<210> SEQ ID NO 173
<211> LENGTH: 426
<212> TYPE: DNA
<213> ORGANISM: Artificial
<220> FEATURE:
<223> OTHER INFORMATION: 158RHAss DNA sequence

<400> SEQUENCE: 173
atggaattgg ggctgagctg ggttttcctt gttgctattt tagaaggtgt ccagtgtgag        60
gtgcagctgg tggagtctgg gggaggcttg gtccagcctg gggggtccct gagactctcc       120
tgttcagcct ctggattcac ctttagtagc tttggaatgc actgggtccg ccaggctcca       180
gggaaggggc tggagtgggt ggcctacatt agtagtggca gtagtaccat ctactatgga       240
gacacagtga aggccgatt caccatctcc agagacaacg ccaagaactc actgtttctg       300
caaatgagca gcctgagagc cgaggacacg gccgtgtatt attgtgcgag agagggggga       360
tattactacg gtaggagtta ctatactatg gactactggg gccaaggac cacggtcacc       420 gtctcc                                                                  426

<210> SEQ ID NO 174
<211> LENGTH: 142
<212> TYPE: PRT
<213> ORGANISM: Artificial
<220> FEATURE:
<223> OTHER INFORMATION: 158RHAss protein sequence

<400> SEQUENCE: 174

```
Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ser Ala Ser Gly Phe Thr Phe
                35                  40                  45

Ser Ser Phe Gly Met His Trp Val Arg Gln Ala Pro Gly Lys Gly Leu
    50                  55                  60

Glu Trp Val Ala Tyr Ile Ser Ser Gly Ser Ser Thr Ile Tyr Tyr Gly
65                  70                  75                  80

Asp Thr Val Lys Gly Arg Phe Thr Ile Ser Arg Asp Asn Ala Lys Asn
                85                  90                  95

Ser Leu Phe Leu Gln Met Ser Ser Leu Arg Ala Glu Asp Thr Ala Val
                100                 105                 110

Tyr Tyr Cys Ala Arg Glu Gly Gly Tyr Tyr Tyr Gly Arg Ser Tyr Tyr
            115                 120                 125

Thr Met Asp Tyr Trp Gly Gln Gly Thr Thr Val Thr Val Ser
    130                 135                 140
```

<210> SEQ ID NO 175
<211> LENGTH: 426
<212> TYPE: DNA
<213> ORGANISM: Artificial
<220> FEATURE:
<223> OTHER INFORMATION: 158RHA

<400> SEQUENCE: 175

```
atggaattgg ggctgagctg ggttttcctt gttgctattt tagagggagt ccagtgcgaa    60
gtgcagctgg tggagtctgg gggaggcttg gtccagcctg ggggtccct gagactctcc    120
tgttcagcct ctggattcac ctttagtagc tttggaatgc actgggtccg ccaggctcca    180
gggaaggggc tggaatgggt ggcctacatt agtagtggca gtagtaccat ctactatgga    240
gacaccgtga agggccgatt caccatctcc agagacaacg ccaagaactc actgtttctg    300
caaatgagca gcctgagagc cgaggacacg gccgtgtatt attgtgcgag agaggggga    360
tattactacg gaaggagtta ctatactatg gactactggg gccaagggac cacggtcacc    420
gtctcc                                                              426
```

<210> SEQ ID NO 176
<211> LENGTH: 426
<212> TYPE: DNA
<213> ORGANISM: Artificial
<220> FEATURE:
<223> OTHER INFORMATION: 158RHAss

<400> SEQUENCE: 176

```
atggaattgg ggctgagctg ggttttcctt gttgctattt tagaaggtgt ccagtgtgag    60
gtgcagctgg tggagtctgg gggaggcttg gtccagcctg ggggtccct gagactctcc    120
tgttcagcct ctggattcac ctttagtagc tttggaatgc actgggtccg ccaggctcca    180
gggaaggggc tggagtgggt ggcctacatt agtagtggca gtagtaccat ctactatgga    240
gacacagtga agggccgatt caccatctcc agagacaacg ccaagaactc actgtttctg    300
caaatgagca gcctgagagc cgaggacacg gccgtgtatt attgtgcgag agaggggga    360
tattactacg gtaggagtta ctatactatg gactactggg gccaagggac cacggtcacc    420
gtctcc                                                              426
```

<210> SEQ ID NO 177
<211> LENGTH: 426
<212> TYPE: DNA
<213> ORGANISM: Artificial
<220> FEATURE:
<223> OTHER INFORMATION: 158RHA DNA sequence

<400> SEQUENCE: 177

```
atggaattgg ggctgagctg ggttttcctt gttgctattt tagagggagt ccagtgcgaa      60
gtgcagctgg tggagtctgg gggaggcttg gtccagcctg ggggtccct gagactctcc      120
tgttcagcct ctggattcac ctttagtagc tttggaatgc actgggtccg ccaggctcca     180
gggaagggc tggaatgggt ggcctacatt agtagtggca gtagtaccat ctactatgga     240
gacaccgtga agggccgatt caccatctcc agagacaacg ccaagaactc actgtttctg     300
caaatgagca gcctgagagc cgaggacacg gccgtgtatt attgtgcgag agagggggga     360
tattactacg gaaggagtta ctatactatg gactactggg ccaagggac cacggtcacc     420
gtctcc                                                                426
```

<210> SEQ ID NO 178
<211> LENGTH: 142
<212> TYPE: PRT
<213> ORGANISM: Artificial
<220> FEATURE:
<223> OTHER INFORMATION: 158RHA Protein sequence

<400> SEQUENCE: 178

```
Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ser Ala Ser Gly Phe Thr Phe
        35                  40                  45

Ser Ser Phe Gly Met His Trp Val Arg Gln Ala Pro Gly Lys Gly Leu
    50                  55                  60

Glu Trp Val Ala Tyr Ile Ser Ser Gly Ser Ser Thr Ile Tyr Tyr Gly
65                  70                  75                  80

Asp Thr Val Lys Gly Arg Phe Thr Ile Ser Arg Asp Asn Ala Lys Asn
                85                  90                  95

Ser Leu Phe Leu Gln Met Ser Ser Leu Arg Ala Glu Asp Thr Ala Val
            100                 105                 110

Tyr Tyr Cys Ala Arg Glu Gly Gly Tyr Tyr Gly Arg Ser Tyr Tyr
        115                 120                 125

Thr Met Asp Tyr Trp Gly Gln Gly Thr Thr Val Thr Val Ser
    130                 135                 140
```

<210> SEQ ID NO 179
<211> LENGTH: 17
<212> TYPE: PRT
<213> ORGANISM: Artificial
<220> FEATURE:
<223> OTHER INFORMATION: 158 VK

<400> SEQUENCE: 179

```
Val Met Trp Tyr Gln Pro Leu Leu Ile Tyr Gly Gly Gly Thr Phe Tyr
1               5                   10                  15

Phe
```

```
<210> SEQ ID NO 180
<211> LENGTH: 17
<212> TYPE: PRT
<213> ORGANISM: Homo sapiens

<400> SEQUENCE: 180

Val Met Trp Tyr Gln Pro Leu Leu Ile Tyr Gly Gly Gly Thr Phe Tyr
1               5                   10                  15
Phe

<210> SEQ ID NO 181
<211> LENGTH: 17
<212> TYPE: PRT
<213> ORGANISM: Homo sapiens

<400> SEQUENCE: 181

Ile Met Trp Tyr Gln Pro Leu Leu Ile Tyr Gly Gly Gly Thr Phe Tyr
1               5                   10                  15
Phe

<210> SEQ ID NO 182
<211> LENGTH: 17
<212> TYPE: PRT
<213> ORGANISM: Homo sapiens

<400> SEQUENCE: 182

Val Met Trp Tyr Gln Pro Leu Leu Val Tyr Gly Gly Gly Thr Phe Tyr
1               5                   10                  15
Phe

<210> SEQ ID NO 183
<211> LENGTH: 112
<212> TYPE: PRT
<213> ORGANISM: Artificial
<220> FEATURE:
<223> OTHER INFORMATION: 158 VK

<400> SEQUENCE: 183

Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 184
<211> LENGTH: 112
<212> TYPE: PRT
<213> ORGANISM: Homo sapiens

<400> SEQUENCE: 184

Asp Val Val Met Thr Gln Ser Pro Leu Ser Leu Pro Val Thr Pro Gly
1               5                   10                  15
```

```
Ala Pro Ala Ser Ile Ser Cys Arg Ser Ser Gln Ser Leu Leu His Thr
            20                  25                  30

Asn Gly Val Asn Phe Leu Asp Trp Tyr Leu Gln Lys Pro Gly Gln Ser
        35                  40                  45

Pro Lys Leu Leu Ile Tyr Leu Ala Ser His Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Gly
                85                  90                  95

Leu Gln Thr Pro Phe Thr Phe Gly Pro Gly Thr Lys Leu Glu Ile Lys
            100                 105                 110

<210> SEQ ID NO 185
<211> LENGTH: 112
<212> TYPE: PRT
<213> ORGANISM: Homo sapiens

<400> SEQUENCE: 185

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 186
<211> LENGTH: 112
<212> TYPE: PRT
<213> ORGANISM: Homo sapiens

<400> SEQUENCE: 186

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 187
```

```
<211> LENGTH: 112
<212> TYPE: PRT
<213> ORGANISM: Homo sapiens

<400> SEQUENCE: 187

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 188
<211> LENGTH: 112
<212> TYPE: PRT
<213> ORGANISM: Homo sapiens

<400> SEQUENCE: 188

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 189
<211> LENGTH: 112
<212> TYPE: PRT
<213> ORGANISM: Homo sapiens

<400> SEQUENCE: 189

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Gly Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
             85                  90                  95

Leu Gln Thr Pro His Thr Phe Gly Gln Gly Thr Lys Leu Glu Ile Lys
            100                 105                 110

<210> SEQ ID NO 190
<211> LENGTH: 112
<212> TYPE: PRT
<213> ORGANISM: Homo sapiens

<400> SEQUENCE: 190

Asp Val Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
             85                  90                  95

Leu Gln Ser Pro Pro Thr Phe Gly Arg Gly Thr Lys Val Glu Ile Lys
            100                 105                 110

<210> SEQ ID NO 191
<211> LENGTH: 112
<212> TYPE: PRT
<213> ORGANISM: Homo sapiens

<400> SEQUENCE: 191

Asp Val Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
            20                  25                  30

Asn Gly Tyr Asn Tyr Ser Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
             85                  90                  95

Leu Gln Thr Pro Phe Thr Phe Gly Pro Gly Thr Lys Val Asp Ile Lys
            100                 105                 110

<210> SEQ ID NO 192
<211> LENGTH: 112
<212> TYPE: PRT
<213> ORGANISM: Homo sapiens

<400> SEQUENCE: 192

Asp Val Val Met Thr Gln Thr Pro Leu Ser Leu Ser Val Thr Pro Gly
1               5                  10                  15

Gln Pro Ala Ser Ile Ser Cys Arg Ser Ser Gln Ser Leu Leu His Ser
            20                  25                  30

Asp Gly Met Thr Tyr Phe Ser Trp Tyr Leu Gln Lys Pro Gly Gln Pro
```

```
                35                  40                  45
Pro Gln Leu Leu Ile Tyr Glu Val Ser Asn Arg Phe Ser Gly Val Pro
         50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Asn
                 85                  90                  95
Ile Gln Leu Pro Trp Thr Phe Gly Gln Gly Thr Lys Val Glu Ile Lys
            100                 105                 110
```

<210> SEQ ID NO 193
<211> LENGTH: 112
<212> TYPE: PRT
<213> ORGANISM: Homo sapiens

<400> SEQUENCE: 193

```
Asp Val Val Met Thr Gln Ser Pro Leu Ser Leu Ala Val Thr Pro Gly
  1               5                  10                  15
Glu Pro Ala Ser Ile Ser Cys Arg Ser Ser Gln Ser Val Val Phe Thr
                 20                  25                  30
Asn Gly Lys Asn Tyr Leu Asp Trp Tyr Leu Gln Lys Pro Gly Gln Ser
             35                  40                  45
Pro Gln Leu Leu Ile Tyr Leu Gly Ser Asn Arg Ala Ser Gly Val Pro
         50                  55                  60
Asp Arg Phe Ser Gly Ser Gly Ser Gly Thr Asp Phe Thr Leu Lys Ile
 65                  70                  75                  80
Ser Arg Val Glu Ala Asp Asp Val Gly Val Tyr Tyr Cys Met His Ala
                 85                  90                  95
Val Gln Ala Pro Trp Thr Phe Gly Gln Gly Thr Lys Val Glu Ile Lys
            100                 105                 110
```

<210> SEQ ID NO 194
<211> LENGTH: 112
<212> TYPE: PRT
<213> ORGANISM: Homo sapiens

<400> SEQUENCE: 194

```
Asp Val Val Met Thr Gln Ser Pro Leu Ser Leu Ala Val Thr Pro Gly
  1               5                  10                  15
Glu Pro Ala Ser Ile Ser Cys Arg Ser Ser Gln Ser Val Val Phe Thr
                 20                  25                  30
Asn Gly Lys Asn Tyr Leu Asp Trp Tyr Leu Gln Lys Pro Gly Gln Ser
             35                  40                  45
Pro Gln Leu Leu Ile Tyr Leu Gly Ser Asn Arg Ala Ser Gly Val Pro
         50                  55                  60
Asp Arg Phe Ser Gly Ser Gly Ser Gly Thr Asp Phe Thr Leu Lys Ile
 65                  70                  75                  80
Ser Arg Val Glu Ala Asp Asp Val Gly Val Tyr Tyr Cys Met His Ala
                 85                  90                  95
Val Gln Ala Pro Trp Thr Phe Gly Gln Gly Thr Lys Val Glu Ile Lys
            100                 105                 110
```

<210> SEQ ID NO 195
<211> LENGTH: 112
<212> TYPE: PRT
<213> ORGANISM: Homo sapiens

<400> SEQUENCE: 195

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Glu Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Ala Ser Asn Arg Pro Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Asn
                85                  90                  95

Leu Gln Thr Pro Tyr Ser Phe Gly Gln Gly Thr Lys Leu Glu Ile Arg
            100                 105                 110
```

<210> SEQ ID NO 196
<211> LENGTH: 112
<212> TYPE: PRT
<213> ORGANISM: Homo sapiens

<400> SEQUENCE: 196

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro His Ser Phe Gly Gln Gly Thr Lys Leu Glu Ile Lys
            100                 105                 110
```

<210> SEQ ID NO 197
<211> LENGTH: 112
<212> TYPE: PRT
<213> ORGANISM: Homo sapiens

<400> SEQUENCE: 197

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110
```

<210> SEQ ID NO 198
<211> LENGTH: 112
<212> TYPE: PRT
<213> ORGANISM: Homo sapiens

<400> SEQUENCE: 198

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Phe Ala Trp Tyr Leu Gln Lys Pro Gly Gln Ser
        35                  40                  45

Pro Gln Leu Leu Val Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Val
                85                  90                  95

Leu Gln Thr Pro Tyr Thr Phe Gly Gln Gly Thr Lys Leu Glu Ile Ser
            100                 105                 110

<210> SEQ ID NO 199
<211> LENGTH: 112
<212> TYPE: PRT
<213> ORGANISM: Homo sapiens

<400> SEQUENCE: 199

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 200
<211> LENGTH: 112
<212> TYPE: PRT
<213> ORGANISM: Homo sapiens

<400> SEQUENCE: 200

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gly Gly Thr Lys Val Glu Ile Lys
            100                 105                 110

<210> SEQ ID NO 201
<211> LENGTH: 112
<212> TYPE: PRT
<213> ORGANISM: Homo sapiens

<400> SEQUENCE: 201

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu His Trp Tyr Leu Gln Lys Pro Gly Gln Ser
        35                  40                  45

Pro Arg Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Met Gln Ala
                85                  90                  95

Leu Gln Ser Pro Tyr Thr Phe Gly Gln Gly Thr Lys Leu Glu Ile Lys
            100                 105                 110

<210> SEQ ID NO 202
<211> LENGTH: 112
<212> TYPE: PRT
<213> ORGANISM: Homo sapiens

<400> SEQUENCE: 202

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Asn
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu Gln Ile Pro Leu Thr Phe Gly Gly Gly Thr Lys Val Glu Ile Lys
            100                 105                 110

<210> SEQ ID NO 203
<211> LENGTH: 112
<212> TYPE: PRT
<213> ORGANISM: Homo sapiens

<400> SEQUENCE: 203

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser

```
                    20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Asp Tyr Tyr Cys Met Gln Ala
                85                  90                  95

Leu Gln Ser Pro Leu Thr Phe Gly Gly Gly Thr Lys Val Glu Ile Lys
                100                 105                 110
```

<210> SEQ ID NO 204
<211> LENGTH: 112
<212> TYPE: PRT
<213> ORGANISM: Homo sapiens

<400> SEQUENCE: 204

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Phe Asn Tyr Leu His Trp Tyr Leu Gln Lys Pro Gly Gln Ser
            35                  40                  45

Pro Arg Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Met Gln Ala
                85                  90                  95

Leu Gln Ser Pro Tyr Thr Phe Gly Gln Gly Thr Lys Leu Glu Ile Lys
                100                 105                 110
```

<210> SEQ ID NO 205
<211> LENGTH: 112
<212> TYPE: PRT
<213> ORGANISM: Homo sapiens

<400> SEQUENCE: 205

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Phe Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
                100                 105                 110
```

<210> SEQ ID NO 206
<211> LENGTH: 112
<212> TYPE: PRT

```
<213> ORGANISM: Homo sapiens

<400> SEQUENCE: 206

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Glu Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Ala Ser Asn Arg Pro Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Asn
                85                  90                  95

Leu Gln Thr Pro Tyr Ser Phe Gly Gln Gly Thr Lys Leu Glu Ile Arg
            100                 105                 110

<210> SEQ ID NO 207
<211> LENGTH: 112
<212> TYPE: PRT
<213> ORGANISM: Homo sapiens

<400> SEQUENCE: 207

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

<210> SEQ ID NO 208
<211> LENGTH: 112
<212> TYPE: PRT
<213> ORGANISM: Homo sapiens

<400> SEQUENCE: 208

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

-continued

```
Leu Gln Thr Pro Arg Thr Phe Gly Gln Gly Thr Lys Val Glu Ile Lys
                100                 105                 110

<210> SEQ ID NO 209
<211> LENGTH: 112
<212> TYPE: PRT
<213> ORGANISM: Homo sapiens

<400> SEQUENCE: 209

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
                100                 105                 110

<210> SEQ ID NO 210
<211> LENGTH: 112
<212> TYPE: PRT
<213> ORGANISM: Artificial
<220> FEATURE:
<223> OTHER INFORMATION: 158K

<400> SEQUENCE: 210

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
                100                 105                 110

<210> SEQ ID NO 211
<211> LENGTH: 112
<212> TYPE: PRT
<213> ORGANISM: Homo sapiens

<400> SEQUENCE: 211

Asp Val Val Met Thr Gln Ser Pro Leu Ser Leu Pro Val Thr Pro Gly
1               5                   10                  15

Ala Pro Ala Ser Ile Ser Cys Arg Ser Ser Gln Ser Leu Leu His Thr
            20                  25                  30

Asn Gly Val Asn Phe Leu Asp Trp Tyr Leu Gln Lys Pro Gly Gln Ser
```

```
                35                  40                  45
Pro Lys Leu Leu Ile Tyr Leu Ala Ser His Arg Ala Ser Gly Val Pro
     50                  55                  60
Asp Arg Phe Ser Gly Ser Gly Ser Gly Thr Asp Phe Thr Leu Arg Ile
 65                  70                  75                  80
Ser Arg Val Glu Ala Glu Asp Val Gly Ile Tyr Tyr Cys Met Gln Gly
                 85                  90                  95
Leu Gln Thr Pro Phe Thr Phe Gly Pro Gly Thr Lys Leu Glu Ile Lys
                100                 105                 110
```

<210> SEQ ID NO 212
<211> LENGTH: 112
<212> TYPE: PRT
<213> ORGANISM: Homo sapiens

<400> SEQUENCE: 212

```
Asp Val Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu His Ser
                 20                  25                  30
Asn Gly Tyr Asn Tyr Leu Asp Trp Tyr Leu Gln Lys Pro Gly Gln Ser
             35                  40                  45
Pro Gln Leu Leu Ile Tyr Leu Gly Ser Asn Arg Ala Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Leu Gln Thr Pro Leu Thr Phe Gly Gly Gly Thr Lys Val Glu Ile Lys
                100                 105                 110
```

<210> SEQ ID NO 213
<211> LENGTH: 112
<212> TYPE: PRT
<213> ORGANISM: Homo sapiens

<400> SEQUENCE: 213

```
Asp Val Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu His Ser
                 20                  25                  30
Asn Gly Tyr Asn Tyr Leu Asp Trp Tyr Leu Gln Lys Pro Gly Gln Ser
             35                  40                  45
Pro Gln Leu Leu Ile Tyr Leu Gly Ser Asn Arg Ala Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Leu Gln Thr Pro Tyr Thr Phe Gly Gln Gly Thr Lys Leu Glu Ile Lys
                100                 105                 110
```

<210> SEQ ID NO 214
<211> LENGTH: 112
<212> TYPE: PRT
<213> ORGANISM: Homo sapiens

<400> SEQUENCE: 214

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 215
<211> LENGTH: 112
<212> TYPE: PRT
<213> ORGANISM: Homo sapiens

<400> SEQUENCE: 215

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 216
<211> LENGTH: 112
<212> TYPE: PRT
<213> ORGANISM: Homo sapiens

<400> SEQUENCE: 216

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Gly Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro His Thr Phe Gly Gln Gly Thr Lys Leu Glu Ile Lys
            100                 105                 110

<210> SEQ ID NO 217
<211> LENGTH: 112
<212> TYPE: PRT
<213> ORGANISM: Homo sapiens

<400> SEQUENCE: 217

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser Pro Pro Thr Phe Gly Arg Gly Thr Lys Val Glu Ile Lys
            100                 105                 110

<210> SEQ ID NO 218
<211> LENGTH: 112
<212> TYPE: PRT
<213> ORGANISM: Homo sapiens

<400> SEQUENCE: 218

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Ser Asp Trp Tyr Leu Gln Lys Pro Gly Gln Ser
        35                  40                  45

Pro Gln Leu Leu Ile Tyr Leu Gly Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 219
<211> LENGTH: 112
<212> TYPE: PRT
<213> ORGANISM: Homo sapiens

<400> SEQUENCE: 219

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asp Gly Met Thr Tyr Phe Ser Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Asn
                 85                  90                  95

Ile Gln Leu Pro Trp Thr Phe Gly Gln Gly Thr Lys Val Glu Ile Lys
            100                 105                 110
```

<210> SEQ ID NO 220
<211> LENGTH: 112
<212> TYPE: PRT
<213> ORGANISM: Homo sapiens

<400> SEQUENCE: 220

```
Asp Val Val Met Thr Gln Ser Pro Leu Ser Leu Ala Val Thr Pro Gly
  1               5                  10                  15

Glu Pro Ala Ser Ile Ser Cys Arg Ser Ser Gln Ser Val Phe Thr
                 20                  25                  30

Asn Gly Lys Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Val Tyr Tyr Cys Met His Ala
                 85                  90                  95

Val Gln Ala Pro Trp Thr Phe Gly Gln Gly Thr Lys Val Glu Ile Lys
            100                 105                 110
```

<210> SEQ ID NO 221
<211> LENGTH: 112
<212> TYPE: PRT
<213> ORGANISM: Homo sapiens

<400> SEQUENCE: 221

```
Asp Val Val Met Thr Gln Ser Pro Leu Ser Leu Ala Val Thr Pro Gly
  1               5                  10                  15

Glu Pro Ala Ser Ile Ser Cys Arg Ser Ser Gln Ser Val Phe Thr
                 20                  25                  30

Asn Gly Lys Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Val Tyr Tyr Cys Met His Ala
                 85                  90                  95

Val Gln Ala Pro Trp Thr Phe Gly Gln Gly Thr Lys Val Glu Ile Lys
            100                 105                 110
```

<210> SEQ ID NO 222
<211> LENGTH: 112
<212> TYPE: PRT
<213> ORGANISM: Homo sapiens

<400> SEQUENCE: 222

```
Asp Ile Val Met Thr Gln Thr Pro Leu Ser Leu Pro Val Thr Pro Gly
  1               5                  10                  15

Glu Pro Ala Ser Ile Ser Cys Arg Ser Ser Gln Ser Leu Leu Glu Ser
```

```
            20                  25                  30

His Gly Tyr Asn Tyr Leu Asp Trp Tyr Leu Gln Lys Pro Gly Gln Ser
            35                  40                  45

Pro Gln Leu Leu Ile Tyr Leu Ala Ser Asn Arg Pro Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Asn
                85                  90                  95

Leu Gln Thr Pro Tyr Ser Phe Gly Gln Gly Thr Lys Leu Glu Ile Arg
            100                 105                 110

<210> SEQ ID NO 223
<211> LENGTH: 112
<212> TYPE: PRT
<213> ORGANISM: Homo sapiens

<400> SEQUENCE: 223

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro His Ser Phe Gly Gln Gly Thr Lys Leu Glu Ile Lys
            100                 105                 110

<210> SEQ ID NO 224
<211> LENGTH: 112
<212> TYPE: PRT
<213> ORGANISM: Homo sapiens

<400> SEQUENCE: 224

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 225
<211> LENGTH: 112
<212> TYPE: PRT
```

<213> ORGANISM: Homo sapiens

<400> SEQUENCE: 225

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Phe Ala Trp Tyr Leu Gln Lys Pro Gly Gln Ser
        35                  40                  45

Pro Gln Leu Leu Val Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Val
                85                  90                  95

Leu Gln Thr Pro Tyr Thr Phe Gly Gln Gly Thr Lys Leu Glu Ile Ser
            100                 105                 110

<210> SEQ ID NO 226
<211> LENGTH: 112
<212> TYPE: PRT
<213> ORGANISM: Homo sapiens

<400> SEQUENCE: 226

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 227
<211> LENGTH: 112
<212> TYPE: PRT
<213> ORGANISM: Homo sapiens

<400> SEQUENCE: 227

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gly Gly Thr Lys Val Glu Ile Lys
            100                 105                 110

<210> SEQ ID NO 228
<211> LENGTH: 112
<212> TYPE: PRT
<213> ORGANISM: Homo sapiens

<400> SEQUENCE: 228

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu His Trp Tyr Leu Gln Lys Pro Gly Gln Ser
        35                  40                  45

Pro Arg Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Met Gln Ala
                85                  90                  95

Leu Gln Ser Pro Tyr Thr Phe Gly Gln Gly Thr Lys Leu Glu Ile Lys
            100                 105                 110

<210> SEQ ID NO 229
<211> LENGTH: 112
<212> TYPE: PRT
<213> ORGANISM: Homo sapiens

<400> SEQUENCE: 229

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Phe Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 230
<211> LENGTH: 113
<212> TYPE: PRT
<213> ORGANISM: Homo sapiens

<400> SEQUENCE: 230

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Glu Ser
            20                  25                  30

His Gly Tyr Asn Tyr Leu Asp Trp Tyr Leu Gln Lys Pro Gly Gln Ser
        35                  40                  45

```
Pro Gln Leu Leu Ile Tyr Leu Ala Ser Asn Arg Pro Ser Gly Val Pro
    50                  55                  60

Asp Arg Phe Ser Gly Ser Gly Ser Gly Thr Asp Phe Thr Leu Lys Ile
 65              70                  75                      80

Ser Arg Val Glu Ala Glu Asp Val Gly Ile Tyr Tyr Cys Met Gln Asn
                 85                  90                  95

Leu Gln Thr Pro Tyr Ser Phe Gly Gln Gly Thr Lys Leu Glu Ile
            100                 105                 110

Arg
```

<210> SEQ ID NO 231
<211> LENGTH: 112
<212> TYPE: PRT
<213> ORGANISM: Homo sapiens

<400> SEQUENCE: 231

```
Asp Ile Val Met Thr Gln Thr Pro Leu Ser Leu Pro Val Thr Pro Gly
 1               5                  10                      15

Glu Pro Ala Ser Ile Ser Cys Arg Ser Ser Gln Ser Leu Leu His Gly
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65              70                  75                      80

Ser Arg Val Glu Ala Glu Asp Val Gly Val Tyr Tyr Cys Met Gln Ala
                 85                  90                  95

Leu Gln Thr Pro Arg Thr Phe Gly Gln Gly Thr Lys Val Glu Ile Lys
            100                 105                 110
```

<210> SEQ ID NO 232
<211> LENGTH: 112
<212> TYPE: PRT
<213> ORGANISM: Homo sapiens

<400> SEQUENCE: 232

```
Asp Ile Val Met Thr Gln Thr Pro Leu Ser Leu Pro Val Thr Pro Gly
 1               5                  10                      15

Glu Pro Ala Ser Ile Ser Cys Arg Ser Ser Gln Ser Leu Leu His Gly
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65              70                  75                      80

Ser Arg Val Glu Ala Glu Asp Val Gly Val Tyr Tyr Cys Met Gln Ala
                 85                  90                  95

Leu Gln Thr Pro Arg Thr Phe Gly Gln Gly Thr Lys Val Glu Ile Lys
            100                 105                 110
```

<210> SEQ ID NO 233
<211> LENGTH: 112
<212> TYPE: PRT
<213> ORGANISM: Homo sapiens

<400> SEQUENCE: 233

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110
```

<210> SEQ ID NO 234
<211> LENGTH: 112
<212> TYPE: PRT
<213> ORGANISM: Artificial
<220> FEATURE:
<223> OTHER INFORMATION: 158 VK

<400> SEQUENCE: 234

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110
```

<210> SEQ ID NO 235
<211> LENGTH: 112
<212> TYPE: PRT
<213> ORGANISM: Homo sapiens

<400> SEQUENCE: 235

```
Asp Val Val Met Thr Gln Ser Pro Leu Ser Leu Pro Val Thr Pro Gly
1               5                   10                  15

Ala Pro Ala Ser Ile Ser Cys Arg Ser Ser Gln Ser Leu Leu His Thr
            20                  25                  30

Asn Gly Val Asn Phe Leu Asp Trp Tyr Leu Gln Lys Pro Gly Gln Ser
        35                  40                  45

Pro Lys Leu Leu Ile Tyr Leu Ala Ser His Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Gly
                85                  90                  95
```

```
Leu Gln Thr Pro Phe Thr Phe Gly Pro Gly Thr Lys Leu Glu Ile Asn
            100                 105                 110
```

<210> SEQ ID NO 236
<211> LENGTH: 100
<212> TYPE: PRT
<213> ORGANISM: Homo sapiens

<400> SEQUENCE: 236

```
Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100
```

<210> SEQ ID NO 237
<211> LENGTH: 60
<212> TYPE: DNA
<213> ORGANISM: Artificial
<220> FEATURE:
<223> OTHER INFORMATION: 158VK A19 leader sequence

<400> SEQUENCE: 237

```
atgaggctcc ctgctcagct cctggggctg ctaatgctct gggtctctgg atccagtggg      60
```

<210> SEQ ID NO 238
<211> LENGTH: 20
<212> TYPE: PRT
<213> ORGANISM: Artificial
<220> FEATURE:
<223> OTHER INFORMATION: 158VK A19 Leader sequence

<400> SEQUENCE: 238

```
Met Arg Leu Pro Ala Gln Leu Leu Gly Leu Leu Met Leu Trp Val Ser
1               5                   10                  15

Gly Ser Ser Gly
            20
```

<210> SEQ ID NO 239
<211> LENGTH: 50
<212> TYPE: PRT
<213> ORGANISM: Artificial
<220> FEATURE:
<223> OTHER INFORMATION: A19 signal sequence

<400> SEQUENCE: 239

```
Met Arg Leu Pro Ala Gln Leu Leu Gly Leu Leu Met Leu Trp Val Ser
1               5                   10                  15

Gly Ser Ser Gly Asp Val Val Met Thr Gln Ser Pro Leu Ser Leu Pro
            20                  25                  30

Val Thr Pro Gly Ala Pro Ala Ser Ile Ser Cys Arg Ser Ser Gln Ser
        35                  40                  45
```

Leu Leu
    50

<210> SEQ ID NO 240
<211> LENGTH: 112
<212> TYPE: PRT
<213> ORGANISM: Artificial
<220> FEATURE:
<223> OTHER INFORMATION: 158 VK

<400> SEQUENCE: 240

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 241
<211> LENGTH: 16
<212> TYPE: PRT
<213> ORGANISM: Artificial
<220> FEATURE:
<223> OTHER INFORMATION: 158 VK CDR1

<400> SEQUENCE: 241

Arg Ser Ser Gln Ser Ile Val His Ser Asn Gly Asn Thr Tyr Leu Glu
1               5                   10                  15

<210> SEQ ID NO 242
<211> LENGTH: 7
<212> TYPE: PRT
<213> ORGANISM: Artificial
<220> FEATURE:
<223> OTHER INFORMATION: 158 VK CDR2

<400> SEQUENCE: 242

Lys Val Ser Asn Arg Phe Ser
1               5

<210> SEQ ID NO 243
<211> LENGTH: 9
<212> TYPE: PRT
<213> ORGANISM: Artificial
<220> FEATURE:
<223> OTHER INFORMATION: 158 VK CDR3

<400> SEQUENCE: 243

Phe Gln Gly Ser His Val Pro Pro Thr
1               5

<210> SEQ ID NO 244
<211> LENGTH: 112
<212> TYPE: PRT
<213> ORGANISM: Artificial
<220> FEATURE:

<223> OTHER INFORMATION: 158RKA

<400> SEQUENCE: 244

Asp Val Val Met Thr Gln Ser Pro Leu Ser Leu Pro Val Thr Pro Gly
1               5                   10                  15

Ala Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
            100                 105                 110

<210> SEQ ID NO 245
<211> LENGTH: 23
<212> TYPE: PRT
<213> ORGANISM: Artificial
<220> FEATURE:
<223> OTHER INFORMATION: AB064054 FW1

<400> SEQUENCE: 245

Asp Val Val Met Thr Gln Ser Pro Leu Ser Leu Pro Val Thr Pro Gly
1               5                   10                  15

Ala Pro Ala Ser Ile Ser Cys
            20

<210> SEQ ID NO 246
<211> LENGTH: 15
<212> TYPE: PRT
<213> ORGANISM: Artificial
<220> FEATURE:
<223> OTHER INFORMATION: AB064054 FW2

<400> SEQUENCE: 246

Trp Tyr Leu Gln Lys Pro Gly Gln Ser Pro Lys Leu Leu Ile Tyr
1               5                   10                  15

<210> SEQ ID NO 247
<211> LENGTH: 32
<212> TYPE: PRT
<213> ORGANISM: Artificial
<220> FEATURE:
<223> OTHER INFORMATION: AB064054 FW3

<400> SEQUENCE: 247

Gly Val Pro Asp Arg Phe Ser Gly Ser Gly Ser Gly Thr Asp Phe Thr
1               5                   10                  15

Leu Arg Ile Ser Arg Val Glu Ala Glu Asp Val Gly Ile Tyr Tyr Cys
            20                  25                  30

<210> SEQ ID NO 248
<211> LENGTH: 10
<212> TYPE: PRT
<213> ORGANISM: Artificial
<220> FEATURE:
<223> OTHER INFORMATION: AB064054 FW4

<400> SEQUENCE: 248

```
Phe Gly Pro Gly Thr Lys Leu Glu Ile Lys
1               5                  10
```

<210> SEQ ID NO 249
<211> LENGTH: 112
<212> TYPE: PRT
<213> ORGANISM: Homo sapiens

<400> SEQUENCE: 249

```
Asp Val Val Met Thr Gln Ser Pro Leu Ser Leu Pro Val Thr Pro Gly
1               5                   10                  15

Ala Pro Ala Ser Ile Ser Cys Arg Ser Ser Gln Ser Leu Leu His Thr
            20                  25                  30

Asn Gly Val Asn Phe Leu Asp Trp Tyr Leu Gln Lys Pro Gly Gln Ser
        35                  40                  45

Pro Lys Leu Leu Ile Tyr Leu Ala Ser His Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Gly
                85                  90                  95

Leu Gln Thr Pro Phe Thr Phe Gly Pro Gly Thr Lys Leu Glu Ile Lys
            100                 105                 110
```

<210> SEQ ID NO 250
<211> LENGTH: 60
<212> TYPE: DNA
<213> ORGANISM: Artificial
<220> FEATURE:
<223> OTHER INFORMATION: A19 Leader sequence

<400> SEQUENCE: 250

```
atgaggctcc ctgctcagct cctggggctg ctaatgctct gggtctctgg atccagtggg    60
```

<210> SEQ ID NO 251
<211> LENGTH: 20
<212> TYPE: PRT
<213> ORGANISM: Artificial
<220> FEATURE:
<223> OTHER INFORMATION: A19 Leader sequence

<400> SEQUENCE: 251

```
Met Arg Leu Pro Ala Gln Leu Leu Gly Leu Leu Met Leu Trp Val Ser
1               5                   10                  15

Gly Ser Ser Gly
            20
```

<210> SEQ ID NO 252
<211> LENGTH: 69
<212> TYPE: DNA
<213> ORGANISM: Artificial
<220> FEATURE:
<223> OTHER INFORMATION: AB064054 FW1

<400> SEQUENCE: 252

```
gatgttgtga tgactcagtc tccactctcc ctgcccgtca cccctggagc gccggcctcc    60
atctcctgc                                                           69
```

<210> SEQ ID NO 253
<211> LENGTH: 48
<212> TYPE: DNA

```
<213> ORGANISM: Artificial
<220> FEATURE:
<223> OTHER INFORMATION: 158 CDR1

<400> SEQUENCE: 253
agatctagtc agagcattgt acatagtaat ggaaacacct atttagaa          48

<210> SEQ ID NO 254
<211> LENGTH: 45
<212> TYPE: DNA
<213> ORGANISM: Artificial
<220> FEATURE:
<223> OTHER INFORMATION: AB064054 FW2

<400> SEQUENCE: 254
tggtatctgc agaagccagg gcagtctcca aagctcctga tctat             45

<210> SEQ ID NO 255
<211> LENGTH: 21
<212> TYPE: DNA
<213> ORGANISM: Artificial
<220> FEATURE:
<223> OTHER INFORMATION: 158 CDR2

<400> SEQUENCE: 255
aaagtttcca accgattttc t                                       21

<210> SEQ ID NO 256
<211> LENGTH: 96
<212> TYPE: DNA
<213> ORGANISM: Artificial
<220> FEATURE:
<223> OTHER INFORMATION: AB064054 FW3

<400> SEQUENCE: 256
ggagtccctg acaggttcag tggcagtggg tcaggcacag attttacact gagaatcagc   60
agagtggagg ctgaggatgt tggaatttat tactgc                           96

<210> SEQ ID NO 257
<211> LENGTH: 27
<212> TYPE: DNA
<213> ORGANISM: Artificial
<220> FEATURE:
<223> OTHER INFORMATION: 158 CDR3

<400> SEQUENCE: 257
tttcaaggtt cacatgttcc tccgacg                                 27

<210> SEQ ID NO 258
<211> LENGTH: 30
<212> TYPE: DNA
<213> ORGANISM: Artificial
<220> FEATURE:
<223> OTHER INFORMATION: AB064054 FW4

<400> SEQUENCE: 258
ttcggccctg ggaccaaatt ggaaatcaaa                              30

<210> SEQ ID NO 259
<211> LENGTH: 396
<212> TYPE: DNA
<213> ORGANISM: Artificial
<220> FEATURE:
<223> OTHER INFORMATION: 158RKAss DNA Sequence

<400> SEQUENCE: 259
```

```
atgaggctcc ctgctcagct cctggggctg ctaatgctct gggtctctgg atccagtggg    60
gatgttgtga tgactcagtc tccactctcc ctgcccgtca ccctggagc gccggcctcc    120 atctcctgca gatctagtca gagcattgta catagtaatg aaacaccta tttagaatgg    180 tatctgcaga agccagggca gtctccaaag ctcctgatct ataaagtttc caaccgattt    240
tctggagtcc ctgacaggtt cagtggcagt gggtcaggca cagattttac actgagaatc    300
agcagagtgg aggctgagga tgttggaatt tattactgct ttcaaggttc acatgttcct    360
ccgacgttcg gcctgggac caaattggaa atcaaa                              396
```

<210> SEQ ID NO 260
<211> LENGTH: 132
<212> TYPE: PRT
<213> ORGANISM: Artificial
<220> FEATURE:
<223> OTHER INFORMATION: 158RKAss Protein sequence

<400> SEQUENCE: 260

```
Met Arg Leu Pro Ala Gln Leu Leu Gly Leu Leu Met Leu Trp Val Ser
1               5                   10                  15

Gly Ser Ser Gly Asp Val Val Met Thr Gln Ser Pro Leu Ser Leu Pro
            20                  25                  30

Val Thr Pro Gly Ala Pro Ala Ser Ile Ser Cys Arg Ser Ser Gln Ser
        35                  40                  45

Ile Val His Ser Asn Gly Asn Thr Tyr Leu Glu Trp Tyr Leu Gln Lys
    50                  55                  60

Pro Gly Gln Ser Pro Lys Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Arg Ile Ser Arg Val Glu Ala Glu Asp Val Gly Ile Tyr Tyr
            100                 105                 110

Cys Phe Gln Gly Ser His Val Pro Pro Thr Phe Gly Pro Gly Thr Lys
        115                 120                 125

Leu Glu Ile Lys
    130
```

<210> SEQ ID NO 261
<211> LENGTH: 396
<212> TYPE: DNA
<213> ORGANISM: Artificial
<220> FEATURE:
<223> OTHER INFORMATION: 158RKA

<400> SEQUENCE: 261

```
atgaggctcc ctgctcagct cctggggctg ctaatgctct gggtctctgg aagcagtggg    60
gatgttgtga tgactcagtc tccactctcc ctgcccgtca ccctggagc gccggcctcc    120 atctcctgca gatctagtca gagcattgta catagtaatg aaacaccta tttagagtgg    180 tatcttcaaa agccagggca gtctccaaag ctcctgatct ataaagtttc caaccgattt    240
tctggagtcc ctgacaggtt cagtggaagt ggatcaggca cagattttac actgagaatc    300
agcagagtgg aggctgagga tgttggaatt tattactgct ttcaaggttc acatgttcct    360
ccgacgttcg gcctgggac caaattggaa atcaaa                              396
```

<210> SEQ ID NO 262
<211> LENGTH: 396

<212> TYPE: DNA
<213> ORGANISM: Artificial
<220> FEATURE:
<223> OTHER INFORMATION: 158RKAss

<400> SEQUENCE: 262

```
atgaggctcc ctgctcagct cctggggctg ctaatgctct gggtctctgg atccagtggg      60
gatgttgtga tgactcagtc tccactctcc ctgcccgtca cccctggagc gccggcctcc     120
atctcctgca gatctagtca gagcattgta catagtaatg aaacacctta tttagaatgg     180
tatctgcaga agccagggca gtctccaaag ctcctgatct ataaagtttc caaccgattt     240
tctggagtcc ctgacaggtt cagtggcagt gggtcaggca cagattttac actgagaatc     300
agcagagtgg aggctgagga tgttggaatt tattactgct ttcaaggttc acatgttcct     360
ccgacgttcg gcctgggac caaattggaa atcaaa                                396
```

<210> SEQ ID NO 263
<211> LENGTH: 396
<212> TYPE: DNA
<213> ORGANISM: Artificial
<220> FEATURE:
<223> OTHER INFORMATION: 158RKA DNA Sequence

<400> SEQUENCE: 263

```
atgaggctcc ctgctcagct cctggggctg ctaatgctct gggtctctgg aagcagtggg      60
gatgttgtga tgactcagtc tccactctcc ctgcccgtca cccctggagc gccggcctcc     120
atctcctgca gatctagtca gagcattgta catagtaatg aaacacctta tttagagtgg     180
tatcttcaaa agccagggca gtctccaaag ctcctgatct ataaagtttc caaccgattt     240
tctggagtcc ctgacaggtt cagtggaagt ggatcaggca cagattttac actgagaatc     300
agcagagtgg aggctgagga tgttggaatt tattactgct ttcaaggttc acatgttcct     360
ccgacgttcg gcctgggac caaattggaa atcaaa                                396
```

<210> SEQ ID NO 264
<211> LENGTH: 132
<212> TYPE: PRT
<213> ORGANISM: Artificial
<220> FEATURE:
<223> OTHER INFORMATION: 158RKA Protein sequence

<400> SEQUENCE: 264

```
Met Arg Leu Pro Ala Gln Leu Leu Gly Leu Leu Met Leu Trp Val Ser
1               5                   10                  15

Gly Ser Ser Gly Asp Val Val Met Thr Gln Ser Pro Leu Ser Leu Pro
            20                  25                  30

Val Thr Pro Gly Ala Pro Ala Ser Ile Ser Cys Arg Ser Ser Gln Ser
        35                  40                  45

Ile Val His Ser Asn Gly Asn Thr Tyr Leu Glu Trp Tyr Leu Gln Lys
    50                  55                  60

Pro Gly Gln Ser Pro Lys Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Arg Ile Ser Arg Val Glu Ala Glu Asp Val Gly Ile Tyr Tyr
            100                 105                 110

Cys Phe Gln Gly Ser His Val Pro Pro Thr Phe Gly Pro Gly Thr Lys
        115                 120                 125
```

-continued

```
Leu Glu Ile Lys
    130

<210> SEQ ID NO 265
<211> LENGTH: 123
<212> TYPE: PRT
<213> ORGANISM: Artificial
<220> FEATURE:
<223> OTHER INFORMATION: 158RHA

<400> SEQUENCE: 265

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser
        115                 120

<210> SEQ ID NO 266
<211> LENGTH: 123
<212> TYPE: PRT
<213> ORGANISM: Artificial
<220> FEATURE:
<223> OTHER INFORMATION: 158RHB

<400> SEQUENCE: 266

Asp Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser
        115                 120

<210> SEQ ID NO 267
<211> LENGTH: 123
<212> TYPE: PRT
<213> ORGANISM: Artificial
<220> FEATURE:
<223> OTHER INFORMATION: 158RHC
```

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Pro Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser
        115                 120

<210> SEQ ID NO 268
<211> LENGTH: 123
<212> TYPE: PRT
<213> ORGANISM: Artificial
<220> FEATURE:
<223> OTHER INFORMATION: 158RHD

<400> SEQUENCE: 268

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Tyr Tyr Gly Asp Thr Val
    50                  55                  60

Lys Gly Arg Phe Thr Ile Ser Arg Asp Asn Ala Lys Asn Ser Leu Phe
65                  70                  75                  80

Leu Gln Met Thr Ser Leu Arg Ala Glu Asp Thr Ala Val Tyr Tyr Cys
                85                  90                  95

Ala Arg Glu Gly Gly Tyr Tyr Tyr Gly Arg Ser Tyr Tyr Thr Met Asp
            100                 105                 110

Tyr Trp Gly Gln Gly Thr Thr Val Thr Val Ser
        115                 120

<210> SEQ ID NO 269
<211> LENGTH: 112
<212> TYPE: PRT
<213> ORGANISM: Artificial
<220> FEATURE:
<223> OTHER INFORMATION: 158RKA

<400> SEQUENCE: 269

Asp Val Val Met Thr Gln Ser Pro Leu Ser Leu Pro Val Thr Pro Gly
1               5                   10                  15

Ala Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

```
Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
                100                 105                 110

<210> SEQ ID NO 270
<211> LENGTH: 112
<212> TYPE: PRT
<213> ORGANISM: Artificial
<220> FEATURE:
<223> OTHER INFORMATION: 158RKB

<400> SEQUENCE: 270

Asp Val Leu Met Thr Gln Ser Pro Leu Ser Leu Pro Val Thr Pro Gly
1               5                   10                  15

Ala Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
                100                 105                 110

<210> SEQ ID NO 271
<211> LENGTH: 112
<212> TYPE: PRT
<213> ORGANISM: Artificial
<220> FEATURE:
<223> OTHER INFORMATION: 158RKC

<400> SEQUENCE: 271

Asp Val Val Met Thr Gln Ser Pro Leu Ser Leu Pro Val Thr Pro Gly
1               5                   10                  15

Ala Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Phe Gln Gly
                85                  90                  95

Ser His Val Pro Pro Thr Phe Gly Gly Gly Thr Lys Leu Glu Ile Lys
                100                 105                 110

<210> SEQ ID NO 272
<211> LENGTH: 5
<212> TYPE: PRT
<213> ORGANISM: Artificial Sequence
```

```
<220> FEATURE:
<223> OTHER INFORMATION: Synthetic Construct

<400> SEQUENCE: 272

Ser Phe Gly Met His
1               5

<210> SEQ ID NO 273
<211> LENGTH: 5
<212> TYPE: PRT
<213> ORGANISM: Artificial Sequence
<220> FEATURE:
<223> OTHER INFORMATION: Synthetic Construct

<400> SEQUENCE: 273

Ser Tyr Ala Met Ser
1               5

<210> SEQ ID NO 274
<211> LENGTH: 17
<212> TYPE: PRT
<213> ORGANISM: Artificial Sequence
<220> FEATURE:
<223> OTHER INFORMATION: Synthetic Construct

<400> SEQUENCE: 274

Tyr Ile Ser Ser Gly Ser Ser Thr Ile Tyr Tyr Ala Asp Thr Val Lys
1               5                   10                  15

Gly

<210> SEQ ID NO 275
<211> LENGTH: 17
<212> TYPE: PRT
<213> ORGANISM: Artificial Sequence
<220> FEATURE:
<223> OTHER INFORMATION: Synthetic Construct

<400> SEQUENCE: 275

Tyr Ile Ser Ser Gly Ser Ser Thr Ile Tyr Tyr Gly Asp Thr Val Lys
1               5                   10                  15

Gly

<210> SEQ ID NO 276
<211> LENGTH: 8
<212> TYPE: PRT
<213> ORGANISM: Artificial Sequence
<220> FEATURE:
<223> OTHER INFORMATION: Synthetic Construct

<400> SEQUENCE: 276

Tyr Gly Asn Tyr Ala Met Asp Tyr
1               5

<210> SEQ ID NO 277
<211> LENGTH: 10
<212> TYPE: PRT
<213> ORGANISM: Artificial Sequence
<220> FEATURE:
<223> OTHER INFORMATION: Synthetic Construct

<400> SEQUENCE: 277

Asn Tyr Gly Ser Arg Arg Tyr Phe Asp Val
1               5                   10

<210> SEQ ID NO 278
```

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 278

Glu Gly Gly Tyr Tyr Tyr Gly Arg Ser Tyr Tyr Thr Met Asp Tyr
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Synthetic Construct

<400> SEQUENCE: 279

Arg Ser Ser Gln Ser Ile Val His Ser Asn Gly Asn Thr Tyr Leu Glu
1               5                   10                  15

<210> SEQ ID NO 280
<211> LENGTH: 11
<212> TYPE: PRT
<213> ORGANISM: Artificial Sequence
<220> FEATURE:
<223> OTHER INFORMATION: Synthetic Construct

<400> SEQUENCE: 280

Lys Ala Ser Gln Ser Val Ser Asn Asp Val Ala
1               5                   10

<210> SEQ ID NO 281
<211> LENGTH: 7
<212> TYPE: PRT
<213> ORGANISM: Artificial Sequence
<220> FEATURE:
<223> OTHER INFORMATION: Synthetic Construct

<400> SEQUENCE: 281

Lys Val Ser Asn Arg Phe Ser
1               5

<210> SEQ ID NO 282
<211> LENGTH: 7
<212> TYPE: PRT
<213> ORGANISM: Artificial Sequence
<220> FEATURE:
<223> OTHER INFORMATION: Synthetic Construct

<400> SEQUENCE: 282

Tyr Ala Ser Asn Arg Tyr Thr
1               5

<210> SEQ ID NO 283
<211> LENGTH: 9
<212> TYPE: PRT
<213> ORGANISM: Artificial Sequence
<220> FEATURE:
<223> OTHER INFORMATION: Synthetic Construct

<400> SEQUENCE: 283

Phe Gln Gly Ser His Val Pro Pro Thr
1               5

<210> SEQ ID NO 284
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 284

Gln Gln Asp Tyr Ser Ser Pro Phe Thr
1               5
```

PROTOFIBRIL SELECTIVE ANTIBODIES AND THE USE THEREOF

CROSS-REFERENCE TO RELATED APPLICATIONS

This application is a divisional of U.S. patent application Ser. No. 12/294,207, filed Sep. 23, 2008, which is the national stage of International Application No. PCT/SE2007/000292, filed Mar. 23, 2007, which claims the benefit of SE 0600662-1, filed Mar. 23, 2006, and SE 0602591-0, filed Nov. 30, 2006.

FIELD OF INVENTION

This invention pertains to the prevention, treatment and diagnosis of neurodegenerative diseases, in particular Alzheimer's disease, and other similar disease. More precisely, to high affinity $10^{-7}$M, preferably $10^{-8}$M, even less than $10^{-9}$M or less than $10^{-10}$ M or $10^{-11}$ M antibodies, selective for amyloid beta protein (Aβ) in its protofibril conformation and of IgG class and IgG1 or IgG4 subclass or combinations thereof or mutations thereof, retaining high Fc receptor binding and low C1 (C1q) binding, effective in clearance of Aβ protofibrils and with reduce risk of inflammation.

BACKGROUND

Alzheimer's disease (AD) is a progressive and irreversible neurodegenerative disorder causing cognitive, memory and behavioural impairments. It is the most common cause of dementia in the elderly population affecting roughly 5% of the population above 65 years and 20% above 80 years of age. AD is characterized by an insidious onset and progressive deterioration in multiple cognitive functions. The neuropathology involves both extracellular and intracellular argyrophillic proteineous deposits. The extracellular deposits, referred to as neuritic plaques, mainly consist of amyloid beta protein (Aβ) surrounded by dystrophic neurites (swollen, distorted neuronal processes). Aβ within these extracellular deposits are fibrillar in its character with a β-pleated sheet structure. Aβ in these deposits can be stained with certain dyes, e.g. Congo Red, and display a fibrillar ultra structure. These characteristics, adopted by Aβ in its fibrillar structure in neuritic plaques, are the definition of the generic term amyloid. The classic intracellular AD pathologic lesion is the neurofibrillary tangle (NFT) which consists of filamentous structures called paired helical filaments (PHFs), composed of twisted strands of hyperphosphorylated microtubule-associated protein tau. Frequent neuritic plaques and neurofibrillary tangle deposits in the brain are diagnostic criteria for AD, as carried out post mortem. AD brains also display macroscopic brain atrophy, nerve cell loss, local inflammation (microgliosis and astrocytosis) and often cerebral amyloid angiopathy (CAA) in cerebral vessel walls.

Two forms of Aβ peptides, Aβ40 and Aβ42, are the dominant species in AD neuritic plaques while Aβ40 is the prominent species in cerebrovascular amyloid associated with AD. Enzymatic activities allow Aβ to be continuously formed from a larger protein called the amyloid precursor protein (APP) in both healthy and AD afflicted subjects in all cells of the body. Two major APP processing events through β- and γ-secretase activities enables Aβ production, while a third enzyme called α-secretase, prevents Aβ generation by cleavage inside the Aβ sequence (Selkoe, 1994; Ester 2001;U.S. Pat. No. 5,604,102). The Aβ42 is a fortytwo amino acid long peptide, i.e. two amino acids longer at the C-terminus, as compared to Aβ40. Aβ42 is more hydrophobic, and does more easily aggregate into larger structures of Aβ peptides (Jarret 1993) such as Aβ dimers, Aβ trimers, Aβ tetramers, Aβ oligomers, Aβ protofibrils or Aβ fibrils. Aβ fibrils are hydrophobic and insoluble, while the other structures are all less hydrophobic and soluble. All these higher molecular structures of Aβ peptides are individually defined based on their biophysical and structural appearance e.g. in electron microscopy, and their biochemical characteristics e.g. by analysis with size-exclusion chromatography/western blot. These Aβ peptides, particularly Aβ42, will gradually assemble into a various higher molecular structures of Aβ during the life span. AD, which is a strongly age-dependent disorder, will occur earlier in life if this assembly process occurs more rapidly. This is the core of the "amyloid cascade hypothesis" of AD which claims that APP processing, the Aβ42 levels and their assembly into higher molecular structures is a central cause of AD. All other neuropathology of AD brain and the symptoms of AD such as dementia are somehow caused by Aβ or assembled forms thereof.

Aβ can exist in different lengths i.e. 1-39, 1-40, 1-42 and 1-43 and fragments sizes i.e. 1-28 and 25-35. Truncations might occur at the N-terminus of the peptide. All these peptides can aggregate and form soluble intermediates and insoluble fibrils, each molecular form having a unique structural conformation and biophysical property. Monomeric Aβ1-42 for example, is a 42 amino acid long soluble and non toxic peptide, that is suggested to be involved in normal synapse functions. Under certain conditions, the Aβ1-42 can aggregate into dimers, trimers, tetramers, pentamers up to 12-mer and higher oligomeric forms, all with its distinct physicochemical property such as molecular size, EM structure and AFM (atomic force microscopy) molecular shape. An example of a higher molecular weight soluble oligomeric Aβ form is the protofibril (Walsh 1997), which has an apparent molecular weight >100 kDa and a curvelinear structure of 4-11 nm in diameter and <200 nm in length. It has recently been demonstrated that soluble oligomeric Aβ peptides such as Aβ protofibrils impair long-term potentiation (LTP) a measure of synaptic plasticity that is thought to reflect memory formation in the hippocampus (Walsh 2002). Furthermore, oligomeric Arctic Aβ peptides display much more profound inhibitory effect than wtAβ on LTP in the brain, likely due to their strong propensity to form Aβ protofibrils (Klyubin 2003).

There are also other soluble oligomeric forms described in the literature that are distinctly different from protofibrils. One such oligomeric form is ADDL (Amyloid Derived Diffusible Ligand) (Lambert 1998). AFM analysis of ADDL revealed predominantly small globular species of 4.7-6.2 nm along the z-axis with molecular weights of 17-42 kDa (Stine 1996). Another form is called ASPD (Amyloidspheroids) (Hoshi 2003). ASPD are spherical oligomers of Aβ1-40. Toxicity studies showed that spherical ASPD >10 nm were more toxic than lower molecular forms (Hoshi 2003). This idea has gained support from recent discovery of the Arctic (E693) APP mutation, which causes early-onset AD (US 2002/0162129 A1; Nilsberth et al., 2001). The mutation is located inside the Aβ peptide sequence. Mutation carriers will thereby generate variants of Aβ peptides e.g. Arctic Aβ40 and Arctic Aβ42. Both Arctic Aβ40 and Arctic Aβ42 will much more easily assemble into higher molecular structures i.e. protofibrils. Thus, the pathogenic mechanism of the Arctic mutation suggests that the soluble higher molecular protofibrils are causing AD and contains a specific unique epitope i.e. "the AD disease epitope".

In the Alzheimer's disease (AD) brain, extracellular amyloid plaques are typically found in parenchyma and vessel walls. The plaques are composed of amyloid (Aβ38-43 amino acid long hydrophobic and self-aggregating peptides, which gradually polymerize prior to plaque deposition. The soluble AD oligomeric species have been proposed to be better disease correlates than the amyloid plaques themselves (McLean et al., 1999; Näslund et al., 2000). Among these pre-fibrillar intermediate Aβ species, oligomeric forms have been shown to elicit adverse biological effects both in vitro and in vivo (Walsh et al., 2002) and may thus play a central role in disease pathogenesis. Several oligomeric Aβ species of various molecular sizes are known. Importantly, the conformation of monomeric, oligomeric and fibrillar forms of Aβ are different and can be targeted by conformational selective antibodies. The identity of the main Aβ pathogen is unclear, although some evidence suggests high-molecular weight Aβ oligomers to be especially neurotoxic (Hoshi et al., 2003).

Pathogenic mutations in the amyloid precursor protein (APP) gene, causing early onset AD have been described. One of them, the Swedish APP mutation (Mullan et al., 1992), causes increased levels of Aβ. The other the Arctic APP mutation (E693G) located within the Aβ domain, was found to enhance the formation of protofibrils, large Aβ oligomers, suggesting these Aβ intermediates to be particularly pathogenic ((US 2002/0162129 A1; Nilsberth et al., 2001). The identification of the Arctic APP mutation and the elucidation of toxic effects for Aβ protofibrils have increased the focus on Aβ oligomers in AD pathogenesis.

Active immunization as a therapeutic strategy for Alzheimer's disease was first reported by (Schenk et al. 1999). The target for the immunization strategy was the fibrillar form of Aβ found in Alzheimer plaques. A recent clinical phase I/II trial of active Aβ vaccination using fibrillized Aβ as a vaccine (AN-1792) had to be halted because of the development of meningoencephalitis in a small number of patients (Bayer et al., 2005). The side effects seen in this study were likely caused by anti-Aβ antibodies reacting against fibrillar amyloid in vessel walls. The fibrillary amyloid in CAA is in close proximity to the blood-brain-barrier (BBB) and the antigen-antibody reaction could thus generate damage to the BBB leading to infiltration of T-lymphocytes into the CNS (Pfeifer et al., 2002; Racke et al., 2005). Moreover, only a minority of the participating patients displayed an immune response to the Aβ vaccine. Although the study ended prematurely, it seems to imply that active Aβ immunization may be beneficial only to a subset of AD patients.

Monoclonal antibodies selective for human Aβ protofibrils have been described (US 2002/0162129 A1). The method to generate highly pure and stable human Aβ protofibrils, involves the use synthetic Aβ42 peptides with the Arctic mutation (Glu22Gly). The mutation facilities immunization and hybridoma screening for Aβ protofibril selective antibodies. Importantly, these antibodies bind both wild-type Aβ protofibrils and Aβ-Arc protofibrils (PCT/SE 2005/000993).

Antibodies that are selective towards other conformations of Aβ such as Aβ fibrils (O'Nuallain 2002), micellar Aβ (Kayed 2003), ADDL (Lambert 2001), have been described. However, non of these are Aβ protofibril selective.

SUMMARY OF TILE INVENTION

The present invention pertains to improved antibodies i.e. high affinity (less than $10^{-7}$ M) Aβ protofibril selective antibodies of class IgG and subclass IgG1 or IgG4 or combination thereof or mutations thereof, with reduced risk of inflammation, for improved prevention, treatment and diagnosis of Alzheimer's disease, Downs syndrome or other neurodegenerative disorders. Said antibodies have been developed by classical hybridoma techniques and antibody engineering.

The invention discloses the consensus amino acid sequence of the CDR1-3 regions on the VL and VH chains from antibodies that selectively bind oligomeric Aβ forms, i.e. Aβ protofibrils constituting the "Alzheimer disease epitope", combined with modifications of the Fc region to reduce complement factor C1q binding, reducing the risk for complement activation and inflammation.

The constant region of an antibody has many important functions notably binding Fc-receptors and complement factor C1q. The latter function has been inactivated to avoid inflammatory reactions.

In summary, this type of high affinity protofibril selective antibodies have the following distinct advantages as compared to other known immunotherapeutic treatment modalities:
1) targets disease causing Aβ protofibrils with high affinity
2) reduces the risk for inflammatory side-effects i.e. meningioencephalitis, by low or no binding to complement factor C1q
3) high affinity antibody reduces the clinical dose needed for an effective treatment
4) provides a modality of accurate dosing
5) less binding to Aβ fibrils in the blood vessel wall i.e. CAA, reducing the risk for inflammatory side-effects.
6) Less antibody is bound in the periphery, thus more will cross the blood brain barrier and be available for binding and elimination of Aβ oligomeric forms in the brain.

One aspect of the invention is the discovery of the antibody consensus amino acid sequence of the CDR regions that bind human wild type Aβ protofibrils (Example 1). This discovery defines the binding sites (CDR regions) that confer high affinity and high selectivity for wild-type human Aβ protofibrils for use as therapeutics or diagnostics. The basic structure of an immunoglobulin (IgG) molecule comprises two identical light chains and two identical heavy chains linked together by disulphide bridges (FIG. 1). The light chain, which is either lambda or kappa, has a variable region (VL) and a constant region (CL) of approximately 110 amino acid residues each. The heavy chain has a variable region (VH) of about 110 amino acid residues, but a much larger constant region (CH) of 300-400 amino acid residues, comprising CHγ1, CHγ2 and CHγ3 regions or domains.

The constant region (Fc) activates the complement system and binds to a Fc receptor on macrophages, microglia and neutrophiles, which ingest and destroys infecting microorganisms or foreign/non-self antigens. This function is particular important since it is part of the therapeutic principle of the antibody, i.e. Fc receptor mediated microglial phagocytosis and clearance of Aβ protofibrils. Other antibody mediated clearance mechanisms are also operating, i.e. anti-aggregation properties of Aβ antibodies and clearance of Aβ protofibrils in the periphery, according to the sink hypothesis. The variable region of the heavy and light chains contains 3 hyper variable regions called complementary determining regions or CDRs. The CDR regions are short stretches of about β-23 amino acid long, located in the VL and VH regions. The six CDRs regions on one "arm" of the antibody forms the "pocket" that binds the antigen. FIG. 1 shows the basic structure of an IgG immunoglobulin and its subdomains.

Another aspect of the invention pertains to protofibril selective antibodies of high affinity. Affinities in the range of $10^{-7}$M preferably $10^{-8}$ M, even less than $10^{-9}$M, less than $10^{10}$ M, or less than $10^{-11}$M for protofibrils are described (Example 2). These antibodies have the advantage that they can be administered at lower doses compared to antibodies with affinities in the $10^{-6}$ M range. This has significant clinical advantage in that these high affinity antibodies, which are administered by injection, can be given subcutaneously since only a low amount of the antibody is needed to achieve efficacy. Administration modalities are not limited to subcutaneous injections. Furthermore, the lower doses needed for efficacy will reduce cost of goods for production of the antibody.

Another aspect of the invention is that the antibodies are of IgG class, suitable for therapeutic use since it can pass over the blood brain barrier. Clearance of Aβ protofibrils in the brain parenchyma is achieved by Fc receptor mediated phagocytosis by microglia cells. Other anti-Aβ clearance mechanisms are likely to operate as well. This clearance of soluble Aβ protofibrils is a central mechanism of the treatment. Aβ protofibrils are considered highly neurotoxic, initiating and driving the disease process. Clearance of Aβ protofibrils in the brain is of significant clinical value. In addition to clearance of Aβ protofibrils, other Aβ oligomeric forms including Aβ fibrils, will be reduced indirectly via removal of Aβ protofibrils since different Aβ aggregated forms, i.e. dimers, trimers, tetramers and higher oligomeric forms including protofibrils and fibrils, are in equilibrium. Example of reduction of plaques, which contain Aβ fibrils, is shown in a Alzheimer transgenic mouse model (APPswe) after 72 hour treatment with a high affinity protofibril selective antibody (mAb 158) (Example 3). Hence, clearance of Aβ protofibrils by said antibody will also have the advantage to indirectly reduce other Aβ aggregated or oligomeric forms.

Yet another aspect of the invention is a high affinity human Aβ protofibril selective antibody of subclass IgG1, which has a high affinity for human FcγRI receptors present on microglial cells in the brain. A high affinity antibody will lead to efficient clearance of Aβ protofibrils which will be of significant therapeutic value. Hence, the antibodies will exhibit clearance of Aβ protofibrils, both in CNS and periphery as compared to other immunotherapeutic strategies such as active vaccination or monoclonal antibody treatments with other monoclonal antibodies of IgG1 subclass targeting other Aβ forms. Importantly, the treatment will be efficient early in the disease process when toxic soluble Aβ spices such as Aβ protofibrils are present at elevated levels but also later in the disease process. Elevated levels of oligomeric Aβ forms have been described in a transgenic mouse model exhibiting the Swedish and Arctic mutations APP swearc (Lord A. et al. 2006). Yet another aspect of the invention is that the high affinity Aβ protofibril selective antibodies can reduce or inhibit Aβ aggregation thereby reducing levels of soluble oligomeric Aβ forms in the brain.

Yet, another aspect of the invention is that the high affinity Aβ protofibril selective antibodies can bind oligomeric forms of Aβ, i.e. Aβ protofibrils outside CNS as well, thereby shifting the equilibrium of said Aβ forms over the blood brain barrier in such a way as to lower CNS levels of said Aβ forms (drainage).

As discussed above, the Elan clinical study using an Aβ vaccine (AN-1792) selective for Aβ fibrils to treat Alzheimer patients resulted in a side-effect, i.e. meningioencephalitis, in 6% of the cases. The strategy to target Aβ fibrils, that are the core of amyloid plaques present in the brain parenchyma but importantly also in the blood vessel walls, resulted in severe side-effects. The side-effects was most likely caused by the binding of the antibodies to CAA (Cerebral Amyloid Angiopathy) in the blood vessel walls of the brain, starting an inflammatory process. This significant clinical problem is avoided by the improved high affinity protofibril selective antibodies with reduced complement activation activity. These antibodies will retain high clearance efficacy of Aβ protofibrils reduced risk of side-effects, i.e. meningioencephalitis.

Another aspect of the invention is that the high affinity protofibril selective antibodies have low Aβ fibril binding (See example 2), reducing the risk for side effects, by less binding to Aβ fibrils present in CAA.

Yet another aspect of the invention is that the high affinity Aβ protofibril selective IgG antibodies are engineered to reduce complement factor C1q binding to the CH2 domain of IgG1 and reduce complement activation and risk of inflammation. This modification can be done in several different ways. One way is to make a chimeric antibody where the CHγ2 domain of the IgG1 constant region has been deleted and exchanged for the corresponding domain from IgG4 or part of the domain that confers C1q binding. It is well established that IgG4 does not bind C1q and hence does not activate the complement cascade. To achieve this the constant region of the heavy chain (CH) is engineered is such a way as to combine the high affinity Fc-receptor domain (CHγ3) on IgG1 with the IgG4 domain (CHγ2) which has no binding for the complement factor C1q. This new antibody containing the chimeric constant heavy chain (IgG1:CHγ1, CHγ2:IgG4, CHγ3:IgG1) will have the important properties of both efficient clearance of Aβ protofibrils through Fc-receptor mediated phagocytosis and reduced risk for side-effects, i.e inflammation such as meningioencephalitis.

Yet another way of reducing the risk of inflammation is to alter the oligosaccharides structure of the antibody which will reduce complement factor C1q binding and complement activation. 30 different structures of the complex biantennary oligosaccharides at Asn-297 in human IgG1 has been described. The absence of CH2 associated carbohydrates is believed to cause a conformational change in the "hinge" region of the antibody, reducing interaction efficacies with effector molecules and loss of complement activation function and C1q binding.

The modification of a high affinity human Aβ protofibril selective antibody by site-directed mutagenesis of Asn-297 to any other amino acid will generate an antibody of retained Fc-receptor binding with less C1q binding and hence reduced risk of inflammation in particular at the blood brain barrier. An alternative to modify the glycosylation on the antibody is to expressing the antibody in a cell type where the enzyme N-acteylglucosaminyl-transferase I has been inactivated. This will yield an antibody with altered carbohydrate structure at Asn-297. A structure of $Man_5GlcNAc_2$, but not limited to this structure, is formed. This carbohydrate modification will reduce complement factor C1q binding and inhibit inflammation (Wright at al. 1998). Alternatively, glycosylated protofibril selective antibodies can be achieved by culturing cells expressing antibodies in the presence of tunicamycin, which inhibits glycosylation. These antibodies will have altered complement activating activity as well as altered Fc-receptor function (Leatherbarrow et al. 1985). Screening of clones expressing antibodies with low complement activation and high Fc-receptor binding will generate protofibril selective antibodies that exhibit high Fc-mediated clearance of Aβ protofibrils and low C1q binding.

Yet another aspect of the invention is a high affinity human Aβ protofibril selective antibody, of IgG1 subclass, where the complement factor C1q binding site has been modified, i.e. Pro331>Ser331 (Xu et al. 1994), in such a way as to reduce or inhibit binding of complement factor C1q, for the treatment or prevention of AD. The proline residue at position 331 in human IgG1 can also be changed to a threonine or glycine or any other polar amino acid. This modification can be achieved by standard molecular biology techniques such as site-directed mutagenesis or DNA deletions.

Yet another aspect of the invention is the use of high affinity human Aβ protofibril selective IgG antibodies to specifically determine protofibril levels in human tissues, in particular in cerebrospinal fluid, blood, urine or saliva as a diagnostic tool or biomarker for Alzheimer's disease. Levels of human Aβ protofibrils in CSF or blood are likely to be different as compared to a matched elderly control group not having Alzheimer's disease. A person who is developing Alzheimer's disease is likely to have increased levels of Aβ protofibril levels in CSF or blood. Hence, by determination of Aβ protofibril levels in CSF or blood an early diagnosis of the disease can be made. This is possible to achieve with the new high affinity Aβ protofibril selective antibodies in combination with a sandwich ELISA method (Example 2A), where Aβ protofibrils have been determined down to 10 pM level. Interference of other Aβ forms such as Aβ fibrils, Aβ monomers and Aβ fragments (1-16; 17-40) in the assay, is 10% or less.

The invention further pertains to the use of a high affinity protofibril specific antibodies for determinations of Aβ protofibrils in human and animal tissues, for example, cerebrospinal fluid, blood, serum, urine and brain tissue but not limited to these tissues, providing for a possible diagnostic method for Alzheimer's disease. Suitable methods for assaying Aβ protofibrils in these tissues as well as in cell cultures using an anti-Aβ protofibril antibody are immunoassays such as ELISA, RIA, Western blotting or dot blotting. The method would be suitable to follow treatment efficacy (protofibril reduction) in clinical trials and suitable as a diagnostic test for Alzheimer's disease or Down's syndrome.

Since Aβ protofibrils levels are very low in CSF and blood, a high affinity Aβ protofibril selective antibody is needed in a diagnostic test based on an ELISA method, to be able to measure low levels of Aβ protofibrils. Other supersensitive methods such as proximity ligation (Example 4) (Gullberg 2004) or similar amplification systems or Biacore or similar techniques, can be used to increase sensitivity. The proximity ligation technique is based on the discovery that different antibodies, raised against different epitopes on an analyte (in this case a protein), may bind near each other on said analyte. If said different antibodies are conjugated to oligonucleotides, the distance between said oligonucleotides will be short enough for a connector oligonucleotide, with the aid of ligation components, to form a bridge between the oligonucleotides. Amplification components are also added, upon which RT-PCR may be performed. By this principle, an amplifiable DNA sequence, reflecting the identity and amount of the target protein, is generated. This technique makes it possible to obtain an enhanced signal response and thus to detect lower concentrations of analyte.

The present inventors surprisingly discovered that a modified proximity ligation technique may also be used with their Aβ protofibril-specific antibodies, to detect low concentrations of larger Aβ peptide structures, i.e. Aβ protofibrils but not Aβ monomers. They discovered that the Aβ peptides, in the protofibril conformation, exhibits a structure (repetitive units) that makes it possible for two antibodies, according to the present invention, to bind sufficiently near each other on the protofibril. If said antibodies are conjugated to oligonucleotides, said oligonucleotides may be bridged using a connector oligonucleotide. PCR is performed using amplification components. By this principle, an amplifiable DNA sequence, reflecting the identity and amount of the target protofibril, is generated (see FIG. 4A).

Proximity ligation or a version of the technique called "rolling circle", is a highly sensitive technique and particularly well suited for detection of polymeric structures with repeated sequences, such as Aβ protofibrils to be used for diagnosis of Alzheimer's disease and other neurodegenerative disorders.

The invention further pertains to the use of high affinity protofibril specific antibodies in imaging for detection, localization and quantitation of Aβ protofibrils in human and animal tissues. The antibody could be label with a radioactive ligand such as $I^{131}$, $C^{14}$, $H^3$ or $Gallium^{68}$, but not limited to these radioisotopes, for detection purposes. The method will be suitable as a diagnostic tool for Alzheimer's disease or Down's syndrome.

Yet another aspect of the invention is to make the antibody spices specific for use in veterinary medicine. The diagnostic methods outlined are also suitable for veterinary use.

Another aspect of the invention is the humanization of said antibodies to avoid side-effect, i.e. to avoid an immunoresponse against said antibodies in humans when used as a therapeutic or diagnostic agent.

Yet another aspect is a formulation of the antibody in a physiological buffer, for example PBS but not limited to PBS, suitable for administration to humans and animals. The antibody product can be freeze dried for better stability. The freeze dried formulation can contain an excipient such as manitol but not limited to manitol to stabilize the product after freeze drying.

The antibody product can contain an antibacterial agent.

The antibodies or fragments according to the inventions may exhibit amino acid deletions, substitutions and insertions within said CDR regions and/or its framework. Inserted or substituted amino acids may also be amino acid derivatives, with the proviso that the affinity and specificity of the antibody is still intact.

BRIEF DESCRIPTION OF THE DRAWINGS

FIG. 2 shows characterization of a high affinity protofibril selective monoclonal antibody using a sandwich ELISA (A) and a competitive ELISA (B).

FIG. 3 shows the therapeutic efficacy of a high affinity protofibril selective antibody in a transgenic mouse model.

FIG. 4 shows human Aβ protofibrils measured at pM levels by the proximity ligation technique.

FIG. 8 shows the Aβ protofibril levels in $APP_{Swearc}$ transgenic mouse brain TBS extracts after 4 months treatment with either mAb 158 or placebo.

FIG. 9 shows the total Aβ levels in $APP_{Swearc}$ transgenic mouse brain formic acid extracts after 4 months treatment with either mAb158 or placebo.

FIG. 10 shows the pKN100 vector.

FIG. 11 shows the pG1D200 vector.

FIG. 12 shows Aβ monomer binding by chimeric and mouse 158 antibodies.

FIG. 13 shows competition of monomeric or protofibrillar Aβ for binding to chimeric 158 or mouse 158 antibody.

FIG. 14 shows competition of monomeric or protofibrillar Aβ for binding to chimeric 158 or mouse 158 antibody.

EXAMPLES

Figure 1:
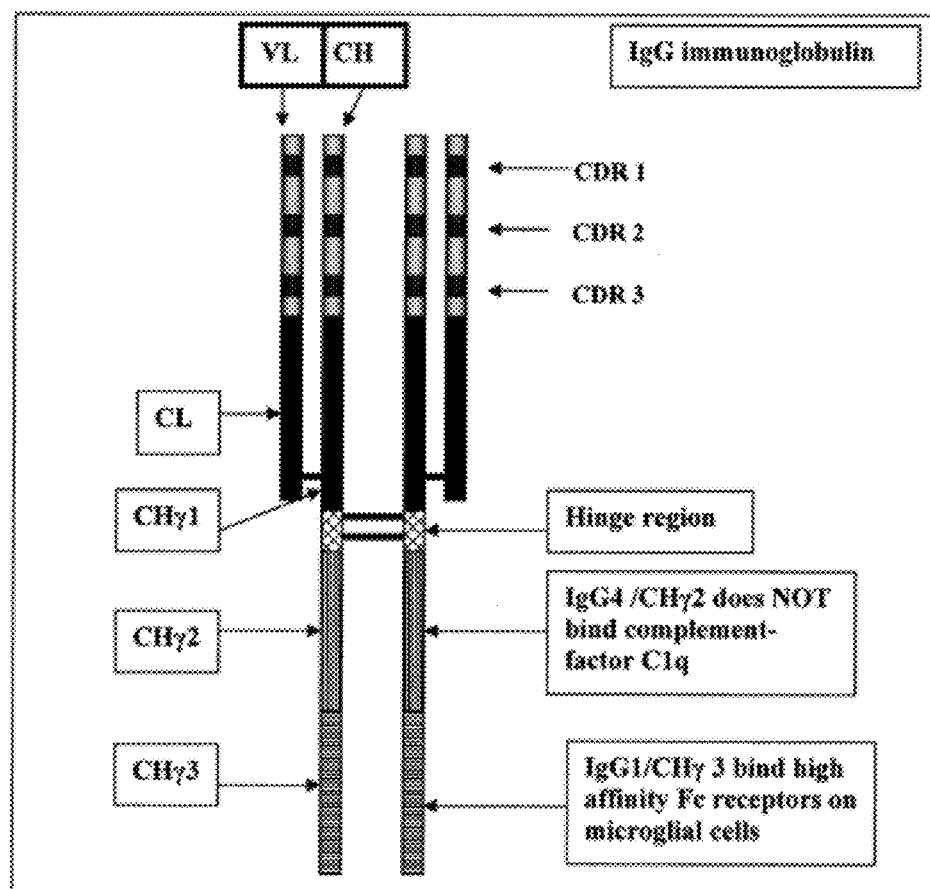
FIG. 1 shows the basic structure of an immunoglobulin molecule.

The following examples are provided for illustration and are not intended to limit the invention to these specific examples.

Example 1

Human wild-type Aβ protofibril selective monoclonal antibodies were cloned and sequenced. The amino acid sequence of the variable heavy chain region (VH) and the variable light chain region (VL) are shown in Table 1. The positions of the CDR regions 1-3 are underlined and shown as well in Table 2 and 3. The amino acid sequences of the CDR regions form the structural basis for binding human wild-type Aβ protofibrils constituting the "Alzheimer disease epitope".

The amino acid sequence of the CDR regions 1-3 of the VL and VH chains for a high affinity protofibril specific antibody BA9/158 is shown in Table 1, 2 and 3. Sequencing data of other protofibril selective antibodies (BA2, BA3, BA4 and BA7) provide alternative amino acids sequences of the CDR regions but not limited to these. The combined amino acid sequences of the CDR1-3 regions of the VH and VL chains create the molecular "pocket" which binds human Aβ wild-type protofibrils with high affinity and specificity. This "pocket" forms the structural basis of the "Alzheimer's disease epitope". Variations in the CDR amino acid sequence length are observed in both the VH chain and the VL is compatible binding to human Aβ protofibrils (Table 2 and 3). A shorter CDR region provides a more restricted three dimensional structure of the binding pocket of the antibody, whereas a longer is more flexible.

We claim the CDR sequences as shown in Tables 1, 2 and 3 as well as amino acid sequences in the "mouse framework" regions of the VH and VL chains, i.e. outside the CDR regions as well as the human VL and VH framework regions for protofibril specific antibodies as shown in Table 4 and 5, but not limited to those.

The amino acid sequence of the framework region of VL and VH regions 1-3 of the VL and VH chains from a high affinity protofibril specific antibody BA9/158 is shown in Table 4 and 5.

Other amino acid substitution in the CDR regions than what is shown in Table 1, 2 and 3 are compatible with high affinity and high specificity binding to human wild-type Aβ protofibrils. Where a polar amino acid is present in a particular position in a CDR region that particular amino acid can be substituted by another polar amino acid, with retained or improved high affinity and specificity binding to Aβ protofibrils. Likewise, if a non-polar or negatively or positively charged amino acids is present at a certain position, that amino acid can be substituted for by a similar amino acid from the same group.

Also, a particular amino acid or amino acids are exchanged in any position in the CDR regions by functional equivalents that confers a similar function and structure to the antibody.

Example 2

Characterization of an High-Affinity Human Aβ Wild-Type Profibril Selective Monoclonal Antibody by ELISA Example 2 shows a high affinity protofibril selective antibody that cross-reacts a 200-1000-fold less with Aβ monomers and less than 40-fold with Aβ fibrils, as measured by a sandwich ELISA (FIG. 2A). From competitive ELISA experiments, the antibody has a strong affinity for human Aβ42 wild-type protofibrils, but only very weak affinity for the N-terminal part of the Aβ peptide and Aβ monomers. No binding was observed to the C-terminal fragment of Aβ (FIG. 2B). Furthermore, the antibody does not cross-react with other types of amyloids, like medin or transthyretin. Furthermore the antibody does not recognize human APP, the abundant precursor of Aβ.

In FIG. 2A a sandwich ELISA is shown. Antibody 158 was coated in the wells and different Aβ forms subsequently added to the well in increasing concentrations.

Measurement of bound Aβ forms was made by adding biotinylated mAb 158 and HRP labelled Streptavidine. Colour development was measured according to the procedure recommended by the manufacturer.

In FIG. 2B a competitive ELISA is shown. An ELISA plate was coated with human Aβ protofibrils. Antibody 158 was subsequently incubated with increasing amounts of different Aβ forms (competition). The incubation mix was added to the microtiter plate wells and free antibody was allowed to bind to immobilized protofibrils in the wells. Bound 158 antibody was measured by a second antibody using standard procedures.

Example 3

The efficacy of high affinity Aβ protofibril selective antibody was determined in an Alzheimer transgenic mouse model (APPswe) by an acute intracranial injection. Transgenic mice used for efficacy evaluation express human APP, with the Swedish mutation ($APP_{Swe}$). In this paradigm, antibodies are injected directly into plaque-rich regions of the brain parenchyma and effects on neuropathology are assessed after 72 hours (Wilcock et al., 2003). Other studies have shown that the direct application of anti-Aβ antibodies results in a rapid clearance of amyloid deposits in vivo (Bacskai et al., 2001; Brendza et al., 2005). The injection of high affinity Aβ protofibril selective antibody leads to a significant plaque reduction in the $APP_{Swe}$ mouse model (FIG. 3).

In FIG. 3 the therapeutic efficacy of a high affinity protofibril selective antibody in transgenic mouse model (APPswe) was tested. A: A 14 months old APPSwe transgenic mouse was intracranially injected with PBS and B: high affinity protofibril selective antibody (158) at 1 μg/μl and examined 72 hours following injection. Marked clearance of Aβ burden is noticeable in the subiculum close to the injection site (B; arrow) as compared to the control side (A; arrow).

Example 4

Proximity ligation in combination with high affinity protofibril selective antibody for measurement of Aβ protofibrils. Human wild-type Aβ protofibrils were detected down to 10 pM-range whereas the Aβ monomer preparation were not detected at all. The combination of the hypersensitive proximity ligation method and a high affinity antibody is particularly advantageous since it provides a system to determine only oligomeric forms of the analyte, which is particularly suitable when diagnosing Alzheimer's disease and other protein "aggregation" diseases such as prion disease, Creutzfelt-Jacob, amyloidosis and Parkinson's disease.

In FIG. 4 human Aβ protofibrils are measured at pM levels by the proximity ligation technique. Proximity ligation assay: Method description (from Gullberg et al., 2004): Step 1, incubation of sample with proximity probe pair ($\approx$1 h); step 2, addition of all components required for ligation and detection by quantitative PCR ($\approx$15 min ligation time). A high affinity protofibril selective monoclonal antibody was used in the assay; step 3, quantitative PCR ($\approx$2 h). Synthetic Aβ monomer and Aβ protofibril preparations were diluted and tested for their reactivity in proximity ligation assay described above.

Example 5 mAb 158 does not Recognize a Generic Amyloid Epitope

Figure 5:
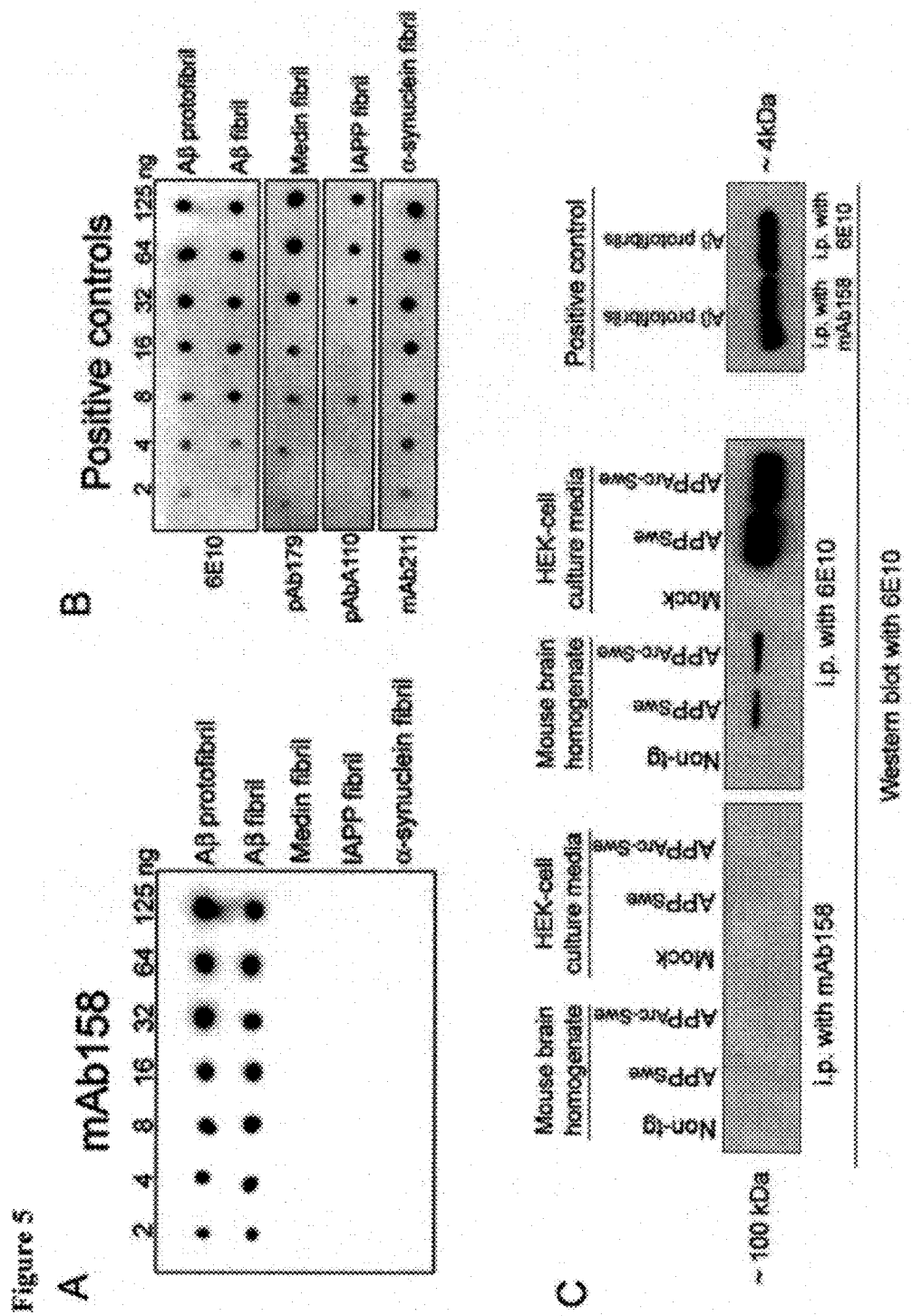
FIG. 5 shows that mAb158 does not exhibit reactivity with any amyloid other than the Aβ fibril (A), positive controls (B), and Western blots with the 6E10 antibody (C).

Previously reported Aβ conformation dependent antibodies have been shown to bind oligomers and fibrils of other amyloidogenic proteins, suggesting a common epitope present on all amyloid aggregates. Due to technical difficulties in generating protofibrils from other amyloidogenic proteins than Aβ, mAb158 was instead tested against different amyloid fibrils. The dot blot assay was used for these experiments since inhibition ELISA, where the antibody-antigen reactions take place in solution, is not suitable for insoluble antigens like fibrils. The dot blot assay is however not suitable for evaluation of antibody specificity for various Aβ forms, i.e. for measuring differences in selectivity for profibrils and fibrils. Fibrils of medin, islet amyloid polypeptide (IAPP) and α-synuclein were immobilized on a nitrocellulose membrane to maintain their native conformations. mAb158 did not exhibit reactivity with any amyloid other the Aβ fibril (FIG. 5A). The binding of mAb 158 to Aβ fibrils suggests that part of the Aβ protofibril epitope is present also in the Aβ fibril structure. As positive controls the antibodies 6E10 (Aβ), pAb179 (medin), pAbA110 (IAPP) and mAb211 (α-synuclein) were used (FIG. 5B). Representative blots from repeated experiments (n=3).

mAb158 does not Bind APP

Levels of APP and soluble APP fragments commonly exceed the levels of β in biological samples such as CSF and brain homogenate, and therefore an Aβ-antibody's cross-reactivity to APP could inhibit a treatment by binding to APP, resulting in less free antibody for binding and elimination of Aβ protofibrils and/or Aβ oligomers. Also, it could disturb measurements of Aβ protofibrils in biological samples by a sandwich ELISA assay of Aβ. To elucidate whether mAb158 binds to native APP, immunoprecipitation experiments were performed. HEK-cell culture media (mock, $APP_{Swe}$ and $APP_{Arc-Swe}$) and mouse brain homogenates (non-transgenic, $APP_{Wwe}$ and $APP_{Arc-Swe}$) were immunoprecipitated with mAb158 or 6E10, followed by a denaturing Western blot with 6E10 as detecting antibody (FIG. 5C).

As seen in FIG. 5C, mAb158 did not immunoprecipitate αAPPs from cell culture media or full length APP from mouse brain homogenates, whereas, as expected, 6E10 did. The synthetic Aβ protofibrils used as control were immunoprecipitated equally well by both antibodies (FIG. 5C). Representative blots from repeated experiments (n=3).

Example 6

Establishment of an Aβ Protofibril Specific Sandwich ELISA

Figure 6:
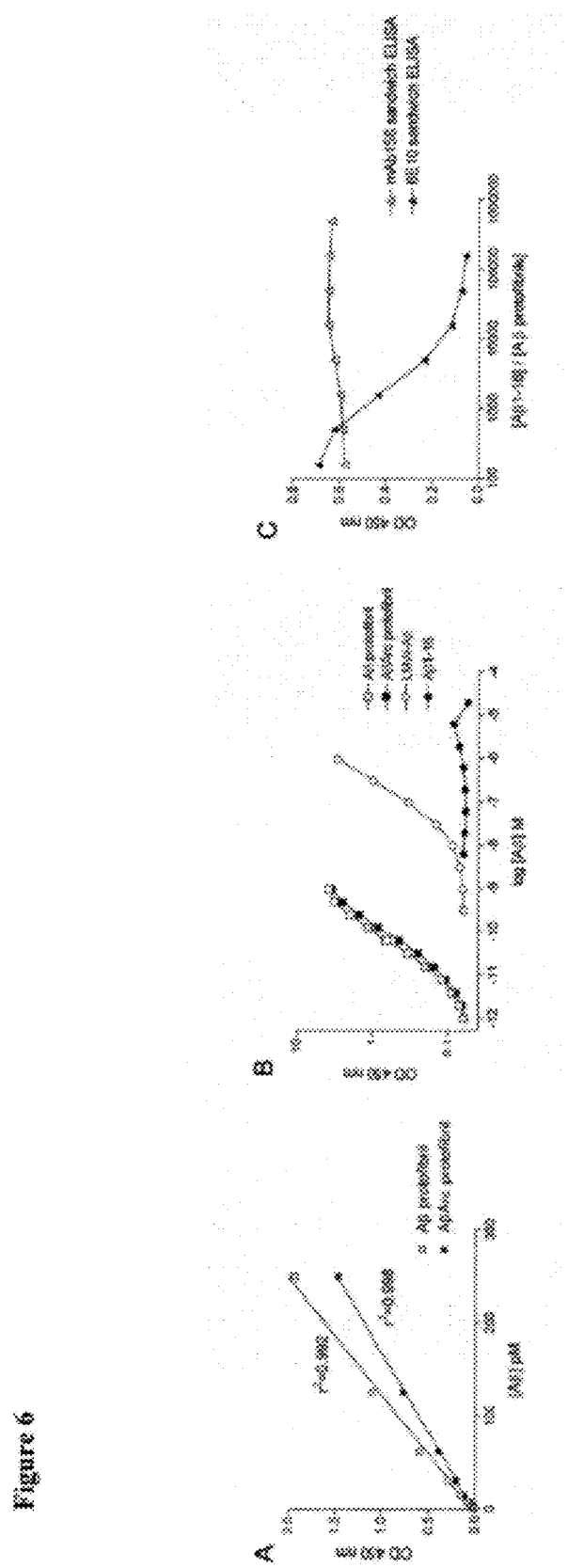
FIG. 6 shows assays measuring Aβ protofibrils.

To enable measurements of Aβ protofibrils in biological samples a sandwich ELISA with mAb158 as both capturing and detecting antibody was established. This assay measures Aβ protofibrils with a detection limit of 1 pM and with a linear range up to 250 pM (FIG. 6A, lines indicate linear regression of the standard curves). Due to uncertainties concerning the size of the Aβ protofibrils used in the standard curve, the concentration 1 pM is based on the molecular weight of one Aβ monomer (4514 g/mol), Though, since the molecular weight of a protofibril has been estimated to be at least 100 kDa, the limit of detection calculated as molar Aβ protofibrils could be as low as 50 fM. A standard curve of AβArc protofibrils gave a lower signal than wild type Aβ protofibrils, possibly due to differences in Aβ protofibril size (FIG. 6A, 6B). Titrated synthetic LMW-Aβ (Low Molecular Weight Aβ). By the term "Low Molecular Weight Aβ", it is meant monomers, dimers and trimers of Aβ having a molecular weight of approximately 4-12 kDa. Aβ protofibrils and Aβ1-16 were used to validate the conformation specificity of the ELISA (FIG. 6B), where the hydrophilic Aβ1-16 peptide was used since it is not expected to aggregate. An ELISA composed of two identical antibodies requires at least a dimer of a protein to produce a signal and as predicted, Aβ1-16 was not detected with the mAb158 sandwich-ELISA even at μM-concentrations (FIG. 6B). When pre-treating the LMW-Aβ and Aβ protofibrils with 70% formic acid (FA), known to dissociate aggregated Aβ into monomers, the sandwich ELISA the signal was lost (data not shown). Hence, the detection of LMW-Aβ at high nM concentrations (FIG. 6B) is probably due to a small aggregate content of the peptide preparation.

A large excess of monomeric Aβ, holoAPP and APP-fragments, naturally occurring in biological samples, could interfere with the Aβ protofibril analysis by occupying binding sites of the capture antibody coat, thus inhibiting the protofibrils from binding. This problem was investigated by adding an increasing excess of Aβ1-16 to a fixed concentration of Aβ protofibrils (50 pM, expressed as monomer units) and analyzing it with both the mAb158 ELISA and a 6E10-6E10 sandwich ELISA (FIG. 6C). A 500 000-fold molar excess of Aβ1-16, as compared to Aβ protofibrils, did not disturb the measurements with the mAb158 sandwich ELISA, as expected since Aβ1-16 binds poorly to the capture antibody. In contrast, a 500 fold excess of Aβ1-16 was enough to decrease the signal in the 6E10-6E10 ELISA, where Aβ1-16 binds with high affinity to the capture antibody (FIG. 6C). Moreover, when synthetic Aβ protofibrils was added to mock HEK cell culture media or non-transgenic mouse brain homogenates, 90% of the signal was recovered (data not shown).

Example 7

Measurement of Aβ Protofibrils in Biological Samples

Figure 7:
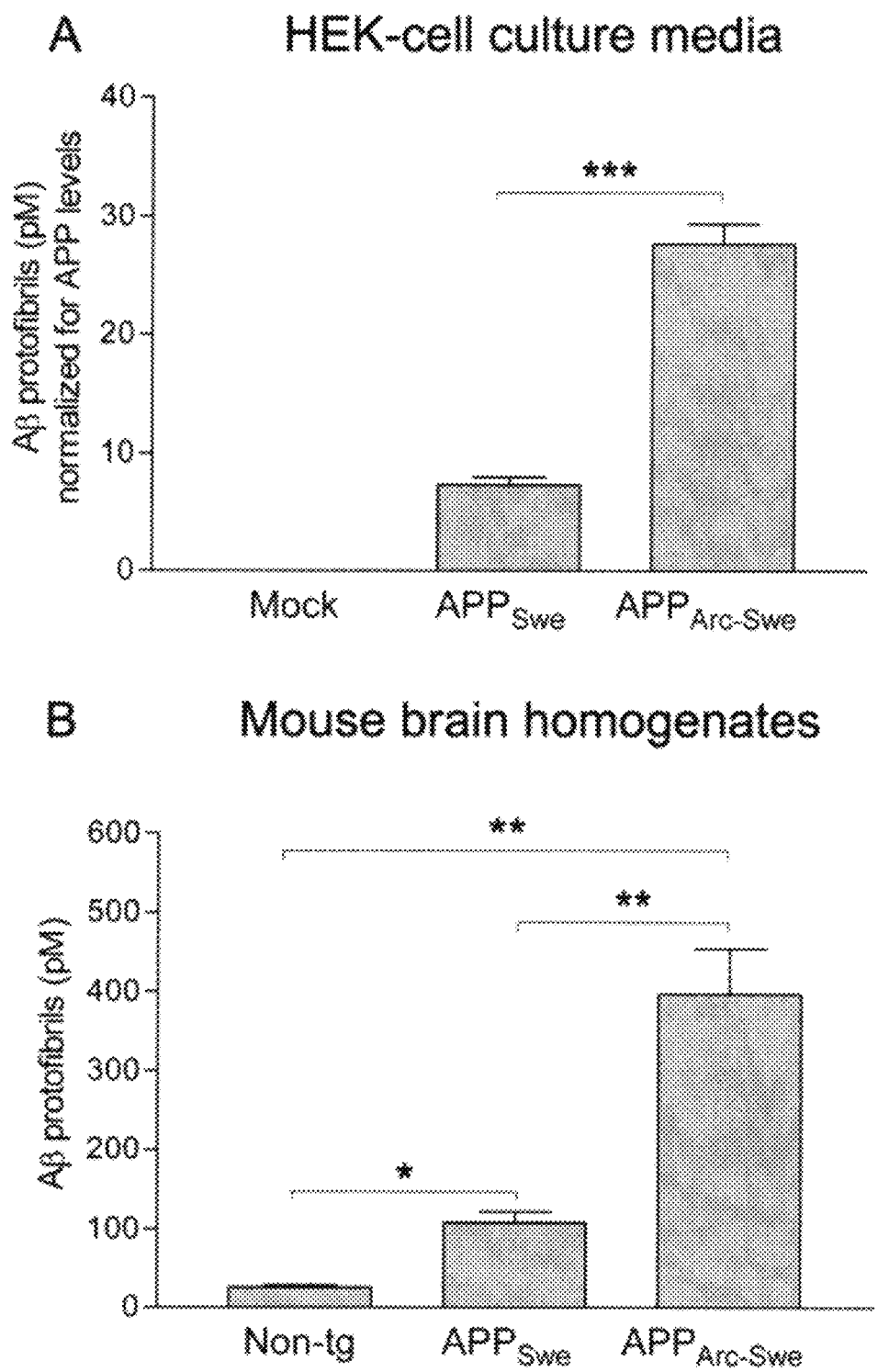
FIG. 7 shows the Aβ protofibril concentration in HEK-cell culture media (A) and in mouse brain homogenates (B).

The presence of Aβ protofibrils in cell and mouse models carrying the Arctic mutation have been suggested, though until now there has been no method for direct assaying of Aβ protofibrils in biological samples. The mAb158 sandwich ELISA therefore provides the first opportunity to measure Aβ protofibril levels in such cell and mouse models and to compare them to models without this intra-Aβ mutation. Samples from cells and mice carrying only the Swedish mutation were compared to the wild type Aβ protofibril standard curve, whereas samples from cells and mice expressing Aβ with the Arctic mutation were compared to AβArc protofibril standard curve (FIG. 6A). To ensure that all Aβ measured in this assay was in a soluble state, and to exclude any possible interference from Aβ fibrils, all samples were centrifuged for 5 min at 17 900×g before analysis. Groups of cell media from transiently transfected $APP_{Wwe}$ and $APP_{Arc-Swe}$ HEK-cells were analyzed and compared to mock HEK-cell culture media. Aβ protofibril levels were calculated from the standard curves (FIG. 6A) as the mean value of triplicates and were then normalized to APP levels to compensate for differences in transfection levels (according to Stenh et al.). The Aβ protofibril concentration in $APP_{Arc-Swe}$ HEK-cell culture media was 28 pM (±2), significantly higher (p<0.0001) than the 8.2 pM (±0.3) seen in $APP_{Swe}$ (FIG. 7A). No Aβ protofibrils could be detected in mock media. Levels of Aβ protofibrils were also measured in brains from 10 months old $APP_{Arc-Swe}$ and $APP_{Swe}$ transgenic mice with both plaques and intraneuronal Aβ pathology (according to Lord et al.). Brains were homogenized in TBS and centrifuged prior to analysis in order to recover the soluble Aβ fraction. Similar to the analysis using cell culture media, Aβ protofibril levels differed significantly (p=0.005) between the groups, with 397 pM (±59) in $APP_{ArcSwe}$ and 108 pM (±14) in $APP_{Swe}$ transgenic mouse brains (FIG. 7B).

In the above-mentioned figures (FIGS. 6 and 7) the number of samples were; mock cells (n=3) and transiently transfected with $APP_{Wwe}$ (n=8) and $APP_{Arc-Swe}$ (n=11). Levels of Aβ protofibrils in $APP_{Arc-Swe}$ media were approximately 9 fold higher than in $APP_{Swe}$ media, whereas mock media gave no signal (A). Measurements of Aβ protofibril levels in the TBS-soluble fraction of non-transgenic mouse brain homogenates (n=6) were compared to transgenic mice ($APP_{Swe}$, n=3, and $APP_{Arc-Swe}$, n=6) (B). Similar to the cell culture media, Aβ protofibril levels of $APP_{Arc-Swe}$ mice were 7 fold higher than in $APP_{Swe}$ mice. Error bars show ±SEM.

Example 8 mAb158 Significantly Lowers Aβ Protofibrils and Total Aβ in APPswearc Transgenic Mice after i.p. Administration mAb158 (12 mg/kg) was injected i.p. once weekly for 18 weeks in 9-10 months old APPswearc mice. After the study, brains were isolated and homogenised in TBS and subsequently centrifuged to sediment insoluble material. The insoluble material was solubilised in formic acid. Hence, two fractions were obtained from mouse brains i.e. a TBS fraction and a formic acid fraction. Aβ protofibril levels in the TBS fractions were determined by an ELISA. A significant reduction of Aβ protofibrils was found in the mAb158 treatment group compared to the placebo group (FIG. 8). FIG. 8 shows the Aβ protofibril levels in APPswearc transgenic mouse brain TBS extracts after 4 months treatment with either mAb158 or placebo.

Total Aβ in the formic acid fraction was determined by an ELISA (the formic acid was used to solubilise all Aβ forms, in order to make all Aβ forms detectable). A significant reduction of total Aβ was observed in the treatment group compared to the placebo group (FIG. 9). FIG. 9 shows the total Aβ levels in APPswearc transgenic mouse brain formic acid extracts after 4 months treatment with either mAb158 or placebo.

Examples 9-11

Abbreviations

A Adenine
Ab protocol AERES biomedical protocol
BHK baby hamster kidney
bp base pairs
C Centrigrade
C Cytosine
CHO Chinese Hamster Ovary
CMF Calcium and Magnesium Free
COS 7 African green monkey kidney fibroblast cell line
dhfr Dihydrofolate-reductase
DMEM Dulbecco's Modified Eagles Medium
DMSO Dimethyl sulphoxide
DNA Deoxyribonucleic acid
ELISA Enzyme linked immuno-adsorbent assay
FCS Foetal Calf Serum
g grams
G Guanine
hr hour
HRP Horseradish peroxidase
IgG Immunoglobulin
K G or T (IUPAC convention)
LSAP Large Soluble Amyloid Product
mAb monoclonal antibody
sec second
min minute
M A or C (IUPAC convention)
MTX Methotrexate
NIMR National Institute for Medical Research (UK)
nm nanometer
OD optical density
PBS Phosphate Buffered Saline
PCR Polymerase chain reaction
R A or G (IUPAC convention)
RT Room Temperature
S C or G (IUPAC convention)
T Thymine
UV Ultra Violet
V variable
V A or C or G (IUPAC convention)
VH Immunoglobulin heavy chain variable region
VK Immunoglobulin kappa light chain variable region
W A or T (IUPAC convention)
Y C or T (IUPAC convention)

Materials

| Equipment | UK Supplier | Catalog Number |
| --- | --- | --- |
| DNA thermal cycler: GeneAmp 9600 | Perkin Elmer | N801-0177 |
| A designated tissue culture laboratory containing a class II microbiological safety cabinet fitted with a UV-lamp | Walker Safety Cabinets Ltd. | N/a |
| Innova ® bench top incubator shaker | New Brunswick Scientific | 4000 |
| Bench top centrifuge | Fisher Scientific | CEK-126-010N |
| CO2-gassed 37° incubator | RossLab plc | HSO-501TVBB |
| Microbiological incubator | Kendro/Heraeus | B6060 |
| Electroporator Model: Gene Pulser II | Bio-Rad Laboratories Ltd. | 341BR-3092 |
| ELISA reader: Microplater Reader 3550 | Bio-Rad Laboratories Ltd. | 3550 |
| Microplate Manager ® 2.2 data analysis software package for Macintosh computer | Bio-Rad Laboratories Ltd. | N/a |
| 96-Well GeneAmp PCR System 9700 | ABI | N8050200 |
| ABI PRISM 310 Genetic Analyzer | Applied Biosystems | 310-00-100/120 |
| T100 surface plasmon resonance detector | Biacore | |

Plastic Consumables

| Article | UK Supplier | Catalog Number |
| --- | --- | --- |
| 175 cm2 tissue culture flask | Sarstedt Ltd | 83.1812.002 |
| 25 cm2 tissue culture flask | Corning Costar | 3056 |
| 30 ml universal container | Sterilin | 128C |
| 75 cm2 tissue culture flask | Sarstedt Ltd | 83.1813.002 |
| Electroporation cuvettes | Bio-Rad Laboratories Ltd. | 165-2088 |
| ELISA plates: Nunc MaxiSorp | Invitrogen Life Technologies | 43945A |
| GeneAmp ™ PCR reaction tubes | Perkin Elmer | N801-0180 |
| Glasstic ® disposable cell-counting slide | Bio-stat Diagnostic | 887144 |
| Nunc inoculating needles | Life Technologies | 254399 |
| tissue culture petri 100 × 20 mm, multi-vent | Helena Biosciences | 93100 |
| tissue culture plate: 6-well + lid | Corning | C3516 |
| tissue culture plate: 24-well + lid | Corning | C3526 |

Immunology and Molecular Biology Reagents

| Article | UK Supplier | Catalog No. | Lot No. |
| --- | --- | --- | --- |
| 1st strand synthesis kit | Amersham Biosciences | 27-9261-01 | 3375313 |
| Advantage ®-HF 2 PCR Kit | Clontech | 639123 | 6040151 |
| Agarose (UltraPure ™) | Invitrogen | 15510-027 | 3019491 |
| Albumin bovine (BSA) | Calbiochem | 126575 | B65755 |
| Ampicillin | Sigma | A-9518 | 63H0992 |
| Apa I | Promega | R636 | 16007003 |
| Themoprime+ DNA Polymerase | Abgene | AB0301 | 014/0103/11 |
| | | | 019/0607/13 |
| | | | 020/1808/13 |
| Bam HI | Promega | R602 | 15851606 |
| BigDye ® Terminator v3.0 Cycle Sequencing Ready Reaction Kit | ABI | 4390242 | 0605143 |
| | | | 0608154 |
| Ethidium Bromide (10 mg/ml) | Sigma | E-1510 | 43H9414 |
| Goat anti-human IgG (Fc fragment specific) antibody | Stratech Scientific | 109-005-098 | 68215 |
| Goat anti-human kappa chain horseradish peroxidase conjugate | Sigma | A7164 | 032K9157 |
| Hind III | Promega | R604 | 16834803 |
| Human IgG1/kappa antibody. | The Binding Site | BP078 | 223729 |
| K-Blue HRP substrate | SkyBio | 308176 | 060823 |
| Oligonucleotides | Sigma | n.a. | |
| PBS Tablets | Sigma | P4417 | 11K8204 |
| QIAGEN Plasmid Maxi Kit (25) | Qiagen | 12162 | 124114870 |
| QIAprep Spin Miniprep Kit | Qiagen | 27106 | 124117906 |
| QIAquick gel purification kit | Qiagen | 28704 | 11549740 |
| QIAquick PCR purification kit | Qiagen | 28106 | G10.1.12 |
| Red Stop Solution (For K Blue) | SkyBio Ltd, | 301475 | 060104 |
| | Qiagen | 74106 | 10916587 |
| Shrimp alkaline phosphatase | USB | 70092Y | 107635 |
| Subcloning Efficiency ™ DH5α ™ Chemically Competent E. coli | Invitrogen | 44 0098 | 1164658 |
| T4 DNA Ligase | Promega | M1801 | 167080 |

-continued

| Article | UK Supplier | Catalog No. | Lot No. |
|---|---|---|---|
| TMB One-Step substrate for HRP | SkyBio Ltd, | KB176 | |
| TOPO-TA Cloning ® kit | Invitrogen | 45-0641 | 1350772 |
| X-Gal | Sigma | B-9146 | 20965701 |

Solutions from National Institute of Medical Research

| Solution name: | Components | Amount |
|---|---|---|
| PBS 'A' Dulbeccos (Ca & Mg Free) | NaCl | 8 g |
| | KCl | 0.2 g |
| | | 1.15 g |
| | | 0.2 g |
| | Na$_2$HPO$_4$ | 1 L |
| | KH$_2$PO$_4$ | |
| | water | |
| LB | Bacto Tryptone | 10 g |
| | Yeast Extract | 5 g |
| | NaCl | 10 g |
| | water | 1 L |
| LB agar | LB | 1 L |
| | Agar (Difco) | 15 g |

Culture Reagents

| Article | UK Supplier | Catalog Number | Lot Numbers | Expiry date |
|---|---|---|---|---|
| DMEM (1X) Dulbecco's Modified Eagle Medium (High glucose) with GlutaMAX ™ I, 4500 mg/L D-Glucose, Sodium Puruvate | Invitrogen | 41966-047 | 9206 | July 2007 |
| DMSO (Dimethyl sulfoxide) | Sigma | D2650 | 125K2409 | December 2007 |
| Penicillin & Streptomycin | Invitrogen | 15070-063 | 1298401 | |
| Serum: Fetal Clone I | Perbio Science | SH30080 | AMM17779 | December 2007 |
| SOC | Invitrogen | 15544-034 | 1306051 | |
| Trypan Blue | Sigma | T8154 | 19H2388 | |
| Trypsin-EDTA solution, cell culture tested, 0.25% | Sigma | T4049 | 48K2342 | April 2008 |

Example 9

DNA Sequence of 158 Antibody 9.1—RNA Preparation

Snap-frozen cell pellets of the mouse hybridoma 158, (labelled vials 060824#158 5×10$^6$ cells) were received by TAG on Oct. 3, 2006. These cells were stored frozen until processing using the Qiagen RNeasy midi kit to isolate RNA following the manufacturers protocol.

9.2 —1" Strand Synthesis

About 5 micrograms of 158 RNA was subjected to reverse transcription to produce 158 cDNA using the Amersham Biosciences 1st strand synthesis kit following the manufacturers protocol—This was repeated to generate 3 independent cDNA products (rounds 1, 2 and 3) in order to obviate DNA mutations due to the RT reaction.

9.3 Cloning of the 158 Immunoglobulin cDNA

Hybridoma 158 cDNA was amplified by PCR in 23 separate reactions. Immunoglobulin kappa chain variable region (VK) cDNA was amplified using 11 VK primers (MKV1-11) in combination with the kappa constant region primer MKC (Table 6). Similarly, immunoglobulin heavy chain variable region (VH) cDNA was amplified by PCR using 12 different VH primers (MHV1-12) in combination with a mix of the four IgG constant region primers (MHCG1/2a/2b/3: Table 7).

The result of the initial set of IgH PCR reactions was the single amplification product using MHV5 primer. None of the other 11 primer pairs gave a PCR product. The product of the PCR reaction primed by the oligonucleotide primers: MHV5+(MHCG1/2a/2b/3 mixture) was ligated into the pCR2.1®TOPO® vector using the TOPO-TA Cloning® kit. The result of the initial set of IgK PCR reactions was two single amplification products using primers MKV1 and MKV2 with MKC. The other 9 primer pairs generated no product. The products of the PCR reaction primed by the oligonucleotide primers: MKV1 or MKV2+MKC were ligated into the pCR2.1®-TOPO® vector using the TOPO-TA Cloning® kit. E. coli TOP10 bacteria transformed with the ligated vector were cloned on LB/ampicillin/X-gal agar plates, by picking onto agar grid and into PCR screening mixture. The cloned plasmid inserts were screened by PCR amplification. The PCR products were gel electrophoresed and clones producing the correct-sized PCR amplification product (500 bp approx) were identified. Overnight cultures (5 ml) of each clone were processed using the QIAprep Spin Miniprep Kit Protocol, to produce DNA plasmid minipreps.

9.4—cDNA Sequence Determination

The complete cycle of RT-PCR, cloning, and DNA sequence analysis was repeated to obtain three completely independent sets of sequence information for each immunoglobulin chain. Plasmid clones from each independent set of RT-PCR reactions were sequenced in both directions using the 1212 and 1233 primers (Table 10). Plasmids were sequenced using the BigDye® Terminator v3.0 Cycle Sequencing Ready Reaction Kit (ABI), cycled on a GeneAmp9600 PCR machine and analysed on an ABI 310 capillary sequencer.

9.5-158 VK DNA Sequence

Sequences of VK clones generated using PCR primers MKV2 and MKC on $1^{st}$ strand cDNAs rounds 1 and 2, were identical to a sterile kappa transcript originating from the myeloma fusion partner such as MOPC-21, SP2 and Ag8. This is a sterile transcript.

Figure 15:
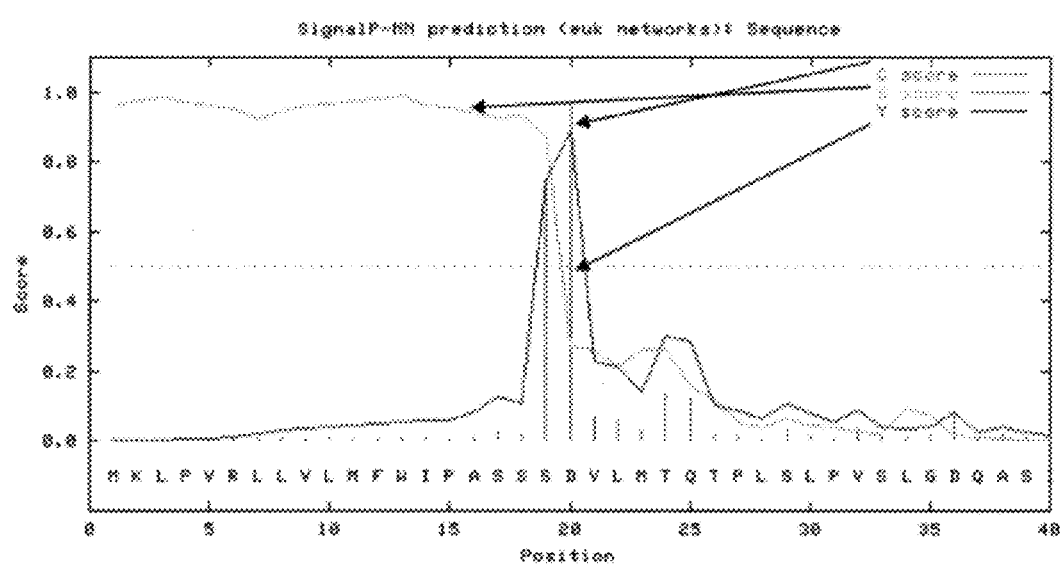
FIG. 15 shows the SignalP algorithm 6 result for the K5.1# leader sequence (SEQ ID NO:103). The SignalP algorithm 6 generates the combination score Y from the cleavage site score C and the signal peptide score S.

The consensus sequence (158 VK) of VK clones generated using PCR primers MKV1 and MKC on $1^{st}$ strand cDNAs rounds 1-3 is shown in Table 11. This is a functional rearrangement. Table 11 shows some differences from the sequence shown in Tables 1, 4 and 5. These differences are in the FW1 region where the PCR primer was located. The mouse VK leader sequence most identical to the fragment of leader in 158 VK, not encoded by our primers, was K5.1# (Table 12). The prediction for the signal peptide to cleave correctly the #K5.1 signal sequence was done by a prediction program. Most likely predicted cleavage site was correctly between amino acid residue 19 and 20. (Table 13; FIG. 15). The chimeric 158VK protein and DNA sequence is shown in Table 14.

9.6-158 VII DNA Sequence

The consensus sequence (158 VH) of VH clones generated using PCR primers MHV5 and MHCG1/2a/2b/3 mixture on $1^{st}$ strand cDNAs rounds 1-3 is shown in Table 15. As with 158 VK, there are some differences from the FW1 sequence shown in Tables 1, 4 and 5. The most identical mouse VH leader sequence to the fragment of leader, not encoded by our primers, was NL-1 (Table 16).

Example 10

Construction of Chimeric Expression Vectors

Construction of chimeric expression vectors entails adding a suitable leader sequence to VH and VK, preceded by a Hin dIII restriction site and a Kozak sequence. The Kozak sequence (Table 8) ensures efficient translation of the variable region sequence. It defines the correct AUG codon from which a ribosome can commence translation, and the most critical base is the adenine at position −3, upstream of the AUG start. The leader sequence is selected as the most similar mouse leader sequence in the Kabat database. These additions are encoded within the forward primers (Table 9). Furthermore, the construction of the chimeric expression vectors entails introducing a 5' fragment of the human γ1 constant region, up to a natural Apa I restriction site, contiguous with the 3' end of the J region of 158. The CH is encoded in the expression vector downstream of the inserted VH sequence but lacks the V-C intron. For the light chain, the natural splice donor site (Table 8) and a Bam HI site is added downstream of the V region. The splice donor sequence facilitates splicing out the kappa V:C intron which is necessary for in-frame attachment of the VK to the constant region.

The mouse VH and VK genes were analysed to identify any unwanted splice donor sites, splice acceptor sites, Kozak sequences and for the presence of any extra sub-cloning restriction sites which would later interfere with the subcloning and/or expression of functional whole antibody. In this case none were found.

10.1—Expression Vectors

Plasmid DNA preparations of the expression vectors pKN100, and pG1D200 were purified using Qiagen Maxi kits following the manufacturers protocol. Plasmid DNA Purification using QIAGEN Plasmid Midi and Maxi Kits, from 500 ml cultures of TOP10 bacteria transfected with either vector. The vector maps are shown in FIGS. 10 and 11.

10.2—The Light Chain Chimerisation Primers

The mouse leader sequence K5.1# was incorporated into the design of the chimeric 158 VK. Primers were designed to generate a PCR product containing this complete leader, and 158 VK, with terminal restriction sites Hind III and Bam HI for cloning into the pKN100 expression vector (Table 9). The forward primer 158v1 introduces a Hind III restriction site; a Kozak site and the K5.1# leader sequence. The back primer 158v1rev introduces: a splice donor site and a Bam HI restriction site.

10.3—The Heavy Chain Chimerisation Primers

The leader sequence NL-1 was incorporated into the design of the chimeric 158 VII. Primers were designed to generate a PCR product containing this leader, and the 158 VH region, with terminal restriction sites Hin dIII and Apa I for cloning into the pG1D200 expression vector.

Figure 16:
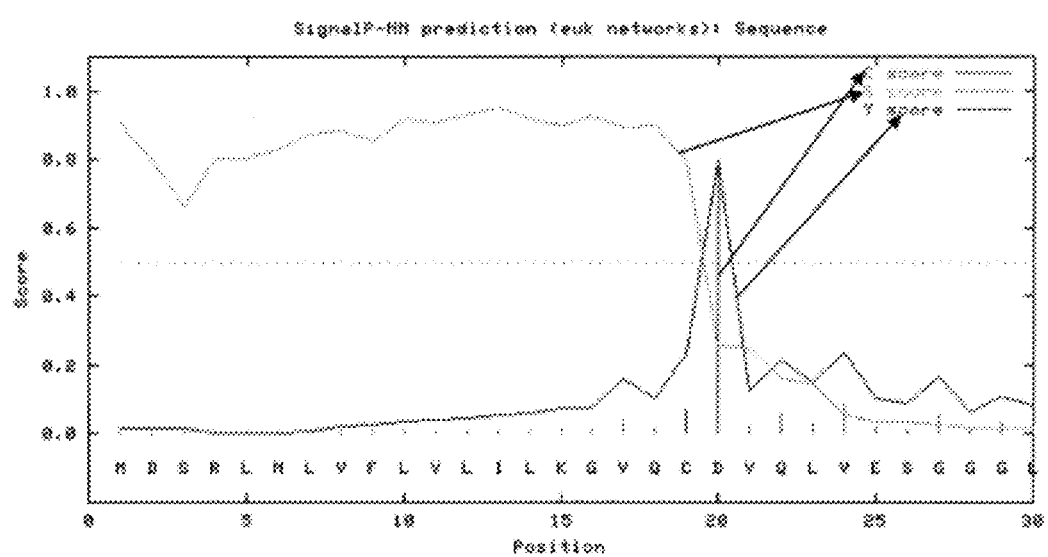
FIG. 16 shows the SignalP algorithm 6 result for the NL-1 HV leader sequence (SEQ ID NO:112). The SignalP algorithm 6 generates the combination score Y from the cleavage site score C and the signal peptide score S.

These are shown in Table 9. The forward primer, 158vh, introduces a Hin dIII restriction site; a Kozak translation initiation site and the NL-1 leader sequence. The back primer, 158vhrev, introduces the 5' end of the γ1 C region and a natural Apa I restriction site. The signal peptide cleavage site prediction for K5.1 leader sequence of VK is shown in Table 17 and FIG. 16.

10.4—Generation of the Chimeric 158 VH
Construct: pG1D200158VH

The 158 VH DNA fragment was amplified with primers: 158vh and 158vhrev (Table 9). The 450 bp (approx) PCR product was T-A ligated into the vector pCR2.1 and used to transform chemically competent TOP10 bacteria. Clones were selected by appropriate insert size and sequenced using the 1212 primer (Table 10). The correct expression insert was subcloned into pG1D200 expression vector and the correct subclone was selected by DNA sequencing using primer BDSH61R (Table 10). This clone was grown in 200 ml culture to produce plasmid DNA using the Qiagen Maxi Kit using the manufacturers protocol. The chimeric 158VH protein and DNA sequence is shown in Table 18.

10.5—Generation of the Chimeric 158 VK
Construct: pKN100158VK

The 158 VK DNA fragment was amplified with primers 158v1 and 158v1rev (Table 9). The 450 bp (approx) PCR product was T-A ligated into vector pCR2.1 and used to transform chemically competent TOP10 bacteria. Clones were selected by insert size and sequenced using the 1212 primer (Table 10). The correct clone was subcloned into pKN100 expression vector. The correct subclone was selected by screening for insert size and DNA sequencing using primer Hu-K2 (Table 10). This clone was grown in 200 ml culture to produce plasmid DNA using the Qiagen Maxi Kit using the manufacturers protocol.

Example 11

Production and Binding Properties of Chimeric 158 Antibody 11.1—COS 7 Cell Transformation and Cell Culture One vial of COS 7 cells was thawed and grown in DMEM supplemented with 10% Fetal clone 1 serum and antibiotics.

One week later, cells (0.8 ml at 10⁷/ml) were electroporated with pG1D200158VH plus pKN100158VK (10 µg DNA each). The cells were grown in 8 ml of growth medium in petri dishes for 3 days.

11.2—Chimeric Antibody Production

A sandwich ELISA was used to measure antibody concentrations in the COS 7 supernatants. Chimeric 158 VH×158 VK antibody was expressed at 0.3 µg/ml and subsequently at 3.7 µg/ml (Table 19) in transiently co-transfected COS cell conditioned media.

11.3—Chimeric Antibody Activity

Two ELISAs was used to analyse the antigen binding of chimeric 158. Using the 3.7 µg/ml chimeric antibody conditioned medium, binding to Aβ monomer was measured by a direct ELISA protocol (FIG. 12) and compared to the mouse 158 IgG. Secondly, a competition ELISA was done using either monomer or protofibril mixed in the fluid phase with antibody, which subsequently bound to Aβ monomer in the solid phase (FIG. 13). These showed that the chimeric 158 antibody binds to amyloid Aβ monomer and protofibril similarly to the original 158 mouse antibody.
Comment Later sequencing has shown that the mouse antibody sequence data, as shown in Tables 1 and 4 contain errors in both VH and VK chains at the 5' end. We suggest that this is due to the use of primers located within the V region. In later sequencing, primers located within the leader sequences, which cannot introduce mutations within the V regions, were used. The later sequencing showed sequence differences (see Tables 15 and 11). Said differences are however not located within the CDR regions.

The chimeric antibody binds amyloid Aβ monomer and protofibrils as shown by the direct binding ELISA and the competition ELISA respectively. This evidence confirms that the combination of 158 VH and 158 VK chains encodes the anti-LSAP antibody 158 and indicates that these sequences are suitable for the humanisation procedure to generate a humanised 158 antibody.

Example 12

Humanised Antibody Design and Discussion

Abbreviations and Definitions 158 mouse monoclonal anti-LSAP™ antibody 158
158 VH VH of mouse 158 antibody
158 VK VK of mouse 158 antibody
158RKAss Humanised version of 158 VK retaining cryptic splice sites
158RKA Humanised version of 158 VK with cryptic splice sites removed
158RHAss Humanised version of 158 VH retaining cryptic splice sites
158RHA Humanised version of 158 VH with cryptic splice sites removed
A Adenine
bp base pairs
C Cytosine
CDR Complementarity determining region in the immunoglobulin variable regions, defined using the Kabat numbering system
D-gene Diversity gene
DNA Deoxyribonucleic acid
FW Framework region: the immunoglobulin variable regions excluding the CDR regions
G Guanine
IgG immunoglobulin G
J-gene Joining gene
Kabat an immunoglobulin alignment and numbering system pioneered by Elvin A Kabat
mAb monoclonal antibody
MRCT Medical-Research Council Technology
T Thymine
VCI Framework residue classified as vernier or canonical or VH-VL interface
V-gene The gene segment that is rearranged together with a J (and D for VH) gene to generate a complete VH or VK
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region
Equipment

| Hardware & software | Origin |
|---|---|
| SGW02 computer | Silicon Graphics |
| PC computer | Hewlett Packard |
| SR 7.6 | Steve Searle, Wellcome Trust Sanger Institute, Cambridge. |
| Lasergene 6.0 | DNAstar Inc |
| Modeler 9.0 | Accelrys Ltd. |
| SignalP | Center for Biol. Sequence Analysis, Technical University of Denmark Website |
| BlastP | NCBI website |

12.1—Human V Gene Databases

The protein sequences of human and mouse immunoglobulins from the International Immunogenetics Database 2006 and the Kabat Database Release 5 of Sequences of Proteins of Immunological Interest (last update 17 Nov. 1999) were used to compile a database of immunoglobulin protein sequences in Kabat alignment. Our database contains 9322 human VH and 2689 human VK sequences. The sequence analysis program, SR 7.6, was used to query the human VH and VK databases with 158 VH and 158 VK protein sequences (Table 20).

12.2—Selection of a Human Framework for 158RHA

12.2.1—Comparison of 158 VH with Human VH Sequences

Human VH sequences with highest identity to 158 VH at Vernier (Foote, J. and G. Winter. 1992. Antibody framework residues affecting the conformation of the hypervariable loops. *J Mol. Biol.* 224:487-499.), Canonical (Morea, V., A. M. Lesk, and A. Tramontano. 2000. Antibody modeling: implications for engineering and design. *Methods* 20:267-279.) and VH-VL Interface (Chothia, C., J. Novotny, R. Bruccoleri, and M. Karplus. 1985. Domain association in immunoglobulin molecules. The packing of variable domains. *J Mol. Biol.* 186:651-663.) (VCI) residues, located within the V-region framework (FW), are shown in Table 21. The number of VCI residues (VCI score) and FW residues (FW score) identical to 158 are also shown. All these VH sequences share identical VCI residues, and CDR lengths, as shown in Table 22. AJ556669 has an unusual Pro74 not seen in the other human sequences in this dataset, leading us to discount it in the initial analysis. Pro74 is, however, present in the 158VH sequence, so AJ556669 could be considered as an alternative FW for humanisation, if the VH construct based on AF062243 does not bind antigen. The alignment of these sequences (Table 23) highlights their differences. AF062243 uniquely within this dataset has the conservative change T(82a)S and the conservation of F79. The other features of AF062243 are the conservative changes D1E, K19R, A23S, T77S, S118T. All other FW changes were common to all the frameworks in Table 23. AF062243 was selected as the framework on which to base 158RHA.

12.3—Generation of 158RHA

Figure 17:
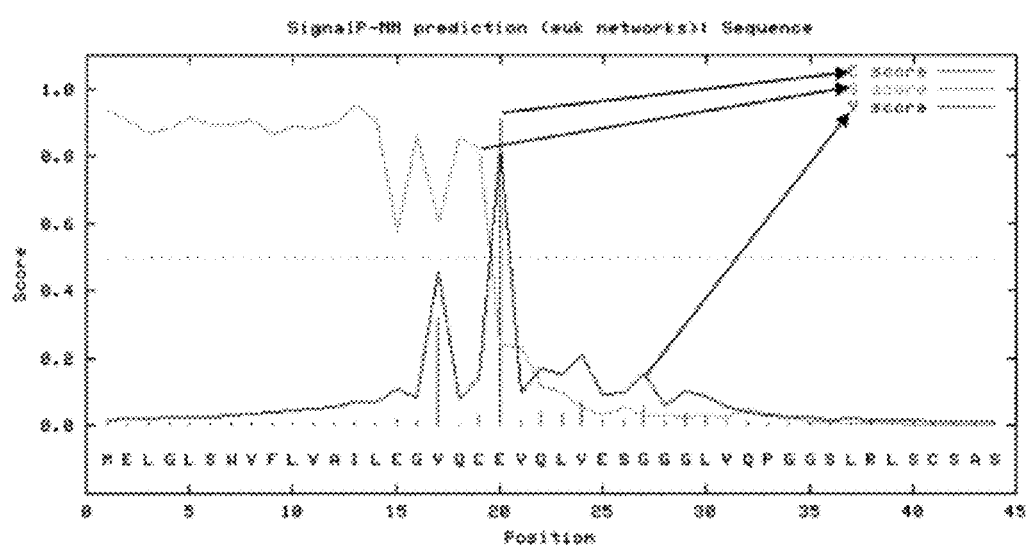
FIG. 17 shows the M99649 signal peptide (SEQ ID NO:153) cutting prediction. The SignalP algorithm 10 generates the combination score Y from the cleavage site score C and the signal peptide score S.

The design of 158RHA is simply the grafting of CDR 1, 2 and 3 from 158 VH into the acceptor FW of AF062243. The human germline V-gene most identical to AF062243 is VH M99649 (VH3-07), (Table 24) from which the leader peptide was extracted (Table 25). The SignalP algorithm (Nielsen, H., J. Engelbrecht, S. Brunak, and G. von Heijne. 1997. Identification of prokaryotic and eukaryotic signal peptides and prediction of their cleavage sites. *Protein Eng* 10:1-6.) predicted that it would cut appropriately with signal peptidase (Table 26; FIG. 17). Table 27 shows the scheme of grafting 158 VH CDR 1, 2 and 3 into the AF062243 FW, to generate 158RHA protein sequence. Table 28 shows the generation of the DNA sequence 158RHAss from the natural DNA sequences of 158 VH and AF062243. Analysis of the 158RHAss DNA sequence predicted the presence of splice donor sites, the prediction scores of which are shown in Table 29. Non-coding mutations were introduced to inactivate these predicted splice sites, as shown in Table 30 to generate the final 158RHA DNA sequence (Table 31).

12.4—Selection of a Human Framework for 158RKA 12.4.1—Comparison of 158 VK with Human VK Sequences The human VK sequences with highest identity to 158 VK at VCI residues are shown in Table 32 together with the number of VCI residues (VCI score) and FW residues (FW score) identical to 158 VK. Eleven sequences have all VCI residues identical to 158 VK. Table 33 shows that all these sequences have CDR lengths identical to 158 VK. Table 34 highlights their differences, showing that K45 is retained in AB064054 only, which also retains I85. The G100P change is unremarkable because P100 is common, having an incidence of 15% in our human VK database. The two substitutions: T7S and K74R, are conservative, and all other substitutions are common to all the sequences in Table 34. For these reasons AB064054 was selected to generate 158RKA.

12.5—Generation of 158RKA

Figure 18:
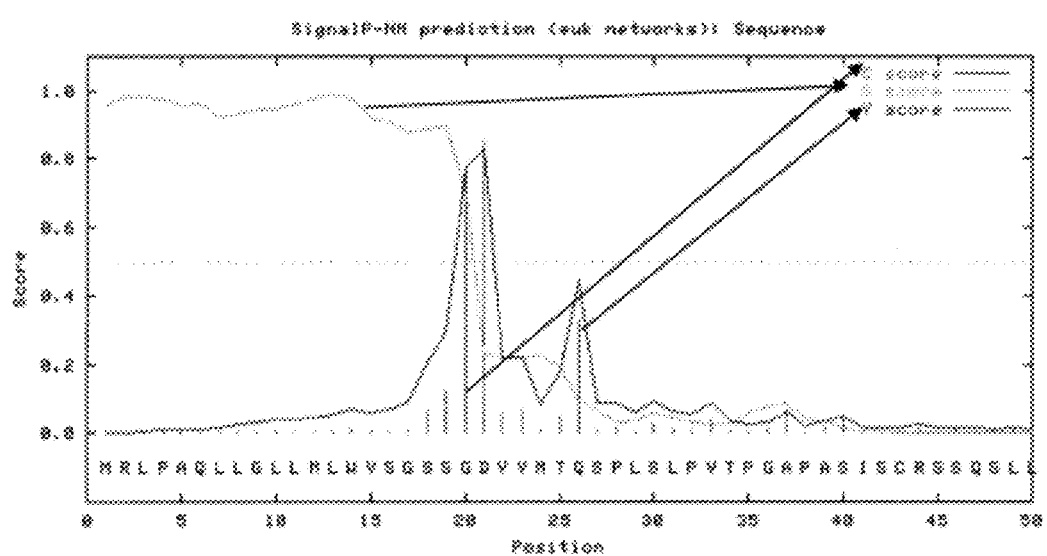
FIG. 18 shows the A19 signal peptide (SEQ ID NO:239) cutting prediction. The SignalP algorithm 10 generates the combination score Y from the cleavage site score C and the signal peptide score S.

The design of 158RKA is the simple grafting of the CDRs 1, 2 and 3 from 158 VK into the acceptor FW of human AB064054. The nearest germline V-gene to AB064054 is A19 (Table 35), from which the leader peptide was extracted (Table 36). The SignalP algorithm predicted appropriate cutting (Table 37; FIG. 18) of this leader peptide. Table 38 shows the generation of the protein sequence of 158RKA by intercalation of the 158 VK CDRs into the FW of AB064054. Table 39 shows the generation of the DNA sequence of 158RKAss from the natural DNA sequence of 158 VK and AB064054. Analysis of the 158RKAss predicted the presence of splice donor sites, the scores of which are shown in Table 40. Non-coding mutations (41) were introduced to inactivate these sites and generate the final 158RKA DNA construct (Table 42).

12.6 Humanized Antibody (BAN2401) Binding Activity

The 158RKA and 158RHA genes were inserted into an expression vector containing the IgG1 constant region. This construct was expressed in COS cells to generate the humanized 158 antibody. The humanized 158 antibody was tested for binding activity and specificity in a competitive ELISA. The humanised antibody exhibited identical binding properties as to mAb158 and the 158 chimeric antibody (see FIG. 14.)

12.7 Additional Mutations in the 158RHA and 158RKA Chains

By comparing mouse germline V genes VH AAK71612 to 158 VH a single somatic mutation A60G in the CDR2 was identified. Furthermore, the molecular model of antibody 158 which contains three VH FW residues within 5 Å of CDR residues which are unconserved in 158RHA. These substitutions are D1E, P74A and T82S (Table 43). Similarly, there are two VK FW residues within 5 Å of CDR residues which is unconserved in 158RKA. This substitution is L3V and G100P (Table 44). Introduction of back mutations at positions VH-1, VH-74, VH-82, VK-3 and VK-100 into 158RHA and 158RKA, in humanised versions 158RHB, 158RHC, 158RHD, 158RKB and 158RKC are shown in Table 43 and 44.

REFERENCES

Bacskai et al., Nat. Med. 7:369-372, 2001.
Bard et al., Nat. Med. 6:916-919, 2000.
Bayer et al., Neurology 64:94-101, 2005.
Brendza et al., J. Clin. Invest. 115:428-33, 2005.
Chen et al., Nature, 408:975-9, 2000.
Chothia, C. et al, J Mol. Biol., 186:651-663, 1985.
Ester W. P. Science 293, 1449-1459, 2001.
Gullberg et al., Proc. Natl. Acad Sci, 101:8420-4, 2004.
Foote, J. et al., J Mol. Biol., 224:487-499, 1992.
Hoshi et al. Proc. Natl. Acad. Sci, 100:6370-6375, 2003.
Jarret J. T., Biochemistry, 32, 4693-4697,1993.
Leatherbarrow R. J. et al., Mol. Immunol. 22, 407, 1985.
Lord et al., Neurobiol. Aging, 27:67-77, 2006.
McLean et al., Ann. Neurol. 46:860-866, 1999.
Morea, V. et al., *Methods* 20:267-279, 2000.
Mullan et al., Nat. Genet. 1:345-347, 1992.
Nielsen, H. et al. Protein Eng 10:1-6, 1997.
Nilsberth et al., Nat. Neurosci. 4:887-893, 2001.
Näslund et al., JAMA, 283:1571-1577, 2000.
Pfeifer et al., Science 298:1379, 2002.
Racke et al., J. Neurosci 25:629-36, 2005.
Schenk D. et al. Nature, 400, 173-177, 1999.
Stenh et al., Ann. Neurol. 58:147-50, 2005.
Walsh D. M. et al., 272, 22364-22372,1997
Walsh D. M. et al., Nature, 416, 535-9, 2002.
Wilcock et al., J. Neurosci., 23:3745-51, 2003.
Wright A. et al., J. of Immunology, 3393-3402, 1998.
Xu Y. et al. J. Biol. Chem. 269, 3469-3474,1994.

TABLE 1

Amino acid sequence of variable regions of the heavy chain (VH) and light chain (VL/V$_\kappa$) from six different monoclonal antibodies specific for human wild-type Aβ protofibrils.

| | | |
|---|---|---|
| VH-EA1: | X731 | EVKLVESGGGLVGPGGSRKLSCAASGFT<u>FSSFGMH</u>WVRQAPEKGLEWVA<u>YISSGSSTIYYADTVKG</u>RFTISRDNPKN<br>TLPLQWLSLRESRDTAMYYCA<u>RYGWYAM-----DY</u>WGQGTSVTVSS<br>SEQ ID NO: 13 |
| VH-EA2: | X736 | EVELVESGGGLVKPSGSLKLSCAASGFTPSSYAMSWVRQTPEKRLEWVATISSGGSYTYYPDSVRGRFTISRDKAKN<br>TLYQKSSLRSRDTAMYYCARNYGSRRYF-----DVWGAGTSVTVSS<br>SEQ ID NO: 14 |
| VH-EA3: | X745 | QVELQQSGPELVKPSASVKMSCKASGVTFTSYVMHWVKQPGQGLEWIGYINPYNDGTKYNEKPKGKATLTSDKSSSV<br>AYNCLSSLRSEDSAVYYCARRVSPLTSYAM---DYWGQGTSVTVSS<br>SEQ ID NO: 15 |
| VH-EA7: | X746 | QVQLKESGPSLNAPPQSLSITCTVSGFSLTSYGVHWNRQPPGKGLEWLGVIWAGGSTNYNSALMS-RLSISKDNSKSQ<br>VFLKNNSLQTDDTAMYYCARGRYDGKTRFA-----YWGQGTLVTVSS<br>SEQ ID NO: 16 |
| VH-EA8: | X748 | EVKLMESGGGLVQPGGSRKLSCAASGFTFSSFGMHWVRQAPEKGLEWVAYISSGSSTIYYADTVKGR<br>FTISRDNPKNTLFLWMTSLREEDTAMYYCARGDSF---------DYWGQGTTLTVSS<br>SEQ ID NO: 17 |
| VH-EA9: | X758 | EVQRVESGGGLVGPSGSRKLSCAASGFTFSSFGMHWVRQAPEKGLEWVAYISSGSSTIYYGDTVKGRFTISRDNPKNTL<br>ELQWTSLRSEDTAMYYCAREGGYYYGRSYYTMDYWGQGTSVTVSS<br>SEQ ID NO: 18 |
| Vκ-BA1: | X731 | DVVMTQTPLSLPVSLGDCASLSC<u>RSSQSIVHSNGMTYLE-</u>WYLQKPGQSPKLLIN<u>KVSNRFS</u>GVPDRFSGSGSGTDFTL<br>KISRVEAEDLGVYY<u>CPQGSHVPP</u>IGGGGTKLRIK<br>SEQ ID NO: 19 |
| Vκ-BA2: | X736 | DIVMTQAPKFLLVSAGDRVTITCKASGSVSNDVA------WYQQEPGDSPKLLIYYASNAYTGVPDRFTGSSY<br>GTDFTFTISTVQAEDLAVYFCQQDYSSPFTFGSGTKLEIK<br>SEQ ID NO: 20 |
| Vκ-BA3: | X745 | DIVMTQAFSSLAVSAGEKVTMSCKSSQSLLNSRTRENYLAWYQQKPGQSPKLLIYWASTRESGVFDRFTGSGS<br>GTDFTLTISSVQAEDLAVYYCKQSYNL--WTFGGGTKLEIK<br>SEQ ID NO: 21 |
| Vκ-BA7: | X746 | EWVLTQSPAEMSASPGEKVTMTCRASESVSSEYLH-----WYQQKSGASPKLWIYSTSNLASGYPARFSGSSS<br>GTSYGLTISSVEAEDAATYYCQQYSGYPLTFGAGTKLELK<br>SEQ ID NO: 22 |
| Vκ-BA8: | X748 | DIVMTQAFLSLFVSLGDQASISCRSSQSLVHSNGNTYLH-WYLQKPGQSLKLLIYKVSNRFSGVPDRFSGGGSG<br>TDFTLKISRVEAEDLGYYECSQSTHVPLTFGAGTKLELK<br>SEQ ID NO: 23 |
| Vκ-BA9: | X758 | DIVWTQAPLSLPVSLGDQASISCRSSQSIVHWNGQTYL-EWYLQEPGQSPKLLIVKVSNRFSG<br>VPDRFSGSGSGTDFTLKISRVEADLGIYYCFQGSHVPPTFGGGTKLEIK<br>SEQ ID NO: 24 |

*Position of the various CDR regions (1-3) are underlined in VL and VH. The boundaries of the CDR regions (1-3) are shown in Table 3 and Table 4. Antibody BA9, also named 158 in the patent application., is an example of a high affinity protofibril specific antibody according to the invention.

TABLE 2

Amino acid sequences of CDR1-2 regions from VH chain from a protofibril selective antibody and amino acid substitutions that are compatible with high affinity binding to human wild-type AB protofibrils.

VH chain CDR-1 region

| | | |
|---|---|---|
| AASGFTFSSFGMHWVR | (SEQ ID NO: 25) | Antibody 158 |
| ---------YA-S--- | (SEQ ID NO: 26) | Substitutions* |

VH chain CDR-2 region

| | | |
|---|---|---|
| WVAYISSGSSTIYYGDTVKGRFT | (SEQ ID NO: 27) | Antibody 158 |
| --------------A-------- | (SEQ ID NO: 28) | Substitutions* |
| ---T----G-YT--P-S------ | (SEQ ID NO: 29) | Substitutions* |

TABLE 2-continued

Amino acid sequences of CDR1-2 regions from VH chain from a protofibril selective antibody and amino acid substitutions that are compatible with high affinity binding to human wild-type AB protofibrils.

VH chain CDR-3 region

CAREG-GYYYGRSYY-TMDYWGQ (SEQ ID NO: 30)   Antibody 158

CARYGxxxxxNYxxxxAMDYWGQ (SEQ ID NO: 31)   Substitutions and deletions*

CARNYxxxxGSRRxxxYFDVWGA (SEQ ID NO: 32)   Substitutions and deletions*

*The amino acid substitutions (other amino acid than in antibody 158) are shown with one amino acid letter code. Deletions are shown with (x).

TABLE 3

Amino acid sequences of CDR 1-3 regions from VL chain from a protofibril selective antibody and amino acid substitutions that are compatible with high affinity binding to human wild-type AB protofibrils VL chain CDR-1 region ISCRSSQSIVHSNGNTYLEWYL   (SEQ ID NO: 33)   Antibody 158

ITCKASQSVxxSNDxxxVAWYQ   (SEQ ID NO: 34)   Substitutions and deletions*

VL chain CDR-2 region

LIYKVSNRFSGVP            (SEQ ID NO: 35)   Antibody 158

---YA---YT---            (SEQ ID NO: 36)   Substitutions*

VL chain CDR-3 region

YYCFQGSHVPPTFGG          (SEQ ID NO: 37)   Antibody 158

-F-Q-DYSS-F---S          (SEQ ID NO: 38)   Substitutions*

*The amino acid substitutions (other amino acid than in antibody 158) are shown with one amino acid letter code. Deletions are shown with (x).

TABLE 4

Amino acid sequence of mouse framework regions of the mouse and human variable light chain (VL) region from protofibril specific antibodies Mouse framework* VL regions Divmtqaplslpvslgdqasiscwylqkpgqspkllilygvpdrfsgsgsgtdftlkisrveaedlgiyyc  antibody 158
(SEQ ID NO: 39)
......................................................................  BA9_VL_fr123
(SEQ ID NO: 40)
.v....t...............................................................v...  BA1_VL_fr123
(SEQ ID NO: 41)
........kf.l..a..rvt.t...q...................t...y.....ft..t.q....av.f.  BA2_VL_fr123
(SEQ ID NO: 42)

Human framework VL regions

......t......tp.ep.............q................................v.v...  VKII-3-1-(1)-O11
(SEQ ID NO: 43)
......s......tp.ep.............q................................v.v...  VKII-4-1-(1)-A19
(SEQ ID NO: 44)
......t....s.tp.qp.............q................................v.v...  VKII-4-1-(1)-A18
(SEQ ID NO: 45)
......t....s.tp.qp..............p.q..............................v.v...  VKII-4-1-(1)-A2
(SEQ ID NO: 46)
.v....s......t..qp......fg.r.....rr..............................v.v...  VKII-4-1-(1)-A17
(SEQ ID NO: 47)

*Framework region is the region outside the CDR regions. The CDR regions has been deleted for clarity.

TABLE 5

Amino acid sequence of mouse and human framework regions of the mouse and human variable light heavy (VH) region from protofibril specific antibodies

Mouse framework* VH regions

| | |
|---|---|
| Evklmesgggglvqpggsrklscaaswvrqapekglewvarftisrdnpkntlflqmtslrsedtamyycar (SEQ ID NO: 48) | antibody 158 |
| ................................................................................ (SEQ ID NO: 49) | BA9_VH_fr123 |
| ....v........................................................................... (SEQ ID NO: 50) | BA1_VH_fr123 |
| ....v.......k....l............t...r..................a....y...s................ (SEQ ID NO: 51) | BA2_VH_fr123 |

Human framework VH regions

| | |
|---|---|
| ..q.v............lr.............g................a..s.y...n...a....v...... (SEQ ID NO: 52) | VH3-7_fr123 |
| ..q.v............lr.............g......s........s....y...n...a....v...... (SEQ ID NO: 53) | VH3-53_fr123 |
| ..q.v............lr.............g......s........s....y...n...a....v....k (SEQ ID NO: 54) | |
| ..q.v............lr.............g......s........a..s.y...n...d....v...... (SEQ ID NO: 55) | VH3-48_fr123 |
| ..q.v............lr.............g...v..s........a....y...n...a....v...... (SEQ ID NO: 56) | VH3-74_fr123 |

*Framework region is the region outside the CDR regions. The CDR regions has been deleted for clarity.

TABLE 6

PCR primers for cloning mouse VK

| Name | Sequence (5'→3') |
|---|---|
| MKV1 | ATGAAGTTGVVTGTTAGGCTGTTGGTGCTG (SEQ ID NO: 57) |
| MKV2 | ATGGAGWCAGACACACTCCTGYTATGGGTG (SEQ ID NO: 58) |
| MKV3 | ATGAGTGTGCTCACTCAGGTCCTGGSGTTG (SEQ ID NO: 59) |
| MKV4 | ATGAGGRCCCCTGCTCAGWTTYTTGGMWTCTTG (SEQ ID NO: 60) |
| MKV5 | ATGGATTTWAGGTGCAGATTWTCAGCTTC (SEQ ID NO: 61) |
| MKV6 | ATGAGGTKCKKTGKTSAGSTSCTGRGG (SEQ ID NO: 62) |
| MKV7 | ATGGGCWTCAAGATGGAGTCACAKWYYCWGG (SEQ ID NO: 63) |
| MKV8 | ATGTGGGGAYCTKTTTYCMMTTTTTTCAATTG (SEQ ID NO: 64) |
| MKV9 | ATGGTRTCCWCASCTCAGTTCCTTG (SEQ ID NO: 65) |
| MKV10 | ATGTATATATGTTTGTTGTCTATTTCT (SEQ ID NO: 66) |
| MKV11 | ATGGAAGCCCCAGCTCAGCTTCTCTTCC (SEQ ID NO: 67) |
| MKC | ACTGGATGGTGGGAAGATGG (SEQ ID NO: 68) |

TABLE 7

PCR primers for cloning mouse heavy VH

| Name | Sequence (5'→3') |
|---|---|
| MHV1 | ATGAAATGCAGCTGGGGCATSTTCTTC (SEQ ID NO: 69) |
| MHV2 | ATGGGATGGAGCTRTATCATSYTCTT (SEQ ID NO: 70) |
| MHV3 | ATGAAGWTGTGGTTAAACTGGGTTTTT (SEQ ID NO: 71) |
| MHV4 | ATGRACTTTGGGYTCAGCTTGRTTT (SEQ ID NO: 72) |
| MHV5 | ATGGACTCCAGGCTCAATTTAGTTTTCCTT (SEQ ID NO: 73) |
| MHV6 | ATGGCTGTCYTRGSGCTRCTCTTCTGC (SEQ ID NO: 74) |
| MHV7 | ATGGRATGGAGCKGGRTCTTTMTCTT (SEQ ID NO: 75) |
| MHV8 | ATGAGAGTGCTGATTCTTTTGTG (SEQ ID NO: 76) |
| MHV9 | ATGGMTTGGGTGTGGAMCTTGCTATTCCTG (SEQ ID NO: 77) |
| MHV10 | ATGGGCAGACTTACATTCTCATTCCTG (SEQ ID NO: 78) |
| MHV11 | ATGGATTTTGGGCTGATTTTTTTTATTG (SEQ ID NO: 79) |
| MHV12 | ATGATGGTGTTAAGTCTTCTGTACCTG (SEQ ID NO: 80) |
| MHCG1 | CAGTGGATAGACAGATGGGGG (SEQ ID NO: 81) |
| MHCG2a | CAGTGGATAGACCGATGGGGC (SEQ ID NO: 82) |

TABLE 7-continued

PCR primers for cloning mouse heavy VH

| Name | Sequence (5'→3') |
|---|---|
| MHCG2b | CAGTGGATAGACTGATGGGGG (SEQ ID NO: 83) |
| MHCG3 | CAAGGGATAGACAGATGGGGC (SEQ ID NO: 84) |

Legend: Wobble bases are defined in Abbreviations (Section 2).

TABLE 8

Sequences important for efficient expression of immunoglobulin in mammalian cells

| Name | Consensus DNA Sequence (5'→3') |
|---|---|
| Kozak translation initiation site | G C C G C C R C C$^{-1}$ A$^{+1}$ U G G (SEQ ID NO: 85) |
| Kappa light chain splice donor site | A C :: G T R A G T (SEQ ID NO: 86) |
| Heavy chain splice donor site | M A G :: G T R A G T (SEQ ID NO: 87) |
| Immunoglobulin splice acceptor site | Y Y Y Y Y Y Y Y Y Y Y N C A G :: G (SEQ ID NO: 88) |

Legend: Bases shown in bold are considered to be invariant within each consensus sequence. Splice sites are defined by the symbol "::". Wobble bases are defined in Abbreviations (see Examples 9-11).

TABLE 9

Oligonucleotide primers used to generate chimeric 158

| Oligonucleotide name | Sequence (5'→3') |
|---|---|
| 158vh (SEQ ID NO: 89) | <u>AAGCTT</u>GCCGCCACCATGGACTCCAGGCTC |
| 158vhrev (SEQ ID NO: 90) | <u>GGGCCC</u>TTGGTGGAGGCTGAGGAGACGGTGACTGAGG |
| 158vl (SEQ ID NO: 91) | <u>AAGCTT</u>GCCGCCACCATGAAGTTGCCTGTTAGG |
| 158vlrev (SEQ ID NO: 92) | <u>GGATCC</u>ACTCACGTTTGATTTCCAGCTTGG |

Legend: Restriction sites are underlined. Kozak sequences are in bold type.

TABLE 10

Oligonucleotide primers used for sequencing

| Oligonucleotide name | Sequence (5'→3') |
|---|---|
| 1212 (17mer) (SEQ ID NO: 93) | GTTTTCCCAGTCACGAC |
| 1233 (24mer) (SEQ ID NO: 94) | AGCGGATAACAATTTCACACAGGA |
| Hu-K2 (17mer) (SEQ ID NO: 95) | CTCATCAGATGGCGGGA |
| BDSH61R (SEQ ID NO: 96) | CGCTGCTGAGGGAGTAGAGTC |

TABLE 11

DNA sequence of 158 VK, primer MKV1 and the VK sequence derived using primers located within the V region

```
                                                                                          (SEQ ID NO: 97)
  1  ATGAAGTTGCCTGTTAGGCTGTTGGTGCTGATGTTCTGGATTCCTGCTTCCAGCAGTGATGTTTTGATGACCCAAACTCCACTCTCCCTG  158 VK (SEQ ID NO: 98)
  1  .........VV....................                                                          MKV1

(SEQ ID NO: 99)
  1  ---------------------------------------------------...A..G..........GG.............***  VK

91  CCTGTCAGTCTTGGAGATCAAGCCTCCATCTCTTGCAGATCTAGTCAGAGCATTGTACATAGTAATGGAAACACCTATTTAGAATGGTAC  158 VK

34  ......................................................................................***  VK

181  CTGCAGAAACCAGGCCAGTCTCCAAAGCTCCTGATCTACAAAGTTTCCAACCGATTTTCTGGGGTCCCAGACAGGTTCAGTGGCAGTGGA  158 VK

124  ......................................................................................***  VK

271  TCAGGGACAGATTTCACACTCAAGATCAGCAGAGTGGAGGCTGAGGATCTGGGAATTTATTACTGCTTTCAAGGTTCACATGTTCCTCCG  158 VK

214  ......................................................................................***  VK

361  ACGTTCGGTGGAGGCACCAAGCTGGAAATCAAACGGGCTG                                                    158 VK

304  ...................................                                                     *** VK
```

Legend: Residues identical to 158 VK are indicated by a dot. ***Sequencing using primers located within the V region.

TABLE 12

Chimeric VK leader sequence selection -
K5.1# leader selection for the chimeric VK

| | |
|---|---|
| 158 VK | MKLPVRLLVLMFWIPASSS (SEQ ID NO: 100) |
| K5.1#Protein | MKLPVRLLVLMFWIPASSS (SEQ ID NO: 101) |
| K5.1#DNA | ATGAAGTTGCCTGTTAGGCTGTTGGTGCTGAT GTTCTGGATTCCTGCTTCCAGCAGT (SEQ ID NO: 102) |

TABLE 13

SignalP result 6 for K5.1# leader (SEQ ID NO: 103)
>Sequence length = 40

| | # Measure | Position | Value | Cut off signal peptide? |
|---|---|---|---|---|
| max. | C | 20 | 0.970 | 0.32 | YES |
| max. | Y | 20 | 0.890 | 0.33 | YES |
| max. | S | 13 | 0.989 | 0.87 | YES |
| mean | S | 1-19 | 0.954 | 0.48 | YES |
|  | D | 1-19 | 0.922 | 0.43 | YES |

Highest probability for cleavage is between amino acid residue 19 and 20 (SSS-DV)

TABLE 14

Protein and DNA sequence of chimeric 158 VK construct

```
              HindIII
              |
(SEQ ID    AAGCTTGCCGCCACCATGAAGTTGCCTGTTAGGCTGTTGGTGCTGATGTTCTGGATTCCTGCTTCCAGCAGTGATGTTTTG
 NO: 104)
           |--kozak--|------------K5.1# leader------------------>|158 VK|          81

(SEQ ID      K  L  A  A  T  M  K  L  P  V  R  L  L  V  L  M  F  W  I  P  A  S  S  S  D  V  L
 NO: 105)
           ATGACCCAAACTCCACTCTCCCTGCCTGTCAGTCTTGGAGATCAAGCCTCCATCTCTTGCAGATCTAGTCAGAGCATTGTA    162
           |------------------------------ 158 VK ------------------------------|

M  T  Q  T  P  L  S  L  P  V  S  L  G  D  Q  A  S  I  S  C  R  S  S  Q  S  I  V
           CATAGTAATGGAAACACCTATTTAGAATGGTACCTGCAGAAACCAGGCCAGTCTCCAAAGCTCCTGATCTACAAAGTTTCC    243
           |------------------------------ 158 VK ------------------------------|

H  S  N  G  N  T  Y  L  E  W  Y  L  Q  K  P  G  Q  S  P  K  L  L  I  Y  K  V  S
           AACCGATTTTCTGGGGTCCCAGACAGGTTCAGTGGCAGTGGATCAGGGACAGATTTCACACTCAAGATCAGCAGAGTGGAG    324
           |------------------------------ 158 VK ------------------------------|

N  R  F  S  G  V  P  D  R  F  S  G  S  G  S  G  T  D  F  T  L  K  I  S  R  V  E
           GCTGAGGATCTGGGAATTTATTACTGCTTTCAAGGTTCACATGTTCCTCCGACGTTCGGTGGAGGCACCAAGCTGGAAATC    405
           |------------------------------ 158 VK ------------------------------|

A  E  D  L  G  I  Y  Y  C  F  D  G  S  H  V  P  P  T  F  G  G  G  T  K  L  E  I
                             BamHI
                             |
           AAACGTGAGTGGATCC                                                                    421
           |15>|-Human K intron->
             K  R  E  W  I
```

TABLE 15

DNA sequence of 158 VH, primer MHV5 and the sequence derived
using primers located within the V region

```
  1 ATGGACTCCAGGCTCAATTTAGTTTTCCTTGTCCTTATTTTAAAAGGTGTCCAGTGTGATGTGCAGCTGGTGGAGTCT  158 VH
    GGGGGAGGCTTA
    (SEQ ID NO: 106)

1 ------------------------------------------------------..G...A.....A....A...   *** VH
    ............
    (SEQ ID NO: 107)

1 ........................                                                        MHV5
    (SEQ ID NO: 108)

91 GTGCAGCCTGGAGGGTCCCGGAAACTCTCCTGTGCAGCCTCTGGATTCACTTTCAGTAGCTTTGGAATGCACTGGGTT  158 VH
    CGTCAGGCTCCA

34 ...................................................
    ............
```

TABLE 15-continued

DNA sequence of 158 VH, primer MHV5 and the sequence derived using primers located within the V region

```
181 GAGAAGGGGCTGGAGTGGGTCGCATACATTAGTAGTGGCAGTAGTACCATCTACTATGGAGACACAGTGAAGGGCCGAT 158 VH
    TCACCATCTCC
124 ............................................................................ *** VH
    ...........

271 AGAGACAATCCCAAGAACACCCTGTTCCTGCAAATGACCAGTCTAAGGTCTGAGGACACGGCCATGTATTACTGTGCAA 158 VH
    GAGAGGGGGA
214 ............................................................................ *** VH
    ...........

361 TATTACTACGGTAGGAGTTACTATACTATGGACTACTGGGGTCAAGGAACCTCAGTCACCGTCTCCTCAGCCAAAACAA 158 VH
    CAGCCCCA
304 ............................................................................ *** VH
    ........
```

Legend: Residues identical to 158 VH are indicated by a dot.
***Sequencing using primers located within the V region.

TABLE 16

Chimeric VH leader selection - NL-1 VH leader sequence

| 158 VH leader | MDSRLNLVFLVLILKGVQC (SEQ ID NO: 109) |
| NL-1 protein | MDSRLNLVFLVLILKGVQC (SEQ ID NO: 110) |
| NL-1 DNA | ATGGACTCCAGGCTCAATTTAGTTTTCCTT GTCCTTATTTTAAAAGGTGTCCAGTGT (SEQ ID NO: 111) |

TABLE 17

SignalP result 6 for NL-1 VH leader sequence (SEQ ID NO: 112)

| | # Measure | Position | Value | | Cut off signal peptide? |
|---|---|---|---|---|---|
| max. | C | 20 | 0.775 | 0.32 | YES |
| max. | Y | 20 | 0.795 | 0.33 | YES |
| max. | S | 13 | 0.953 | 0.87 | YES |
| mean | S | 1-19 | 0.866 | 0.48 | YES |
|  | D | 1-19 | 0.830 | 0.43 | YES |

Highest probability for cleavage is between amino acid residue 19 and 20 (VQC-DV) 19 and 20: VQC-DV

TABLE 18

Protein and DNA sequence of chimeric 158 VH

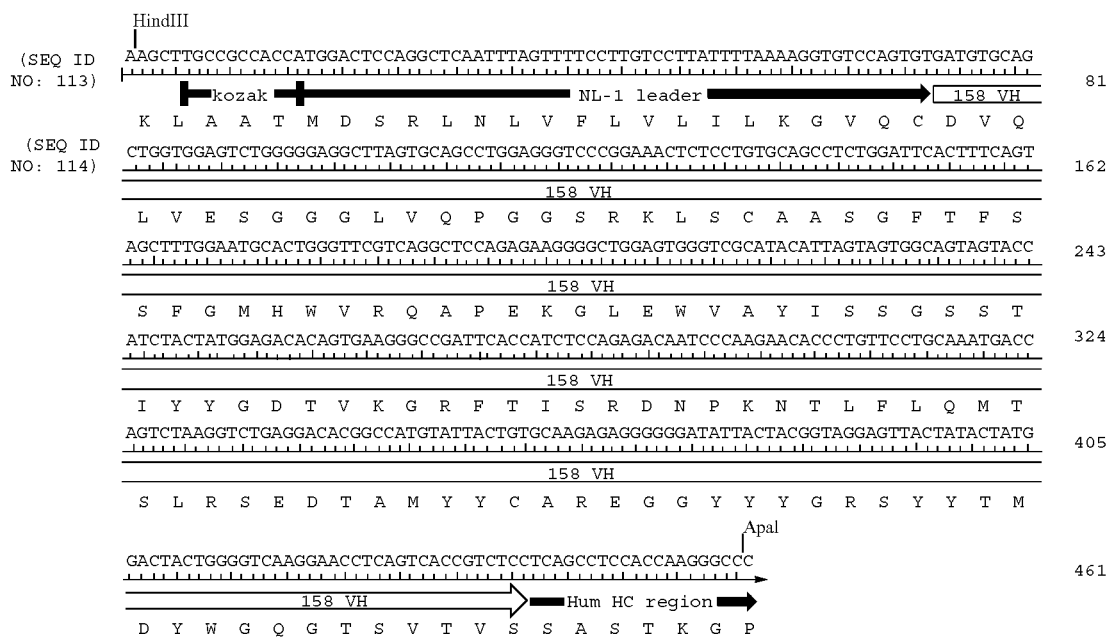

TABLE 19

Expression of chimeric 158 antibody in COS cells

| Number of Co-transfections | Expression Vector Constructs Co-Transfected | Antibody Concentration (ng/ml) |
|---|---|---|
| 2 pooled | pG1D200158 and pKN100158 | 300 |
| 2 pooled | pG1D200158 and pKN100158 | 3700 |

Legend: Antibody concentration was measured by ELISA in 3-day cultures of transfected COS 7 cells. COS cells were co-transformed with 10 µg each of the heavy and light chain chimeric expression vectors pG1D200158 and pKN100158.

TABLE 20

Amino acid sequence of 158 VH and 158 VK

| VH | DVQLVESGGGLVQPGGSRKLSCAASGFTESSFGM<br>HWVRQAPEKGLEWVAYISSGSSTIYYGDTVKGRF<br>TISRDNPKNTLFLQMTSLRSEDTAMYYCAREGGY<br>YYGRSYYTMDYWGQGTSVTVES<br>(SEQ ID NO: 115) |
|---|---|
| VK | DVLMTQTPLSLPVSLGDQASISCRSSQSIVHSNGN<br>TYLEWYLQKPGQSPKLLIYKVSNRFSGVPDRFSGS<br>GSGTDFTLKISRVEAEDLGIYYCFQGSHVPPTFGG<br>GTKLEIK<br>(SEQ ID NO: 116) |

TABLE 21

Best human VH framework VCI scores compared with 158 VH

| Kabat Number[6] | 2 | 24 | 26 | 27 | 28 | 29 | 30 | 37 | 39 | 45 | 47 | 48 | 49 | 67 | 69 | 71 | 73 | 78 | 91 | 93 | 94 | 103 |
|---|---|---|---|---|---|---|---|---|---|---|---|---|---|---|---|---|---|---|---|---|---|---|
| Canonical Residue[8] | - | 1 | 1 | - | 1 | - | - | - | - | - | - | - | - | - | - | 2 | - | - | - | - | 1 | - |
| Vernier Residue[7] | * | - | - | * | * | * | * | - | - | - | * | * | * | * | * | * | * | * | - | * | - | - |
| Interface Residue[9] | - | - | - | - | - | - | - | I | I | I | I | - | - | - | - | - | - | - | I | I | - | I |

| Sequence name | FW score | VCI score | VCI Residues |
|---|---|---|---|
| 158 VH | 87 | 22 | V A G F T F S V Q L W V A F I R N L Y A R W<br>(SEQ ID NO: 117) |
| 38687 | 79 | 22 | . . . . . . . . . . . . . . . . . . . . . .<br>(SEQ ID NO: 118) |
| AB021520 | 77 | 22 | . . . . . . . . . . . . . . . . . . . . . .<br>(SEQ ID NO: 118) |
| AJ556669 | 77 | 22 | . . . . . . . . . . . . . . . . . . . . . .<br>(SEQ ID NO: 118) |
| 38672 | 77 | 22 | . . . . . . . . . . . . . . . . . . . . . .<br>(SEQ ID NO: 118) |
| 38673 | 77 | 22 | . . . . . . . . . . . . . . . . . . . . . .<br>(SEQ ID NO: 118) |
| DQ322738 | 77 | 22 | . . . . . . . . . . . . . . . . . . . . . .<br>(SEQ ID NO: 118) |
| AB067108 | 76 | 22 | . . . . . . . . . . . . . . . . . . . . . .<br>(SEQ ID NO: 118) |
| AB021531 | 76 | 22 | . . . . . . . . . . . . . . . . . . . . . .<br>(SEQ ID NO: 118) |
| AB021532 | 76 | 22 | . . . . . . . . . . . . . . . . . . . . . .<br>(SEQ ID NO: 118) |
| AB063892 | 76 | 22 | . . . . . . . . . . . . . . . . . . . . . .<br>(SEQ ID NO: 118) |
| AB067237 | 76 | 22 | . . . . . . . . . . . . . . . . . . . . . .<br>(SEQ ID NO: 118) |
| AB021507 | 76 | 22 | . . . . . . . . . . . . . . . . . . . . . .<br>(SEQ ID NO: 118) |
| AF471177 | 76 | 22 | . . . . . . . . . . . . . . . . . . . . . .<br>(SEQ ID NO: 118) |
| AF471184 | 76 | 22 | . . . . . . . . . . . . . . . . . . . . . .<br>(SEQ ID NO: 118) |
| AF062243 | 76 | 22 | . . . . . . . . . . . . . . . . . . . . . .<br>(SEQ ID NO: 118) |
| AF174030 | 76 | 22 | . . . . . . . . . . . . . . . . . . . . . .<br>(SEQ ID NO: 118) |

TABLE 21-continued

Best human VH framework VCI scores compared with 158 VH

| Kabat Number[6] | 2 | 24 | 26 | 27 | 28 | 29 | 30 | 37 | 39 | 45 | 47 | 48 | 49 | 67 | 69 | 71 | 73 | 78 | 91 | 93 | 94 | 103 |
|---|---|---|---|---|---|---|---|---|---|---|---|---|---|---|---|---|---|---|---|---|---|---|
| Canonical Residue[8] | - | 1 | 1 | 1 | - | 1 | - | - | - | - | - | - | - | - | - | 2 | - | - | - | - | 1 | - |
| Vernier Residue[7] | * | - | - | * | * | * | * | - | - | - | * | * | * | * | * | * | * | * | - | * | * | - |
| Interface Residue[9] | - | - | - | - | - | - | - | I | I | I | I | - | - | - | - | - | - | - | I | I | - | I |

| Sequence name | FW score | VCI score | VCI Residues |
|---|---|---|---|
| AF466141 | 76 | 22 | . . . . . . . . . . . . . . . . . . . . . . (SEQ ID NO: 118) |
| AF466142 | 76 | 22 | . . . . . . . . . . . . . . . . . . . . . . (SEQ ID NO: 118) |
| AJ245279 | 76 | 22 | . . . . . . . . . . . . . . . . . . . . . . (SEQ ID NO: 118) |
| AJ579216 | 76 | 22 | . . . . . . . . . . . . . . . . . . . . . . (SEQ ID NO: 118) |

Legend: Canonical residues are numbered in this table according to which CDR they are associated with. FW score and VCI score are the number of residues in the FW or VCI definition respectively, which are identical to their counterpart in 158. Residues identical to those in 158 VH are indicated by a dot.

TABLE 22

Sequences of best VCI-scoring human VH, compared with 158 VH

```
Kabat                 1         2         3          4         5         6
Number6     -123456789012345678901234567890123456AB78901234567890123ABC34567890123456789
Canonical               1 111 1                    1                2    22
Vernier     *              ***                      ***                          * *
Interface                  I I I                    I I
Kabat CDR                  ******                   ******************

158 VH      -DVQLVESGGGLVQPGGSRKLSCAASGFTFSSFGMH--WVRQAPEKGLEWVAYISS--GSSTIYYGDTVKGRFTI
AB021520    -EVQLVESGGGLVQPGGSLKLSCAASGFTFSSYWMS--WVRQAPGKGLEWVANIKQ--DGSEKYYVDSVKGRFTI
AJ556669    -EVQLVESGGGLVQPGGSLRLSCAASGFTFSSYWMS--WVRQAPGKGLEWVANIKE--DGGEKFYVDSVKGRFTI
0Q322738    PLVQLVESGGGLVQPGGSLRLSCAASGFTFSSYWMS--WVRQAPGKGLEWVAVIWY--DGSNKYYADSVKGRFTI
AB067108    -EVQLVESGGGVVQPGGSLRLSCAASGFTFSNYAMH--WVRQAPGKGLEWVAVISY--DGSNKYYADSVKGRFTI
A5021531    -QVQLVESGGGVVQPGRSLKLSCAASGFTFSSYAMH--WVRQAPGKGLEWVAVISY--DGSNKYYADSVKGRFTI
AB021532    -QVQLVESGGGVVQPGRSLRLSCAASGFTFSSYAMH--WVRQAPGKGLEWVAVISY--DGSNKYYADSVKGRFTI
AB063892    -EVQLVESGGGLVQPGGSLRLSCAASGFTFSSYWMS--WVRQAPGKGLEWVANIKQ--DGSEKYYVDSVKGRFTI
AB067237    -EVQLVESGGGLVQPGGSLRLSCAASGFTFSSYWMS--WVRQAPGKGLEWVANIKQ--DGSEKYYVDSVKGRFTI
AB021507    -QVQLVESGGGVVQPGRSLKLSCAASGFTFSSYAMH--WVRQAPGKGLEWVAVISY--DGSNKYYADSVKGRFTI
AF471177    -EVQLVESGGGLVQPGGSLRLSCAASGFTFSSYWMS--WVRQAPGKGLEWVANIKQ--DGSEKYYVDSVKGRFTI
AF471184    -EVQLVESGGGLVQPGGSLRLSCAASGFTFSSYWMS--WVRQAPGKGLEWVANIKQ--DGSEKYYVDSVKGRFTI
AF062243    CEVQLVESGGGLVQPGGSLRLSCSASGFTFSTYWMT--WVRQAPGKGLEWVANIKP--HGSEAYYVDSVKGRFTI
AF174030    CEVQLVESGGGLVQPGGSLRLSCAASGFTFSSYWMS--WVRQAPGKGLEWVANIKQ--DGSEKYYVDSVKGRFTI
AF466141    -QVQLVESGGGVVQPGRSLRLSCAASGFTFSSYGMH--WVRQAPGKGLEWVAVIWY--DGSNKYYADSAKGRFTI
AF466142    -QVQLVESGGGVVQPGRSLRLSCAASGFTFSSYGMH--WVRQAPGKGLEWVAVIWY--DGSNKYYADSAKGRFTI
AJ245279    -QVQLVESGGGVVQPGGSLRLSCAASGFTFSSYGMH--WVRQAPGKGLEWVAVIWY--DGSNKYYADSVKGRFTI

Kabat         7         8         9        10              11
Number6     0123456789012ABC345678901234567890ABCDEFGHILKlmnopqrstuv1234567890123
Canonical   2                     1
Vernier     * *   *               **                            *
Interface              I I I      I                             I
Kabat CDR             ****************************

158 VH      SRDNPKNTLFLQMTSLASEDTAMYYCAREGGYYYGRSYYT---------------MDYWGQGTSVTVSS
            (SEQ ID NO: 119)
AB021520    SRDNAKNSLYLQMNSLRAEDTAVYYCARPDDSSGYYSAEY---------------FQHWGQGTLVTVSS
            (SEQ ID NO: 120)
AJ556669    SRDNPKNSLFLQMNSLRAEDTAVYYCARERGHDFWSIYYTH--------------FDYWGQGALVTVSS
            (SEQ ID NO: 121)
0Q322738    SRDNSKNTLYLQMNSLRAEDTAVYYCARDGGSI----------------------FDYWGQGTLVTVSS
            (SEQ ID NO: 122)
AB067108    SRDNSKNTLYLQMNSLRAEDTAVYYCARARDYYYP--------------------MDVWGQGTTVTVSS
            (SEQ ID NO: 123)
A5021531    SRDNSKNTLYLQMNSLRAEDTAVYYCARDQSWSRIAAAGTPPSL-----------FDPWGQGTLVTVSS
            (SEQ ID NO: 124)
```

TABLE 22-continued

Sequences of best VCI-scoring human VH, compared with 158 VH

| | |
|---|---|
| AB021532 | SRDNSKNTLYLQMNSLRAEDTAVYYCARARNYYDSSGYS----------------FDYWGQGTLVTVSS (SEQ ID NO: 125) |
| AB063892 | SRDNAKNSLYLQMNSLRAEDTAVYYCARVRRGS---------------------GDSWGQGTLVTVSS (SEQ ID NO: 126) |
| AB067237 | SRDNAKNSLYLQMNSLRAEDTAVYYCAREQQLGPHNW-----------------FDPWGQGTLVTVSS (SEQ ID NO: 127) |
| AB021507 | SRDNSKNTLYLQMNSLRAEDTAVYYCARDOETGTTFDYYYYG------------MDVWGQGTTVTVSS (SEQ ID NO: 128) |
| AF471177 | SRDNAKNSLYLQMNSLRAEDTAVYYCARDPMTTVVKPSLAT-------------NDYWGQGTLVTVSS (SEQ ID NO: 129) |
| AF471184 | SRDNAKNSLYLQMNSLRAEDTAVYYCARDCVGALGA------------------FDIWGQGTMVTVSS (SEQ ID NO: 130) |
| AF062243 | SRDNAKNSLFLQMSSLRAEDTAVYYCARANS-----------------------LDVWGQGTTVTVSS (SEQ ID NO: 131) |
| AF174030 | SRDNAKNSLYLQMNSLRAEDTAVYYCARDGDIGDWW------------------FDPWGQGTLVTVSS (SEQ ID NO: 132) |
| AF466141 | SRDNSKNTLFLQMNSLRAEDTAVYYCARDKGYYDYVWGSYRSNPKNDA-------FDIWGQGTMVTVSS (SEQ ID NO: 133) |
| AF466142 | SRDNSKNTLFLQMNSLRAEDTAVYYCARDKGYYDYVWGSYRSNPKNDA-------FDIWGQGTMVTVSS (SEQ ID NO: 134) |
| AJ245279 | SRDNSKNTLYLQMNSLRAEDTAVYYCARDRFF----------------------FDNWGQGTLVTVSS (SEQ ID NO: 135) |

TABLE 23

Alignment of 158 VH with the best VCI-scoring human VH

```
           1          2          3          4          5          6          7          8          9          10              11
  123456789012345678901234567890123456789012345678901234567890123456789012345678901234567890123456789012345678901234567---890ABCDEFv123456789012 3

DVQLVESGGGLVQPGGSRKLSCAASGFTFSSFGMHWVRQAPEKGLEWVAYISSGSSTIYYGDSTVKGRFTISRDNPKNTLFLQMTSLRSEDTAMYYCAREGG------YYYYGRSYYTMDYWGQGTSVTVSS     158 VH         (SEQ ID NO: 136)
E.........................YW.S......G........N.KQDG.EK..V.S...............A..S.Y...N...A.....V.....PDD------SSGYY.AEYFQH............L.       AB021520      (SEQ ID NO: 137)
L..........................YW.S......G........V.MYDG.NK..A.S...............S...Y...N...A.....V.......D-------S--IP.................L.       DQ322738      (SEQ ID NO: 138)
E.........V.............NYA.........G........V..YDG.NK..A.S...............S...Y...N...A.....V......AR------D..YP..................V.       AB067108      (SEQ ID NO: 139)
Q.........V....R.L.......YA.........G........V..YDG.NK..A.S...............S...Y...N...A.....V.....DQSMSR-I-AAAGTPPS.LP.P............L.       AB021531      (SEQ ID NO: 140)
Q.........V....R.L.......YA.........G........N.KQDG.EK..V.S...............A..S.Y...N...A.....V.....ARNYY-----DSSGYS----P..............L.       AB021532      (SEQ ID NO: 141)
E..................LR......YW.S......G........V..YDG.NK..A.S...............A..S.Y...N...A.....V.....VRR------GSG---------S..............L.       AB063892      (SEQ ID NO: 142)
E..................LR......YA.........G........N.KQDG.EK..V.S...............A..S.Y...N...A.....V.......Q-------QLGP.HWWF.P..............L.       AB067237      (SEQ ID NO: 143)
Q..................LR......YA.........G........N.KQDG.EK..V.S...............A..S.Y...N...A.....V.....DQETGTTP-D--YG----V...............T.       AB021507      (SEQ ID NO: 144)
E..................LR......YW.S......G........N.KQDG.EK..V.S...............A..S.Y...N...A.....V.....DPMT-----TVVKP.LA.N............L.       AF471177      (SEQ ID NO: 145)
E..................LR......YW.S......G........N.KQDG.EK..V.S...............A..S.Y...N...A.....V.....DPMT-----TVVKP.LA.N............L.       AF471184      (SEQ ID NO: 146)
E................LR...S....TYW.T......G........N.KPHG.EA..V.S...............A..S.....N...A.....V......AN--------SL.V................T.       AF062243      (SEQ ID NO: 147)
```

Legend: Residues identical to 158 VH are represented by a dot. CDRs are grey-shaded.

TABLE 24

VH signal peptide selection - 5.5.1 V-gene alignment of 158 VH,
human AF062243 and human germline M99649 (VH3-07)

```
DVQLVESGGGLVQPGGSRKLSCAASGFTFSSFGMHWVRQAPEKGLEWVAYIS    158 VH     (SEQ ID NO: 148)

E...............LR...S.......TYW.T......G.......N.K    AF062243   (SEQ ID NO: 149)

E...............LR............YW.S......G.......N.K    M99649     (SEQ ID NO: 150)

SGSSTIYYGDTVKGRFTISRDNPKNTLFLQMTSLRSEDTAMYYCAR          158 VH     (SEQ ID NO: 148)

PHG.EA..V.S..........A..S.....S...A....V.....           AF062243   (SEQ ID NO: 149)

QDG.EK..V.S..........A..S.Y...N...A....V.....           M99699     (SEQ ID NO: 150)
```

Legend: V-gene residues identical to 158 VH are represented by a dot.

TABLE 25

Signal peptide of M99649 human germline VH gene

```
DNA      ATGGAATTGGGGCTGAGCTGGGTTTTCCTTGTTGCTATTTTAGAAGGTGTCCAGTGT  (SEQ ID NO: 151)

protein  MELGLSWVFLVAILEGVQC                                          (SEQ ID NO: 152)
```

TABLE 26

M99649 signal peptide cutting prediction (SEQ ID NO: 153)

|      | # Measure | Position | Value | Cutoff | signal peptide? |
|------|-----------|----------|-------|--------|-----------------|
| max. | C         | 20       | 0.909 | 0.32   | YES             |
| max. | Y         | 20       | 0.836 | 0.33   | YES             |
| max. | S         | 13       | 0.953 | 0.87   | YES             |
| mean | S         | 1-19     | 0.859 | 0.48   | YES             |
|      | D         | 1-19     | 0.848 | 0.43   | YES             |

\# Highest probability for cleavage is between amino acid residue 19-20: VQC-DV.

TABLE 27

Generation of 158RHA protein sequence (SEQ ID NOS: 154-163)

```
Kabat           1         2         3         4          5          6
Number6         0123456789012345678901234567890123 45AB67890123456789012ABC34567890123456789

CDR                                   ===H1==              =====H2============
158 VH          -DVQLVESGGGLVQPGGSRKLSCAASGFTFSSFGMH--WVRQAPEKGLEWVAYISS--GSSTIYYGDTVKGRFTI

158 CDR         SFGMH--(SEQ ID NO: 155)    YISS--GSSTIYYGDTVKG (SEQ ID NO: 156)           EG

158RHA          -EVQLVESGGGLVQPGGSLRLSCSASGFTFSSFGMH--WVRQAPGKGLEWVAYISS--GSSTIYYGDTVKGRFTI

AF062243 FW     -EVQLVESGGGLVQPGGSLRLSCSASGFTFS        WVRQAPGKGLEWVA        RFTI (SEQ ID NO: 160)
                 (SEQ ID NO: 159)

AF062243        CEVQLVESGGGLVQPGGSLRLSCSASGFTFSTYWMT--WVRQAPGKGLEWVANIKP--HGSEAYYVDSVKGRFTI

Kabat           7          8         9         10               11
Number6         0123456789012ABC45678901234567890ABCDEFGHIJK1234567890123

CDR                                       =========H3========
158 VH          SRDNPKNTLFLQMTSLRSEDTAMYYCAREGGYYYGRSYYT----MDYWGQGTSVTVSS     (SEQ ID NO: 154)

158 CDR         GYYYGRSYYT----MDY (SEQ ID NO: 157)

158RHA          SRDNAKNSLFLQMSSLRAEDTAVYYCAREGGYYYGRSYYT----MDYWGQGTTVTVS      (SEQ ID NO: 158)

AF062243 FW     SRDNAKNSLFLQMSSLRAEDTAVYYCAR (SEQ ID NO: 161)    WGQGTTVTVS    (SEQ ID NO: 162)

AF062243        SRDNAKNSLFLQMSSLRAEDTAVYYCARANS-------------LDVWGQGTTVTVSS    (SEQ ID NO: 163)
```

TABLE 28

Generation of 158RHA DNA sequence-Generation of 158RHAss DNA sequence
(SEQ ID NOS: 155-157, 159-162, and 164-172)

| REGION | DNA | PROTEIN |
|---|---|---|
| VH3-07 leader | ATGGAATTGGGGCTGAGCTGGGTTTTCCTTGTTGCTA TTTTAGAAGGTGTCCAGTGT (SEQ ID NO: 164) | MELGLSWVFLVAILEGVQC (SEQ ID NO: 165) |
| AF062243 FW1 | GAGGTGCAGCTGGTGGAGTCTGGGGGAGGCTTGGTC CAGCCTGGGGGGTCCCTGAGACTCTCCTGTTCAGCCTC TGGATTCACCTTTAGT (SEQ ID NO: 166) | EVQLVESGGGLVQPGGSLRLS CSASGFTFS (SEQ ID NO: 159) |
| 158 CDR1 | AGCTTTGGAATGCAC (SEQ ID NO: 167) | SFGMH (SEQ ID NO: 155) |
| AF062243 FW2 | TGGGTCCGCCAGGCTCCAGGGAAGGGGCTGGAGTGGGTGGCC (SEQ ID NO: 168) | WVRQAPGKGLEWVA (SEQ ID NO: 160) |
| 158 CDR2 | TACATTAGTAGTGGCAGTAGTACCA TCTACTATGGAGACACAGTGAAGGGC (SEQ ID NO: 169) | YISSGSSTIYYGDTVKG (SEQ ID NO: 156) |
| AF062243 FW3 | CGATTCACCATCTCCAGAGAGACAACGCCAAGAACTCACTG TTTCTGCAAATGAGCAGCCTGAGAGC-CGAGGACACGGCCGTGTA TTATTGTGCGAGA (SEQ ID NO: 170) | RFTISRDNAKNSLFLQMSSLRA EDTAVYYCAR (SEQ ID NO: 161) |
| 158 CDR3 | GAGGGGGGATATTACTACGGTAGGAG TTACTATACTATGGACTAC (SEQ ID NO: 171) | EGGYYYGRSYYTMDY (SEQ ID NO: 157) |
| AF062243 FW4 | TGGGGCCAAGGGACCACGGTCACCGTCTCC (SEQ ID NO: 172) | WGQGTTVTVS (SEQ ID NO: 162) |

Legend: Human VH3-07 leader and AF062243VH FWs intercalated with 158 VH CDRs (grey-shaded) to generate 158RHAss. (relate to Tables 27 and 28)

TABLE 29

DNA and protein sequence of 158RHAss (SEQ ID NO: 173)
(SEQ ID NO: 174)

```
     ATGGAATTGGGGCTGAGCTGGGTTTTCCTTGTTGCTATTTTAGAAGGTGTCCAGTGTGAGGTGCAGCTGGTGGAGTCTGGG  81
                                          ├splice 4.3┤ ├splice 6.9┤
                                                ├splice 5.6┤
       M  E  L  G  L  S  W  V  F  L  V  A  I  L  E  G  V  Q  C  E  V  Q  L  V  E  S  G GGAGGCTTGGTCCAGCCTGGGGGGTCCCTGAGACTCTCCTGTTCAGCCTCTGGATTCACCTTTAGTAGCTTTGGAATGCAC 162
       G  G  L  V  Q  P  G  G  S  L  R  L  S  C  S  A  S  G  F  T  F  S  S  F  G  M  H TGGGTCCGCCAGGCTCCAGGGAAGGGGCTGGAGTGGGTGGCCTACATTAGTAGTGGCAGTAGTACCATCTACTATGGAGAC 243
                                              ├splice 5.9┤
       W  V  R  Q  A  P  G  K  G  L  E  W  V  A  Y  I  S  S  G  S  S  T  I  Y  Y  G  D ACAGTGAAGGGCCGATTCACCATCTCCAGAGACAACGCCAAGAACTCACTGTTTCTGCAAATGAGCAGCCTGAGAGCCGAG 324
       ├splice 5.0┤
       T  V  K  G  R  F  T  I  S  R  D  N  A  K  N  S  L  F  L  Q  M  S  S  L  R  A  E GACACGGCCGTGTATTATTGTGCGAGAGAGGGGGGATATTACTACGGTAGGAGTTACTATACTATGGACTACTGGGGCCAA 405
                                                        ├splice 4.7┤
       D  T  A  V  Y  Y  C  A  R  E  G  G  Y  Y  Y  G  R  S  Y  Y  T  M  D  Y  W  G  Q GGGACCACGGTCACCGTCTCC                                                              426
       G  T  T  V  T  V  S
```

Legend: Splice donor sites predicted by Lasergene 6.0 GeneQuest analysis, together with their score, using the human_ds_2 matrix with a threshold of 4.2.

TABLE 30

Mutations in 158RHA removing splice sites in 158RHAss

```
  1 ATGGAATTGGGGCTGAGCTGGGTTTTCCTTGTTGCTATTTTAGAGGGAGT 158RHA
    (SEQ ID NO: 175)
  1 .................................A..T.. 158RHAss
    (SEQ ID NO: 176)

51 CCAGTGCGAAGTGCAGCTGGTGGAGTCTGGGGGAGGCTTGGTCCAGCCTG 158RHA
 51 ......T..G....................................... 158RHAss

101 GGGGGTCCCTGAGACTCTCCTGTTCAGCCTCTGGATTCACCTTTAGTAGC 158RHA
101 .................................................. 158RHAss

151 TTTGGAATGCACTGGGTCCGCCAGGCTCCAGGGAAGGGGCTGGAATGGGT 158RHA
151 ........................................G..... 158RHAss

201 GGCCTACATTAGTAGTGGCAGTAGTACCATCTACTATGGAGACACCGTGA 158RHA
201 ............................................A.... 158RHAss

251 AGGGCCGATTCACCATCTCCAGAGACAACGCCAAGAACTCACTGTTTCTG 158RHA
251 .................................................. 158RHAss

301 CAAATGAGCAGCCTGAGAGCCGAGGACACGGCCGTGTATTATTGTGCGAG 158RHA
301 .................................................. 158RHAss

351 AGAGGGGGGATATTACTACGGAAGGAGTTACTATACTATGGACTACTGGG 158RHA
351 ....................T............................ 158RHAss

401 GCCAAGGGACCACGGTCACCGTCTCC                       158RHA
401 ..........................                       158RHAss
```

Legend 158RHA DNA sequence compared to 158RHAss (Table 5.7.2) which contains predicted splice sites. Positions identical to 158RHA are identified as a dot.

TABLE 31

DNA and protein sequence of 158RHA

```
(SEQ ID   ATGGAATTGGGGCTGAGCTGGGTTTTCCTTGTTGCTATTTTAGAGGGAGTCCAGTGCGAAGTGCAGCTGGTGGAGTCTGGG    81
NO: 177)  ◄──────────VH3-07 leader──────────►│  158RHA FW1

(SEQ ID   M  E  L  G  L  S  W  V  F  L  V  A  I  L  E  G  V  Q  C  E  V  Q  L  V  E  S  G
NO: 178)

GGAGGCTTGGTCCAGCCTGGGGGGTCCCTGAGACTCTCCTGTTCAGCCTCTGGATTCACCTTTAGTAGCTTTGGAATGCAC   162
          ◄──────────── 158RHA FW1 ────────────►│──── CDR1 ────

G  G  L  V  Q  P  G  G  S  L  R  L  S  C  S  A  S  G  F  T  F  S  S  F  G  M  H

TGGGTCCGCCAGGCTCCAGGGAAGGGGCTGGAATGGGTGGCCTACATTAGTAGTGGCAGTAGTACCATCTACTATGGAGAC   243
          │──── 158RHA FW2 ────►│───── CDR2 ─────

W  V  R  Q  A  P  G  K  G  L  E  W  V  A  Y  I  S  S  G  S  S  T  I  Y  Y  G  D

ACCGTGAAGGGCCGATTCACCATCTCCAGAGACAACGCCAAGAACTCACTGTTTCTGCAAATGAGCAGCCTGAGAGCCGAG   324
          ── CDR2 ─│──────────── 158RHA FW3 ────────────

T  V  K  G  R  F  T  I  S  R  D  N  A  K  N  S  L  F  L  Q  M  S  S  L  R  A  E

GACACGGCCGTGTATTATTGTGCGAGAGAGGGGGGATATTACTACGGAAGGAGTTACTATACTATGGACTACTGGGGCCAA   405
          ──── 158RHA FW3 ────►│──── CDR3 ────│ 158RHA F

D  T  A  V  Y  Y  C  A  R  E  G  G  Y  Y  Y  G  R  S  Y  Y  T  M  D  Y  W  G  Q

GGGACCACGGTCACCGTCTCC                                                             426
          ──── 158RHA FW4 ────►

G  T  T  V  T  V  S
```

TABLE 32

Best VCI scores of human VK compared with 158 VK

```
Kabat Number⁶      2 4 35 36 38 44 46 47 48 49 64 66 68 69 71 87 98
Canonical Residue⁸ 1           2  2     1
Vernier Residue⁷   ****        *********    *
Interface Residue⁹    IIII                     II
```

| Sequence | Fw score | VCI score | VCI residues |
|---|---|---|---|
| 158 VK | 80 | 17 | V M W Y Q P L L I Y G G G T F Y F (SEQ ID NO: 179) |
| AB064054 | 71 | 17 | V . . . . . . . . . . . . . . . . (SEQ ID NO: 180) |
| AB063934 | 70 | 17 | V . . . . . . . . . . . . . . . . (SEQ ID NO: 180) |
| AB064105 | 70 | 17 | V . . . . . . . . . . . . . . . . (SEQ ID NO: 180) |
| AY941999 | 70 | 17 | V . . . . . . . . . . . . . . . . (SEQ ID NO: 180) |
| AX805665 | 69 | 17 | V . . . . . . . . . . . . . . . . (SEQ ID NO: 180 |
| AB064104 | 69 | 17 | V . . . . . . . . . . . . . . . . (SEQ ID NO: 180) |
| AY942057 | 69 | 17 | V . . . . . . . . . . . . . . . . (SEQ ID NO: 180) |
| AB064055 | 68 | 17 | V . . . . . . . . . . . . . . . . (SEQ ID NO: 180) |
| AX742874 | 68 | 17 | V . . . . . . . . . . . . . . . . (SEQ ID NO: 180) |
| AY685343 | 67 | 17 | V . . . . . . . . . . . . . . . . (SEQ ID NO: 180) |
| AY685353 | 67 | 17 | V . . . . . . . . . . . . . . . . (SEQ ID NO: 180) |
| DQ187506 | 70 | 16 | I . . . . . . . . . . . . . . . . (SEQ ID NO: 181) |
| DQ187679 | 70 | 16 | I . . . . . . . . . . . . . . . . (SEQ ID NO: 181) |
| AY043107 | 69 | 16 | I . . . . . . . . . . . . . . . . (SEQ ID NO: 181) |
| AJ388639 | 69 | 16 | . . . . . . . . . V . . . . . . . (SEQ ID NO: 182) |
| AJ388646 | 69 | 16 | I . . . . . . . . . . . . . . . . (SEQ ID NO: 181) |
| AJ388642 | 69 | 16 | I . . . . . . . . . . . . . . . . (SEQ ID NO: 181) |
| M74470 | 69 | 16 | I . . . . . . . . . . . . . . . . (SEQ ID NO: 181) |
| X72466 | 69 | 16 | I . . . . . . . . . . . . . . . . (SEQ ID NO: 181) |
| U95244 | 69 | 16 | I . . . . . . . . . . . . . . . . (SEQ ID NO: 181) |
| AAA51016 | 69 | 16 | I . . . . . . . . . . . . . . . . (SEQ ID NO: 181) |
| X89054 | 69 | 16 | I . . . . . . . . . . . . . . . . (SEQ ID NO: 181) |
| DQ187505 | 69 | 16 | I . . . . . . . . . . . . . . . . (SEQ ID NO: 181) |

TABLE 32-continued

Best VCI scores of human VK compared with 158 VK

| Kabat Number[6] | 2 4 35 36 38 44 46 47 48 49 64 66 68 69 71 87 98 |
| --- | --- |
| Canonical Residue[8] | 1         2  2       1 |
| Vernier Residue[7] | ****    *********     * |
| Interface Residue[9] | IIII              II |

| Sequence | Fw score | VCI score | VCI residues |
| --- | --- | --- | --- |
| DQ187683 | 69 | 16 | I . . . . . . . . . . . . . . . .<br>(SEQ ID NO: 181) |
| DQ187691 | 69 | 16 | I . . . . . . . . . . . . . . . .<br>(SEQ ID NO: 181) |
| AX805669 | 68 | 16 | I . . . . . . . . . . . . . . . .<br>(SEQ ID NO: 181) |
| AF455562 | 68 | 16 | I . . . . . . . . . . . . . . . .<br>(SEQ ID NO: 181) |

Legend: Canonical residues are numbered in this table according to which CDR they are associated. FW score and VCI score are the number of residues in the FW or VCI defination respectively, which are identical to their counterpart in 158. Residues identical to 158 VK are indicated by a dot.

TABLE 33

Sequences of best VCI-scoring human VK, compared with 158 VK

```
                            1         2          3          4          5
Kabat number6  12345678901234567890123456 7ABCDEF8901234567890123456789012345678

Canonical8     1                   1   1    1   1                   2
Vernier7       * *                              **            ****
Interface9                                   F  F  F     F F
VCI            1 *                   1   1    1 1F*F  F     F ****
Kabat CDR                         ****************

158 VK         DVLMTQTPLSLPVSLGDQASISCRSSQSIVHS-NGNTYLEWYLQKPGQSPKLLIYKVSNRFSGV
AB064054       DVVMTQSPLSLPVTPGAPASISCRSSQSLLHT-NGVNFLDWYLQKPGQSPKLLIYLASHRASGV
AB063934       DVVMTQSPLSLPVTPGEPASISCRSSQSLLHS-NGYNYLDWYLQKPGQSPQLLIYLGSNRASGV
AB064105 scFv  DVVMTQSPLSLPVTPGEPASISCRSSQSLLHS-NGYNYLDWYLQKPGQSPQLLIYLGSNRASGV
AY941999 scFv  DVVMTQSPLSLPVTPGEPASISCRSSQSLLHS-NGYNYLDWYLQKPGQSPQLLIYLGSNRASGV
AX805665 patent DVVMTQSPLSLPVTPGEPASISCRSSQSIVHS-NGNTYLQWYLQKPGQSPQLLIYKVSNRLYGV
AB064104       DVVMTQSPLSLPVTPGEPASISCRSSQSLLHS-NGYNYLDWYLQKPGQSPQLLIYLGSNRASGV
AY942057 scFv  DVVMTQSPLSLPVTPGEPASISCRSSQSLLHS-NGYNYLDWYLQKPGQSPQLLIYLGSNRASGV
AB064055       DVVMTQSPLSLPVTPGEPASISCRSSQSLLHS-NGYNYSDWYLQKPGQSPQLLIYLGSSRASGV
AX742874       DVVMTQTPLSLSVTPGQPASISCRSSQSLLHS-DGMTYFSWYLQKPGQPPQLLIYEVSNRFSGV
AY685343       DVVMTQSPLSLAVTPGEPASISCRSSQSVVFT-NGKNYLDWYLQKPGQSPQLLIYLGSNRASGV
AY685353       DVVMTQSPLSLAVTPGEPASISCRSSQSVVFT-NGKNYLDWYLQKPGQSPQLLIYLGSNRASGV
DQ187506       DIVMTQTPLSLPVTPGEPASISCRSSQSLLES-HGYNYLDWYLQKPGQSPQLLIYLASNRPSGV
DQ187679       DIVMTQTPLSLPVTPGEPASISCRSSQSLLHS-NGYNYLDWYLQKPGQSPQLLIYLGSNRASGV
AY043107       DIVMTOSPLSLPVTPGEPASISCRSSQSLLHS-NGYNYLDWYLQKPGQSPQLLIYLGSNRASGV
AJ388639       DVVMTQSPLSLPVTPGEPASISCRSSQSLLHS-NGYNYFAWYLQKPGQSPQLLVYLGSNRASGV
AJ388646       DIVMTQSPLSLPVTPGEPASISCRSSQSLLHS-NGYNYLDWYLQKPGQSPQLLIYLGSNRASGV
AJ388642       DIVMTQSPLSLPVTPGEPASISCRSSQSLLHS-NGYNYLDWYLQKPGQSPQLLIYLGSNRASGV
M74470         DIVMTQSPLSLPVTPGEPASISCRSSQSLLHS-NGFNYLHWYLQKPGQSPRLLIYLGSNRASGV
X72466         DIVMTQSPLSLPVTPGEPASISCRSSQSLLHN-NGYNYLDWYLQKPGQSPQLLIYLGSNRASGV
U95244         DIVMTOSPLSLPVTPGEPASISCRSSQSLLYS-NGYNYLDWYLQKPGQSPQLLIYLGSNRASGV
AAA51016       DivmTQSFLELPVTPGEPASISCRESQSLLKS-NGFNYLKWYLQKPGQSPRLLIYLGSNRASGV
X89054         DIVMTQSPLSLPVTPGEPASISCRSSQSLLHS-NGYNYFDWYLQKPGQSPQLLIYLGSNRASGV
DQ187505       DIVMTOSPLSLPVTPGEPASISCRSSQSLLES-HGYNYLDWYLQKPGQSPQLLIYLASNRPSGV
DQ187683       DIVMTQTPLSLPVTPGEPASISCRSSQSLLHG-NGYNYLDWYLQKPGQSPQLLIYLGSNRASGV
DQ187691       DIVMTQTPLSLPVTPGEPASISCRSSQSLLHG-NGYNYLDWYLQKPGQSPQLLIYLGSNRASGV
AX805669       DIVMTQSPLSLPVTPGEPASISCRSSQSIVHS-NGNTYLQWYLQKPGQSPQLLIYKVSNRLYGV 6          7          8          9         10
Kabat number6              901234567890123456789012345678901234 5ABCDEF678901234567

Canonical8                          2   1                 3    3       3
Vernier7                        *  *  **  *                            *
Interface9                                            F F F       F F
VCI                             *  *  **  *           F F3F  33   *    F3F
Kabat CDR                                              ***************

158 VK                     PDRFSGSGSGTDFTLKISRVEAEDLGIYYCFQGSHVP------PTFGGGTKLEIK
                           (SEQ ID NO: 183)
AB064054                   PDRFSGSGSGTDFTLRISRVEAEDVGIYYCMQGLQTP------FTFGPGTKLEIK
                           (SEQ ID NO: 184)
```

TABLE 33-continued

Sequences of best VCI-scoring human VK, compared with 158 VK

| | |
|---|---|
| AB063934 | PDRFSGSGSGTDFTLKISRVEAEDVGVYYCMQALQTP------LTFGGGTKVEIK (SEQ ID NO: 185) |
| AB064105 scFv | PDRFSGSGSGTDFTLKISRVEAEDVGVYYCMQALQTP------YTFGQGTKLEIK (SEQ ID NO: 186) |
| AY941999 scFv | PDRFSGSGSGTDFTLKISRVEAEDVGVYYCMQALQTP------YTFGQGTKLEIK (SEQ ID NO: 187) |
| AX805665 patent | PDRFSGSGSGTDFTLKISRVEAEDVGVYYCFQGSHVP------WTFGQGTKVEIK (SEQ ID NO: 188) |
| AB064104 | PDGFSGSGSGTDFTLKISRVEAEDVGVYYCMQALQTP------HTFGQGTKLEIK (SEQ ID NO: 189) |
| AY942057 scFv | PDRFSGSGSGTDFTLKISRVEAEDVGVYYCMQALQSP------PTFGRGTKVEIK (SEQ ID NO: 190) |
| AB064055 | PDRFSGSGSGTDFTLKISRVEAEDVGVYYCMQALQTP------FTFGPGTKVDIK (SEQ ID NO: 191) |
| AX742874 | PDRFSGSGSGTDFTLKISRVEAEDVGVYYCMQNIQLP------WTFGQGTKVEIK (SEQ ID NO: 192) |
| AY685343 | PDRFSGSGSGTDFTLKISRVEADDVGVYYCMHAVQAP------WTFGQGTKVEIK (SEQ ID NO: 193) |
| AY685353 | PDRFSGSGSGTDFTLKISRVEADDVGVYYCMHAVQAP------WTFGQGTKVEIK (SEQ ID NO: 194) |
| DQ187506 | PDRFSGSGSGTDFTLKISRVEAEDVGIYYCMQNLQTP------YSFGQGTKLEIR (SEQ ID NO: 195) |
| DQ187679 | PDRFSGSGSGTDFTLKISRVEAEDVGVYYCMQALQTP------HSFGQGTKLEIK (SEQ ID NO: 196) |
| AY043107 | PDRFSGSGSGTDFTLKISRVEAEDVGVYYCMQALQTP------LTFGGGTKVEIK (SEQ ID NO: 197) |
| AJ388639 | PDRFSGSGSGTDFTLKISRVEAEDVGIYYCMQVLQTP------YTFGQGTKLEIS (SEQ ID NO: 198) |
| AJ388646 | PDRFSGSGSGTDFTLKISRVEAEDVGVYYCMQALQTP------LTFGGGTKVEIK (SEQ ID NO: 199) |
| AJ388642 | PDRFSGSGSGTDFTLKISRVEAEDVGVYYCMQALQTP------PTFGGGTKVEIK (SEQ ID NO: 200) |
| M74470 | PDRFSGSGSGTDFTLKISRVEADDVGIYYCMQALQSP------YTFGQGTKLEIK (SEQ ID NO: 201) |
| X72466 | PDRFSGSGSGTDFTLKISRVEAEDVGVYYCMQVLQIP------LTFGGGTKVEIK (SEQ ID NO: 202) |
| U95244 | PDRFSGSGSGTDFTLKISRVEAEDVGDYYCMQALQSP------LTFGGGTKVEIK (SEQ ID NO: 203) |
| AAA51016 | PDRFSGSGSGTUFTLKISRVEADDvGiyycmQALQSP------YTFGQGTKLEIK (SEQ ID NO: 204) |
| X89054 | PDRFSGSGSGTDFTLKISRVEAEDVGVYYCMQALQTP------LTFGGGTKVEIK (SEQ ID NO: 205) |
| DQ187505 | PDRFSGSGSGTDFTLKISRVEAEDVGIYYCMQNLQTP------YSFGQGTKLEIR (SEQ ID NO: 206) |
| DQ187683 | PDRFSGSGSGTDFTLKISRVEAEDVGVYYCMQALQTP------RTFGQGTKVEIK (SEQ ID NO: 207) |
| DQ187691 | PDRFSGSGSGTDFTLKISRVEAEDVGVYYCMQALQTP------RTFGQGTKVEIK (SEQ ID NO: 208) |
| AX805669 | PDRFSGSGSGTDFTLKISRVEAEDVGVYYCFQGSHVP------WTFGQGTKVEIK (SEQ ID NO: 209) |

TABLE 34

Alignment of 158 VK with the best VCI-scoring human VK

```
               1                    2                      3                 4                  5                 6                 7                 8                9           10
     123456789012345678901234567ABCDE89012345678901234567890123456789012345678901234567890123456789012345678901234567890123456789012345678901234567  Kabat number
     DVLMTQTPLSLPVSLGDQASISCRSSQSIYHSNGNTYLEWYLQKPGQSPKLLIYKVSNRFSGVPDRFSGSGSGTDFTLKISRVEAEDLGIYYCFQGSHVPPTFGGGTKLEIK  158K
.V...S........TP.AP...........LL.T.VNF.D........................................R................M.LQT.F.........P......  AB064054 (SEQ ID NO: 210)
.V...S........TP.EP...........LL...EN.D................Q..........................................V...M.ALQT.L........V...  AB063934 (SEQ ID NO: 211)
.V...S........TP.EP...........LL...KN.D................Q..........................................V.V.M.ALQT.Y........Q...  AB064105 (SEQ ID NO: 212)
.V...S........TP.EP...........LL...KN.D................Q..........................................V.V.M.ALQT.Y........Q...  AY941999 (SEQ ID NO: 213)
.V...S........TP.EP...........LL......Q........................G..................................V...M.....W............  AY805665 (SEQ ID NO: 214)
.V...S........TP.EP...........LL...KN.D................Q..........................................V.V.M.ALQT.H........Q...  AB064104 (SEQ ID NO: 215)
.V...S........TP.EP...........LL...KN.D................Q..........................................V.V.M.ALQS..........R...  AY942057 (SEQ ID NO: 216)
.V...S........TP.EP...........LL...KN.SD...............Q..........................................V.V.M.ALQT.P........P..VD  AB064055 (SEQ ID NO: 217)
.V...S........TP.QP...........LL.D.M..PS........P.Q................................................V.V.M.NTQL.W........Q...  AX742874 (SEQ ID NO: 218)
.V...S........TP.EP...........LL...KN.D................Q..........................................D.V.V.MFAVQA.W........Q...  AY685343 (SEQ ID NO: 219)
.V...S........TP.EP...........V.FT.KN.D................Q..........................................D.V.V.MFAVQA.W........Q...  AY685353 (SEQ ID NO: 220)
.V...S........TP.EP...........V.FT.KN.D................Q..........................................V...M.NLQT.YS.......Q...  DQ187506 (SEQ ID NO: 221)
.V...S......A.TP.EP...........LLE.H.KN.D................Q..........................................V.V.M.ALQT.HS.......Q...  DQ187679 (SEQ ID NO: 222)
.V...S......A.TP.EP...........LL...KN.D................Q..........................................V.V.M.ALQT.L........Q...  AY043107 (SEQ ID NO: 223)
.IV..S........TP.EP...........LL...KN.PA...............Q.V.........................................V...M.VLQT.Y........Q..S  AJ388639 (SEQ ID NO: 224)
.IV..S........TP.EP...........LL...KN.D................Q..........................................V...M.ALQT.L........V...  AJ388646 (SEQ ID NO: 225)
.IV..S........TP.EP...........LL...KN.D................Q..........................................V...M.ALQT...........V...  AJ388642 (SEQ ID NO: 226)
.IV..S........TP.EP...........LL...FN.H................R..........................................D.V.M.ALQS.Y........Q...  AAA51016 (SEQ ID NO: 227)
.IV..S........TP.EP...........LL...KN.FD...............Q..........................................V.V.M.ALQT.L........V...  X89054  (SEQ ID NO: 228)
.IV..S........TP.EP...........LLE.H.KN.D................Q..........................................V...M.NLQT.YS.......Q..R  DQ187505 (SEQ ID NO: 229)
.IV..S........TP.EP...........LL.G.KN.D................Q..........................................V.V.M.ALQT.R........Q...  DQ187683 (SEQ ID NO: 230)
.IV..S........TP.EP...........LL.G.KN.D................Q..........................................V.V.M.ALQT.R........Q...  DQ187691 (SEQ ID NO: 231)
.IV..S........TP.EP...........LL......Q........................................................................LV.M....W..........V...  AX805669 (SEQ ID NO: 232)
```

Legend: CDR 1, 2 and 3 are grey-shaded.

TABLE 35

VK signal peptide selection-Alignment of 158 VK with human AB064054 and human germline A19

```
DVLMTQTPSLSPVSLGDQASISCRSSQSIVHSNGNTYLEWYLQKPGQSPKLLIYKVSN   158 VK
(SEQ ID NO: 234)
..V...S......TP.AP..........LL.T..VNF.D..............LA.H   AB064054
(SEQ ID NO: 235)
.IV...S......TP.EP..........LL....YN..D.........Q....LG..   A19
(SEQ ID NO: 236)

RFSGVPDRFSGSGSGTDFTLKISRVEAEDLGIYYCFQGSHVPPTFGGGTKLEIK      158 VK
(SEQ ID NO: 234)
.A...................R........V.....M..LQT.F...P......N   AB064054
(SEQ ID NO: 235)
.A..........................V.V...M.ALQT.                  A19
(SEQ ID NO: 236)
```

TABLE 36

Signal peptide of human A19 (VK2-28; X63397) germline VK

| | VK A19 leader sequence |
|---|---|
| DNA | ATGAGGCTCCCTGCTCAGCTCCTGGGGCTG CTAATGCTCTGGGTCTCTGGATCCAGTGGG (SEQ ID NO: 237) |
| protein | MRLPAQLLGLLMLWVSGSSG (SEQ ID NO: 238) |

TABLE 37

A19 signal peptide cutting prediction (SEQ ID NO: 239)
>Sequence length = 50

| | # Measure | Position | Value | Cutoff | signal peptide? |
|---|---|---|---|---|---|
| max. | C | 21 | 0.853 | 0.32 | YES |
| max. | Y | 21 | 0.831 | 0.33 | YES |
| max. | S | 13 | 0.990 | 0.87 | YES |
| mean | S | 1-20 | 0.932 | 0.48 | YES |
|  | D | 1-20 | 0.881 | 0.43 | YES |

Most likely cleavage site between pos. 20 and 21: SSG-DV

TABLE 38

Generation of 158RKA Protein Sequence (SEQ ID NOS: 240-249)

```
Kabat                   1         2          3         4         5
number 6        1234567890123456 7ABCDEF890123456789012345678901234567 89
CDR                             =======L1=======              ==L2===
158 VK          DVLMTQTPLSLPVSLGDQASISCRSSQSIVHS-NGNTYLEWYLQKPGQSPKLLIYKVSNRFSGVP
CDR             (SEQ ID NO: 241)RSSQSIVHS-NGNTYLE(SEQ ID NO: 242)KVSNRFS
158RKA          DVVMTQSPLSLPVTPGAPASISCRSSQSIVHS-NGNTYLEWYLQKPGQSPKLLIYKVSNRFSGVP
FW      (SEQ ID NO: 245) DVVMTQSPLSLPVTPGAPASISC(SEQ ID NO: 246)  WYLQKPGQSPKLLIY      GVPD
AB064054        DVVMTQSPLSLPVTPGAPASISCRSSQSLLHT-NGVNFLDWYLQKPGQSPKLLIYLASHRASGVP Kabat   6          7          8          9         10
        number 6 0123456789012345678901234567890123458ABCDEF678901234567
        CDR                                ======L3=======
        158 VK  DRFSGSGSGTDFTLKISRVEAEDLGIYYCFQGSHVP------PTFGGGTKLEIK (SEQ ID NO: 240)
        CDR                              FQGSHVP------PT (SEQ ID NO: 243)
        158RKA  DRFSGSGSGTDFTLRISRVEAEDVGIYYCFQGSHVP------PTFGPGTKLEIK (SEQ ID NO: 244)
        FW      RFSGSGSGTDFTLRISRVEAEDVGIYYC (SEQ ID NO: 247)FGPGTKLEIK (SEQ ID NO: 248)
        AB064054 DRFSGSGSGTDFTLRISRVEAEDVGIYYCMQGLQTP------FTFGPGTKLEIK (SEQ ID NO: 249)
```

Legend: 158 VK (grey shaded) CDRs intercalated in human AB064054 FW to generate 158RKA

TABLE 39

Generation of 158RKAss DNA Sequence
Intercalation of 158VK into AB064054 FW (SEQ ID NOS: 250-258)

| Region | DNA | Protein |
|---|---|---|
| A19 leader | ATGAGGCTCCCTGCTCAGCTCCTGGGGCTGCTAATGCTC TGGGTCTCTGGATCCAGTGGG(SEQ ID NO: 250) | MRLPAQLLGLLMLWVSGSSG (SEQ ID NO: 251) |
| AB064054 FW1 | GATGTTGTGATGACTCAGTCTCCACTCTCCCTGCCCGTCACCCC TGGAGCGCCGGCCTCCATCTCCTGC(SEQ ID NO: 252) | DVVMTQSPLSLPVTPGAPASISC (SEQ ID NO: 245) |
| 158 CDR1 | AGATCTAGTCAGAGCATTGTACATAGTAATGGAAACACCTATTTAGAA (SEQ ID NO: 253) | RSSQSIVHSNGNTYLE (SEQ ID NO: 241) |

TABLE 39-continued

Generation of 158RKAss DNA Sequence
Intercalation of 158VK into AB064054 FW (SEQ ID NOS: 250-258)

| Region | DNA | Protein |
|---|---|---|
| AB064054 FW2 | TGGTATCTGCAGAAGCCAGGGCAGTCTCCAAAGCTCCTGATCTAT<br>(SEQ ID NO: 254) | WYLQKPGQSPKLLIY<br>(SEQ ID NO: 246) |
| 158 CDR2 | AAAGTTTCCAACCGATTTTCT<br>(SEQ ID NO: 255) | KVSNRFS<br>(SEQ ID NO: 242) |
| AB064054 FW3 | GGAGTCCCTGACAGGTTCAGTGGCAGTGGGTCAGGCACAGATTTTACAC<br>TGAGAATCAGCAGAGTGGAGGCTGAGGATGTTGGAATTTATTACTGC<br>(SEQ ID NO: 256) | GVPDRFSGSGSGTDFTLRISRVEAE<br>DVGIYYC<br>(SEQ ID NO: 247) |
| 158 CDR3 | TTTCAAGGTTCACATGTTCCTCCGACG<br>(SEQ ID NO: 257) | FQGSHVPPT<br>(SEQ ID NO: 243) |
| AB064054 FW4 | TTCGGCCCTGGGACCAAATTGGAAATCAAA<br>(SEQ ID NO: 258) | FGPGTKLEIK<br>(SEQ ID NO: 248) |

Legend: A19 leader and AB064054 with intercalated 158 VK (grey-shaded) CDRs to generate 158RKAss

TABLE 40

158RKAss DNA sequence (SEQ ID NO: 259) ATGAGGCTCCCTGCTCAGCTCCTGGGGCTGCTAATGCTCTGGGTCTCTGGATCCAGTGGGGATGTTGTGATGACTCAGTCT 81
⊢splice 4.0⊣
(SEQ ID NO: 260)  M  R  L  P  A  Q  L  L  G  L  L  M  L  W  V  S  G  S  S  G  D  V  V  M  T  Q  S CCACTCTCCCTGCCCGTCACCCCTGGAGCGCCGGCCTCCATCTCCTGCAGATCTAGTCAGAGCATTGTACATAGTAATGGA 162
 P  L  S  L  P  V  T  P  G  A  P  A  S  I  S  C  R  S  S  Q  S  I  V  H  S  N  G AACACCTATTTAGAATGGTATCTGCAGAAGCCAGGGCAGTCTCCAAAGCTCCTGATCTATAAAGTTTCCAACCGATTTTCT 243
                   ⊢splice 5.5⊣
 N  T  Y  L  E  W  Y  L  Q  K  P  G  Q  S  P  K  L  L  I  Y  K  V  S  N  R  F  S GGAGTCCCTGACAGGTTCAGTGGCAGTGGGTCAGGCACAGATTTTACACTGAGAATCAGCAGAGTGGAGGCTGAGGATGTT 324
                ⊢splice 5.0⊣
              ⊢splice 4.4⊣
 G  V  P  D  R  F  S  G  S  G  S  G  T  D  F  T  L  R  I  S  R  V  E  A  E  D  V GGAATTTATTACTGCTTTCAAGGTTCACATGTTCCTCCGACGTTCGGCCCTGGGACCAAATTGGAAATCAAA 396
 G  I  Y  Y  C  F  Q  G  S  H  V  P  P  T  F  G  P  G  T  K  L  E  I  K Legend: Splice donor sites predicted by Lasergene 6.0 GeneQuest analysis, together with their score, using the human_ds_2 matrix with a threshold of 4.2.

TABLE 41

Mutations in 158RKA removing splice sites in 158RKA

```
  1 ATGAGGCTCCCTGCTCAGCTCCTGGGGCTGCTAATGCTCTGGGTCTCTGGAAGCAGTGGG 158RKA       (SEQ ID NO: 261)
  1 ....................................................TC....... 158RKAss    (SEQ ID NO: 262)

61 GATGTTGTGATGACTCAGTCTCCACTCTCCCTGCCCGTCACCCCTGGAGCGCCGGCCTCC 158RKA
 61 ............................................................ 158RKAss

121 ATCTCCTGCAGATCTAGTCAGAGCATTGTACATAGTAATGGAAACACCTATTTAGAGTGG 158RKA
121 ........................................................A... 158RKAss

181 TATCTTCAAAAGCCAGGGCAGTCTCCAAAGCTCCTGATCTATAAAGTTTCCAACCGATTT 158RKA
181 .....G..G................................................... 158RKAss
```

TABLE 41-continued

Mutations in 158RKA removing splice sites in 158RKA

```
241 TCTGGAGTCCCTGACAGGTTCAGTGGAAGTGGATCAGGCACAGATTTTACACTGAGAATC 158RKA
241 .........................C.....G........................... 158RKAss

301 AGCAGAGTGGAGGCTGAGGATGTTGGAATTTATTACTGCTTTCAAGGTTCACATGTTCCT 158RKA
301 ............................................................ 158RKAss

361 CCGACGTTCGGCCCTGGGACCAAATTGGAAATCAAA                         158RKA
361 ....................................                         158RKAss
```

Legend: 158RKA DNA sequence compared to 158RKAss (Table 5.13.2) which contains predicted splice sites. Residues identical to 158RKA are identified by a dot.

TABLE 42

DNA and protein sequence of 158RKA

```
(SEQ ID   ATGAGGCTCCCTGCTCAGCTCCTGGGGCTGCTAATGCTCTGGGTCTCTGGAAGCAGTGGGGATGTTGTGATGACTCAGTCT    81
NO: 263)  ◼━━━━━━━━━━ A19 leader sequence ━━━━━━━━━━▶  □━━━━ 58RKA FW1 ━━━
(SEQ ID    M  R  L  P  A  Q  L  L  G  L  L  M  L  W  V  S  G  S  S  G  D  V  V  M  T  Q  S
NO: 264)

CCACTCTCCCTGCCCGTCACCCCTGGAGCGCCGGCCTCCATCTCCTGCAGATCTAGTCAGAGCATTGTACATAGTAATGGA   162
          ━━━━━━━━━━ 158RKA FW1 ━━━━━━━━━━▶ ◼━━━ CDR1 ━━━
            P  L  S  L  P  V  T  P  G  A  P  A  S  I  S  C  R  S  S  Q  S  I  V  H  S  N  G

AACACCTATTTAGAGTGGTATCTTCAAAAGCCAGGGCAGTCTCCAAAGCTCCTGATCTATAAAGTTTCCAACCGATTTTCT   243
          ━━ CDR1 ━▶ □━━━━━━━━━ 158RKA FW2 ━━━━━━━━━▶ ◼━━ CDR2 ━━▶
            N  T  Y  L  E  W  Y  L  Q  K  P  G  Q  S  P  K  L  L  I  Y  K  V  S  N  R  F  S

GGAGTCCCTGACAGGTTCAGTGGAAGTGGATCAGGCACAGATTTTACACTGAGAATCAGCAGAGTGGAGGCTGAGGATGTT   324
          □━━━━━━━━━━━━━━━ 158RKA FW3 ━━━━━━━━━━━━━━━
            G  V  P  D  R  F  S  G  S  G  S  G  T  D  F  T  L  R  I  S  R  V  E  A  E  D  V

GGAATTTATTACTGCTTTCAAGGTTCACATGTTCCTCCGACGTTCGGCCCTGGGACCAAATTGGAAATCAAA            396
          158RKA FW3 ▶ ◼━ CDR3 ━▶ □━━━━━ 158RKA FW4 ━━━━━▶
            G  I  Y  Y  C  F  Q  G  S  H  V  P  P  T  F  G  P  G  T  K  L  E  I  K
```

TABLE 43

Further version of humanized 158VHA (158RHB, 158RHC, 158RHD)

| Kabat number[6] | 1234567890123456789012345678901234567890123456789012A34567890123456789 |
|---|---|
| 158RHA | EVQLVESGGGLVQPGGSLRLSCSASGFTFSSFGMHWVRQAPGKGLEWVAYISSGSSTIYYGDTVKGRFTI |
| 158RHB | DVQLVESGGGLVQPGGSLRLSCSASGFTFSSFGMHWVRQAPGKGLEWVAYISSGSSTIYYGDTVKGRFTI |
| 158RHC | EVQLVESGGGLVQPGGSLRLSCSASGFTFSSFGMHWVRQAPGKGLEWVAYISSGSSTIYYGDTVKGRFTI |
| 158RHD | EVQLVESGGGLVQPGGSLRLSCSASGFTFSSFGMHWVRQAPGKGLEWVAYISSGSSTIYYGDTVKGRFTI |

| | Kabat number[6] | 7    8    9    10    11 |  |
| --- | --- | --- | --- |
| | | 0123456789012ABC345678901234567890ABCDEFv1234567890123 | |
| | 158RHA | SRDNAKNSLFLQMSSLRAEDTAVYYCAREGGYYYGRSYYTMDYWGQGTTVTVS | (SEQ ID NO: 265) |
| | 158RHB | SRDNAKNSLFLQMSSLRAEDTAVYYCAREGGYYYGRSYYTMDYWGQGTTVTVS | (SEQ ID NO: 266) |
| | 158RHC | SRDNPKNSLFLQMSSLRAEDTAVYYCAREGGYYYGRSYYTMDYWGQGTTVTVS | (SEQ ID NO: 267) |
| | 158RHD | SRDNAKNSLFLQMTSLRAEDTAVYYCAREGGYYYGRSYYTMDYWGQGTTVTVS | (SEQ ID NO: 268) |

TABLE 44

Further version of humanized 158VKA (158RKB,158RKC)

| Kabat number | 1         2         3         4         5         6<br>12345678901234567890123456ABCDE8901234567890123456789012345678901234567890 |  |
|---|---|---|
| 158RKA | DVVMTQSPLSLPVTPGAPASISCRSSQSIVHSNGNTYLEWYLQKPGQSPKLLIYKVSNRFSGVPD | |
| 158RKB | DVLMTQSPLSLPVTPGAPASISCRSSQSIVHSNGNTYLEWYLQKPGQSPKLLIYKVSNRFSGVPD | |
| 158RKC | DVVMTQSPLSLPVTPGAPASISCRSSQSIVHSNGNTYLEWYLQKPGQSPKLLIYKVSNRFSGVPD | |

| | Kabat number | 7         8         9         10<br>1234567890123456789012345678901234567 | |
|---|---|---|---|
| | 158RKA | RFSGSFSGTDFTLRISRVEAEDVGIYYCFQGSHVPPTFGPGTKLEIK | (SEQ ID NO: 269) |
| | 158RKB | RFSGSGSGTDFTLRISRVEAEDVGIYYCFQGSHVPPTFGPGTKLEIK | (SEQ ID NO: 270) |
| | 158RKC | RFSGSGSGTDFTLRISRVEAEDVGIYYCFQGSHVPPTFGGGTKLEIK | (SEQ ID NO: 271) |

The invention claimed is:

1. A method of measuring Aβ protofibrils in a mammal, said method comprising the steps of:
   (a) providing a labeled antibody or fragment thereof, being selective and having high affinity for human Aβ protofibrils, and wherein the labeled antibody or fragment thereof in its six CDR regions comprises:

```
   VH-CDR1   SFGMH;                    (SEQ ID NO: 1)

VH-CDR2   YISSGSSTIYYGDTVKG;        (SEQ ID NO: 2)

VH-CDR3   EGGYYYGRSYYTMDY;          (SEQ ID NO: 3)

VL-CDR1   RSSQSIVHSNGNTYLE;         (SEQ ID NO: 4)

VL-CDR2   KVSNRFS;                  (SEQ ID NO: 5)
             and

VL-CDR3   FQGSHVPPT,                (SEQ ID NO: 6)
             wherein
   ```
   said antibody or fragment thereof is labeled with an agent that generates a measurable signal;
   (b) administering the labeled antibody or fragment thereof to a mammal comprising or suspected of comprising Aβ protofibrils; and
   (c) measuring the concentration of a complex formed between said Aβ protofibril and said antibody or fragment thereof by measuring the signal generated by the agent.

2. The method of claim 1, wherein the agent is labeled with a radioactive ligand.

3. The method of claim 2, wherein the radioactive ligand is selected from the group $I^{131}$, $C^{14}$, $H^{3}$, or $Gallium^{68}$.

4. The method of any one of claims 1-3, wherein said measuring is used in the diagnosis of Alzheimer's disease or Down's syndrome.

* * * * *